(12) United States Patent
Pike

(10) Patent No.: US 8,138,183 B2
(45) Date of Patent: Mar. 20, 2012

(54) MORPHOLINO PYRIMIDINE DERIVATIVES USED IN DISEASES LINKED TO MTOR KINASE AND/OR PI3K

(75) Inventor: Kurt Gordon Pike, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/668,056

(22) PCT Filed: Jul. 8, 2008

(86) PCT No.: PCT/GB2008/050548
§ 371 (c)(1),
(2), (4) Date: Jun. 18, 2010

(87) PCT Pub. No.: WO2009/007750
PCT Pub. Date: Jan. 15, 2009

(65) Prior Publication Data
US 2010/0249131 A1    Sep. 30, 2010

Related U.S. Application Data

(60) Provisional application No. 60/948,539, filed on Jul. 9, 2007.

(51) Int. Cl.
*A61K 31/535*    (2006.01)
*C07D 413/04*    (2006.01)

(52) U.S. Cl. ................................ 514/235.8; 544/122

(58) Field of Classification Search .............. 544/122; 514/235.8
See application file for complete search history.

(56) References Cited

U.S. PATENT DOCUMENTS

| 5,250,530 | A | 10/1993 | Giencke et al. |
|---|---|---|---|
| 2002/0086858 | A1 | 7/2002 | Breu et al. |
| 2007/0049603 | A1 | 3/2007 | Miknis et al. |
| 2007/0299068 | A1 | 12/2007 | Karp et al. |

FOREIGN PATENT DOCUMENTS

| EP | 0407899 | B1 | 3/1995 |
|---|---|---|---|
| EP | 1277738 | A1 | 1/2003 |
| GB | 2431156 | A | 4/2007 |
| JP | 200791649 | A | 4/2007 |
| JP | 2007119450 | A | 5/2007 |
| JP | 2007246474 | A | 9/2007 |
| WO | 0238551 | A1 | 5/2002 |
| WO | 2004048365 | A1 | 6/2004 |
| WO | 2005000404 | A2 | 1/2005 |
| WO | 2006005914 | A1 | 1/2006 |
| WO | 2006005915 | A1 | 1/2006 |
| WO | 2006005918 | A1 | 1/2006 |
| WO | 2006053227 | A2 | 5/2006 |
| WO | 2006124662 | A1 | 11/2006 |
| WO | 2006124874 | A2 | 11/2006 |
| WO | 2006125554 | A1 | 11/2006 |
| WO | 2007005673 | A1 | 1/2007 |
| WO | 2007013691 | A1 | 2/2007 |
| WO | 2007041130 | A2 | 4/2007 |
| WO | 2007041358 | A2 | 4/2007 |
| WO | 2007042806 | A1 | 4/2007 |
| WO | 2007042810 | A1 | 4/2007 |
| WO | 2007049041 | A1 | 5/2007 |
| WO | 2007054831 | A2 | 5/2007 |
| WO | 2007063868 | A1 | 6/2007 |
| WO | 2007066099 | A1 | 6/2007 |
| WO | 2007066102 | A1 | 6/2007 |
| WO | 2007066103 | A1 | 6/2007 |
| WO | 2007072163 | A2 | 6/2007 |
| WO | 2007080382 | A1 | 7/2007 |
| WO | 2007084413 | A2 | 7/2007 |
| WO | 2007084786 | A1 | 7/2007 |
| WO | 2007089768 | A2 | 8/2007 |
| WO | 2007105023 | A1 | 9/2007 |
| WO | 2007114323 | A1 | 10/2007 |
| WO | 2007124288 | A1 | 11/2007 |
| WO | 2007126043 | A1 | 11/2007 |
| WO | 2007141571 | A2 | 12/2007 |
| WO | 2008005538 | A2 | 1/2008 |
| WO | 2008023159 | A1 | 2/2008 |
| WO | 2008023180 | A1 | 2/2008 |
| WO | 2008125833 | A1 | 10/2008 |
| WO | 2009007751 | A2 | 1/2009 |

OTHER PUBLICATIONS

SciFinder English Language abstract corresponding to JP2007246474, Sep. 27, 2007.
SciFinder English Language abstract corresponding to JP200791649, Apr. 12, 2007.
SciFinder English Language abstract corresponding to JP2007119450, May 17, 2007.
S.N. Suryawanshi et al 'Chemotherapy of leishmaniasis. Part VII: Synthesis and bioevaluation of substituted terpenyl pyrimidines' European Journal of Medicinal Chemistry, 2007, pp. 1211-1217 vol. 42.
Hui-Ling Wang et al, 'Novel Vanilloid Receptor-1 Antagonists: 3. The Identification of a Second-Generation Clinical Candidate with Improved Physicochemical and Pharmacokinetic Properties' Journal of Medical Chemistry, 2007, pp. 3528-3539 vol. 50.
David D. Davey et al, Design, Synthesis, and Activity of 2-Imidazol-1-ylpyrimidine Derived Inducible Nitric Oxide Synthase Dimerization Inhibitors, Journal of Medicinal Chemistry, 2007, pp. 1146-1157, vol. 50.

(Continued)

*Primary Examiner* — Rebecca Anderson
(74) *Attorney, Agent, or Firm* — AstraZeneca AB; Julie Anne Knight

(57) ABSTRACT

A compound of formula (I) or a pharmaceutically acceptable salt thereof, processes for their preparation, pharmaceutical compositions containing them and their use in therapy, for example in the treatment of proliferative disease such as cancer and particularly in disease mediated by an mTOR kinase and/or one or more PI3K enzyme.

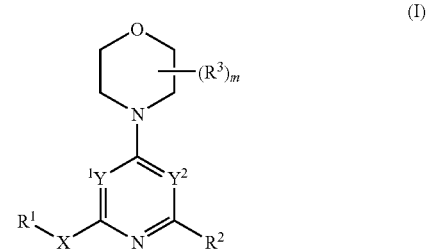

(I)

12 Claims, No Drawings

OTHER PUBLICATIONS

Bernd Dotzauer et al, 2,4-Diamino-9H-pyrimido[4,5-b]indol-5-ols: Synthesis, in vitro cytotoxic activity, and QSAR investigations. Bioorganic & Medicinal Chemitry, 2006, pp. 7282-7292, vol. 14(21).

Sanjay Babu Katiyar et al. Synthesis of 2,4,6-trisubstituted pyrimidine derivatives as a new class of antifilarial topoisomerase II inhibitors, Bioorganic & Medicinal Chemistry Letters, 2005, pp. 47-50, vol. 15(1).

Naveen Chandra et al, Antileishmanial agents part-IV: synthesis and antileishmanial activity of novel terpenyl pyrimidines, European Journal of Medicinal Chemistry, 2005, pp. 552-556, vol. 40.

4-Pyrimidinecarboxamide, 2,6-di-4-Morpholinyl-N-(2-Phenylethyl), CHEMCATS, 2004, XP002348927.

Roland Spitzner et al, Ringschlussreaktionen von 2-Acyl-1-chlorenaminen mit thioamidfunktionellen Verbindungen: Wahlweiser Zugang in die 1,3-Thiazin-und 1,3-Oxazin-Reihe, Monatshefte Fur Chemie Chemical Monthly, 1987, pp. 1383-1394, vol. 118.

A. Kumar et al, A Novel and Convenient Synthesis of 2-Amino-4-(N-alkyl-N-arylamino)-pyrimidines using Polarized Ketene S,S-and S,N-Acetals, Synthesis, 1980, pp. 748-751, vol. 9.

Richard.R. Schmidt et al, Neue Synthese von Pyrimidinderivaten, Chemische Berichte, 1965, pp. 346-351, vol. 98(2).

Minami, Shinaku et al, 2(or 6)-Nitrofurylvinyl-4-substituted aminopyrimidines XP002505932, Database Chemical Abstracts Service Columbus , 1967.

Database Registry On-Line, XP002514432, Chemical Abstracts Service Columbus, Ohio, US, Jan. 3, 2003.
Database Registry On-Line, XP002514433, Chemical Abstracts Service Columbus, Ohio, US, Jan. 3, 2003.
Database Registry On-Line, XP002514434, Chemical Abstracts Service Columbus, Ohio, US, Dec. 31, 2002.
Database Registry On-Line, XP002514435, Chemical Abstracts Service Columbus, Ohio, US, Dec. 31, 2002.
Database Registry On-Line, XP002514436, Chemical Abstracts Service Columbus, Ohio, US, Dec. 31, 2002.
Database Registry On-Line, XP002514437, Chemical Abstracts Service Columbus, Ohio, US, Dec. 31, 2002.
Database Registry On-Line, XP002514438, Chemical Abstracts Service Columbus, Ohio, US, Dec. 31, 2002.
Database Registry On-Line, XP002514439, Chemical Abstracts Service Columbus, Ohio, US, Dec. 31, 2002.
Database Registry On-Line, XP002514440, Chemical Abstracts Service Columbus, Ohio, US, Dec. 31, 2002.
Database Registry On-Line, XP002514441, Chemical Abstracts Service Columbus, Ohio, US, Jun. 4, 2001.
Database Registry On-Line, XP002514442, Chemical Abstracts Service Columbus, Ohio, US, Jun. 4, 2001.
Database Registry On-Line, XP002514443, Chemical Abstracts Service Columbus, Ohio, US, Jun. 4, 2001.
Database Registry On-Line, XP002514444, Chemical Abstracts Service Columbus, Ohio, US, Jun. 4, 2001.
Database Registry On-Line, XP002514445, Chemical Abstracts Service Columbus, Ohio, US, Jun. 4, 2001.
Database Registry On-Line, XP002514446, Chemical Abstracts Service Columbus, Ohio, US, Jun. 4, 2001.
Database Registry On-Line, XP002514447, Chemical Abstracts Service Columbus, Ohio, US, May 30, 2001.
Database Registry On-Line, XP002514448, Chemical Abstracts Service Columbus, Ohio, US, May 30, 2001.
Database Registry On-Line, XP002514449, Chemical Abstracts Service Columbus, Ohio, US, May 30, 2001.
Database Registry On-Line, XP002514450, Chemical Abstracts Service Columbus, Ohio, US, May 30, 2001.
Database Registry On-Line, XP002514451, Chemical Abstracts Service Columbus, Ohio, US, May 30, 2001.
Database Registry On-Line, XP002514452, Chemical Abstracts Service Columbus, Ohio, US, Feb. 6, 2001.
Database Registry On-Line, XP002514453, Chemical Abstracts Service Columbus, Ohio, US, Feb. 6, 2001.
Database Registry On-Line, XP002514454, Chemical Abstracts Service Columbus, Ohio, US, Dec. 6, 2000.
Database Registry On-Line, XP002514455, Chemical Abstracts Service Columbus, Ohio, US, Nov. 17, 2000.
Database Registry On-Line, XP002514456, Chemical Abstracts Service Columbus, Ohio, US, Nov. 17, 2000.
SciFinder English language abstract corresponding to Richard.R. Schmidt, 'Neue Synthese von Pyrimidinderivaten', Chemische Berichte, 1965, pp. 346-351, vol. 98(2).

MORPHOLINO PYRIMIDINE DERIVATIVES USED IN DISEASES LINKED TO MTOR KINASE AND/OR PI3K

CROSS-REFERENCE TO RELATED APPLICATIONS

This application is a U.S. National Stage under 35 U.S.C §371 of International Application No. PCT/GB2008/050548 filed Jul. 8, 2008, which claims the benefit of U.S. Provisional Application No. 60/948,539 filed on Jul. 9, 2007.

The present invention relates to morpholino pyrimidine compounds, processes for their preparation, pharmaceutical compositions containing them and their use in therapy, for example in the treatment of proliferative disease such as cancer and particularly in disease mediated by an mTOR kinase and/or one or more PI3K enzyme.

It is now well understood that deregulation of oncogenes and tumour-suppressor genes contributes to the formation of malignant tumours, for example by way of increased cell proliferation or increased cell survival. It is also known that signalling pathways mediated by the PI3K/mTOR families have a central role in a number of cell processes including proliferation and survival, and deregulation of these pathways is a causative factor in a wide spectrum of human cancers and other diseases.

The mammalian target of the macrolide antibiotic Rapamycin (sirolimus) is the enzyme mTOR. This enzymes belongs to the phosphatidylinositol (PI) kinase-related kinase (PIKK) family of protein kinases, which also includes ATM, ATR, DNA-PK and hSMG-1. mTOR, like other PIKK family members, does not possess detectable lipid kinase activity, but instead functions as a serine/threonine kinase. Much of the knowledge of mTOR signalling is based upon the use of Rapamycin. Rapamycin first binds to the 12 kDa immunophilin FK506-binding protein (FKBP12) and this complex inhibits mTOR signalling (Tee and Blenis, Seminars in Cell and Developmental Biology, 2005, 16, 29-37). The mTOR protein consists of a catalytic kinase domain, an FKBP12-Rapamycin binding (FRB) domain, a putative repressor domain near the C-terminus and up to 20 tandemly-repeated HEAT motifs at the N-terminus, as well as FRAP-ATM-TRRAP (FAT) and FAT C-terminus domain (Huang and Houghton, Current Opinion in Pharmacology, 2003, 3, 371-377).

mTOR kinase is a key regulator of cell growth and has been shown to regulate a wide range of cellular functions including translation, transcription, mRNA turnover, protein stability, actin cytoskeleton reorganisation and autophagy (Jacinto and Hall, Nature Reviews Molecular and Cell Biology, 2005, 4, 117-126). mTOR kinase integrates signals from growth factors (such as insulin or insulin-like growth factor) and nutrients (such as amino acids and glucose) to regulate cell growth. mTOR kinase is activated by growth factors through the PI3K-Akt pathway. The most well characterised function of mTOR kinase in mammalian cells is regulation of translation through two pathways, namely activation of ribosomal S6K1 to enhance translation of mRNAs that bear a 5'-terminal oligopyrimidine tract (TOP) and suppression of 4E-BP1 to allow CAP-dependent mRNA translation.

Generally, investigators have explored the physiological and pathological roles of mTOR using inhibition with Rapamycin and related Rapamycin analogues based on their specificity for mTOR as an intracellular target. However, recent data suggests that Rapamycin displays variable inhibitory actions on mTOR signalling functions and suggest that direct inhibition of the mTOR kinase domain may display substantially broader anti-cancer activities than that achieved by Rapamycin (Edinger et al., Cancer Research, 2003, 63, 8451-8460). For this reason, potent and selective inhibitors of mTOR kinase activity would be useful to allow a more complete understanding of mTOR kinase function and to provide useful therapeutic agents.

There is now considerable evidence indicating that the pathways upstream of mTOR, such as the PI3K pathway, are frequently activated in cancer (Vivanco and Sawyers, Nature Reviews Cancer, 2002, 2, 489-501; Bjornsti and Houghton, Nature Reviews Cancer, 2004, 4, 335-348; Inoki et al., Nature Genetics, 2005, 37, 19-24). For example, components of the PI3K pathway that are mutated in different human tumours include activating mutations of growth factor receptors and the amplification and/or overexpression of PI3K and Akt.

In addition there is evidence that endothelial cell proliferation may also be dependent upon mTOR signalling. Endothelial cell proliferation is stimulated by vascular endothelial cell growth factor (VEGF) activation of the PI3K-Akt-mTOR signalling pathway (Dancey, Expert Opinion on Investigational Drugs, 2005, 14, 313-328). Moreover, mTOR kinase signalling is believed to partially control VEGF synthesis through effects on the expression of hypoxia-inducible factor-1☐ (HIF-1☐) (Hudson et al., Molecular and Cellular Biology, 2002, 22, 7004-7014). Therefore, tumour angiogenesis may depend on mTOR kinase signalling in two ways, through hypoxia-induced synthesis of VEGF by tumour and stromal cells, and through VEGF stimulation of endothelial proliferation and survival through PI3K-Akt-mTOR signalling.

These findings suggest that pharmacological inhibitors of mTOR kinase should be of therapeutic value for treatment of the various forms of cancer comprising solid tumours such as carcinomas and sarcomas and the leukaemias and lymphoid malignancies. In particular, inhibitors of mTOR kinase should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

In addition to tumourigenesis, there is evidence that mTOR kinase plays a role in an array of hamartoma syndromes. Recent studies have shown that the tumour suppressor proteins such as TSC1, TSC2, PTEN and LKB1 tightly control mTOR kinase signalling. Loss of these tumour suppressor proteins leads to a range of hamartoma conditions as a result of elevated mTOR kinase signalling (Tee and Blenis, Seminars in Cell and Developmental Biology, 2005, 16, 29-37). Syndromes with an established molecular link to dysregulation of mTOR kinase include Peutz-Jeghers syndrome (PJS), Cowden disease, Bannayan-Riley-Ruvalcaba syndrome (BRRS), Proteus syndrome, Lhermitte-Duclos disease and Tuberous Sclerosis (TSC) (Inoki et al., Nature Genetics, 2005, 37, 19-24). Patients with these syndromes characteristically develop benign hamartomatous tumours in multiple organs.

Recent studies have revealed a role for mTOR kinase in other diseases (Easton & Houghton, Expert Opinion on Therapeutic Targets, 2004, 8, 551-564). Rapamycin has been demonstrated to be a potent immunosuppressant by inhibiting antigen-induced proliferation of T cells, B cells and antibody production (Sehgal, Transplantation Proceedings, 2003, 35, 7S-14S) and thus mTOR kinase inhibitors may also be useful immunosuppressives Inhibition of the kinase activity of mTOR may also be useful in the prevention of restenosis, that is the control of undesired proliferation of normal cells in the vasculature in response to the introduction of stents in the treatment of vasculature disease (Morice et al., New England Journal of Medicine, 2002, 346, 1773-1780). Furthermore, the Rapamycin analogue, everolimus, can reduce the severity and incidence of cardiac allograft vasculopathy (Eisen et al., New England Journal of Medicine, 2003, 349, 847-858). Elevated mTOR kinase activity has been associated with cardiac hypertrophy, which is of clinical importance as a major risk factor for heart failure and is a consequence of increased cellular size of cardiomyocytes (Tee & Blenis, Seminars in Cell and Developmental Biology, 2005, 16, 29-37). Thus mTOR kinase inhibitors are expected to be of value in the prevention and treatment of a wide variety of diseases in addition to cancer.

It is also believed that a number of these morpholino pyrimidine derivatives may have inhibitory activity against the phosphatidylinositol (PI) 3-kinases family of kinases.

Phosphatidylinositol (PI) 3-kinases (PI3Ks) are ubiquitous lipid kinases that function both as signal transducers downstream of cell-surface receptors and in constitutive intracellular membrane and protein trafficking pathways. All PI3Ks are dual-specificity enzymes with a lipid kinase activity that phosphorylates phosphoinositides at the 3-hydroxy position, and a less well characterised protein kinase activity. The lipid products of PI3K-catalysed reactions comprising phosphatidylinositol 3,4,5-trisphosphate [PI(3,4,5)P$_3$], phosphatidylinositol 3,4-bisphosphate [PI(3,4)P$_2$] and phosphatidylinositol 3-monophosphate [PI(3)P] constitute second messengers in a variety of signal transduction pathways, including those essential to cell proliferation, adhesion, survival, cytoskeletal rearrangement and vesicle trafficking PI(3)P is constitutively present in all cells and its levels do not change dramatically following agonist stimulation. Conversely, PI(3,4)P$_2$ and PI(3,4,5)P$_3$ are nominally absent in most cells but they rapidly accumulate on agonist stimulation.

The downstream effects of PI3K-produced 3-phosphoinositide second messengers are mediated by target molecules containing 3-phosphoinositide binding domains such as the pleckstrin homology (PH) domain and the recently identified FYVE and phox domains. Well-characterised protein targets for PI3K include PDK1 and protein kinase B (PKB). In addition, tyrosine kinases like Btk and Itk are dependent on PI3K activity.

The PI3K family of lipid kinases can be classified into three groups according to their physiological substrate specificity (Vanhaesebroeck et al., Trends in Biol. Sci., 1997, 22, 267). Class III PI3K enzymes phosphorylate PI alone. In contrast, Class II PI3K enzymes phosphorylate both PI and PI 4-phosphate [PI(4)P]. Class I PI3K enzymes phosphorylate PI, PI(4)P and PI 4,5-bisphosphate [PI(4,5)P$_2$], although only PI(4,5)P$_2$ is believed to be the physiological cellular substrate. Phosphorylation of PI(4,5)P$_2$ produces the lipid second messenger PI(3,4,5)P$_3$. More distantly related members of the lipid kinase superfamily are Class IV kinases such as mTOR (discussed above) and DNA-dependent kinase that phosphorylate serine/threonine residues within protein substrates. The most studied and understood of the PI3K lipid kinases are the Class I PI3K enzymes.

Class I PI3Ks are heterodimers consisting of a p110 catalytic subunit and a regulatory subunit. The family is further divided into Class Ia and Class Ib enzymes on the basis of regulatory partners and the mechanism of regulation. Class Ia enzymes consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI3Ks are generally activated in response to growth factor-stimulation of receptor tyrosine kinases via interaction of their regulatory subunit SH2 domains with specific phospho-tyrosine residues of activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor systems (GPCRs) and its expression appears to be limited to leukocytes and cardiomyocytes.

There is now considerable evidence indicating that Class Ia PI3K enzymes contribute to tumourigenesis in a wide variety of human cancers, either directly or indirectly (Vivanco and Sawyers, Nature Reviews Cancer, 2002, 2, 489-501). For example, the p110α subunit is amplified in some tumours such as those of the ovary zo (Shayesteh et al., Nature Genetics, 1999, 21, 99-102) and cervix (Ma et al., Oncogene, 2000, 19, 2739-2744). More recently, activating mutations within the catalytic site of the p110α catalytic subunit have been associated with various other tumours such as those of the colorectal region and of the breast and lung (Samuels et al., Science, 2004, 304, 554). Tumour-related mutations in the p85α regulatory subunit have also been identified in cancers such as those of the ovary and colon (Philp et al., Cancer Research, 2001, 61, 7426-7429). In addition to direct effects, it is believed that activation of Class Ia PI3Ks contributes to tumourigenic events that occur upstream in signalling pathways, for example by way of ligand-dependent or ligand-independent activation of receptor tyrosine kinases, GPCR systems or integrins (Vara et al., Cancer Treatment Reviews, 2004, 30, 193-204). Examples of such upstream signalling pathways include over-expression of the receptor tyrosine kinase erbB2 in a variety of tumours leading to activation of PI3K-mediated pathways (Harari et al., Oncogene, 2000, 19, 6102-6114) and over-expression of the ras oncogene (Kauffmann-Zeh et al., Nature, 1997, 385, 544-548). In addition, Class Ia PI3Ks may contribute indirectly to tumourigenesis caused by various downstream signalling events. For example, loss of the effect of the PTEN tumour-suppressor phosphatase that catalyses conversion of PI(3,4,5)P$_3$ back to PI(4,5)P$_2$ is associated with a very broad range of tumours via deregulation of PI3K-mediated production of PI(3,4,5)P$_3$ (Simpson and Parsons, Exp. Cell Res., 2001, 264, 29-41). Furthermore, augmentation of the effects of other PI3K-mediated signalling events is believed to contribute to a variety of cancers, for example by activation of Akt (Nicholson and Anderson, Cellular Signalling, 2002, 14, 381-395).

In addition to a role in mediating proliferative and survival signalling in tumour cells, there is evidence that Class Ia PI3K enzymes contribute to tumourigenesis in tumour-associated stromal cells. For example, PI3K signalling is known to play an important role in mediating angiogenic events in endothelial cells in response to pro-angiogenic factors such as VEGF (Abid et al., Arterioscler. Thromb. Vasc. Biol., 2004, 24, 294-300). As Class I PI3K enzymes are also involved in motility and migration (Sawyer, Expert Opinion Investig. Drugs, 2004, 13, 1-19), PI3K enzyme inhibitors should provide therapeutic benefit via inhibition of tumour cell invasion and metastasis. In addition, Class I PI3K enzymes play an important role in the regulation of immune cells contributing to pro-tumourigenic effects of inflammatory cells (Coussens and Werb, Nature, 2002, 420, 860-867).

These findings suggest that pharmacological inhibitors of Class I PI3K enzymes will be of therapeutic value for the treatment of various diseases including different forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

PI3Kγ, the Class Ib PI3K, is activated by GPCRs, as was finally demonstrated in mice lacking the enzyme. Thus, neutrophils and macrophages derived from PI3Kγ-deficient animals failed to produce PI(3,4,5)P$_3$ in response to stimulation with various chemotactic substances (such as IL-8, C5a, fMLP and MIP-1a), whereas signalling through protein tyrosine kinase-coupled receptors to Class Ia PI3Ks was intact (Hirsch et al., Science, 2000, 287(5455), 1049-1053; Li et al., Science, 2002, 287(5455), 1046-1049; Sasaki et al., Science 2002, 287(5455), 1040-1046). Furthermore, PI(3,4,5)P$_3$-mediated phosphorylation of PKB was not initiated by these GPCR ligands in PI3Kγ-null cells. Taken together, the results demonstrated that, at least in resting haematopoietic cells, PI3Kγ is the sole PI3K isoform that is activated by GPCRs in vivo. When murine bone marrow-derived neutrophils and peritoneal macrophages from wild-type and PI3Kγ$^{-/-}$ mice were tested in vitro, a reduced, but not completely abrogated, performance in chemotaxis and adherence assays was observed. However, this translated into a drastic impairment of IL-8 driven neutrophil infiltration into tissues (Hirsch et al., Science, 2000, 287(5455), 1049-1053.). Recent data suggest that PI3Kγ is involved in the path finding process rather than in the generation of mechanical force for motility, as random migration was not impaired in cells that lacked PI3Kγ (Hannigan et al., Proc. Nat. Acad. of Sciences of U.S.A., 2002, 99(6), 3603-8). Data linking PI3Kγ to respiratory disease pathology came with the demonstration that PI3Kγ has a central role in regulating endotoxin-induced lung infiltration and activation of neutrophils leading to acute lung injury (Yum et al., J. Immunology, 2001, 167(11), 6601-8). The fact that although PI3Kγ is highly expressed in leucocytes, its loss seems not to interfere with haematopoiesis, and the fact that PI3Kγ-null mice are viable and fertile further implicates this PI3K isoform as a potential drug target. Work with knockout mice also established that PI3Kγ is an essential amplifier of mast cell activation (Laffargue et al., Immunity, 2002, 16(3), 441-451).

Thus, in addition to tumourigenesis, there is evidence that Class I PI3K enzymes play a role in other diseases (Wymann et al., Trends in Pharmacological Science, 2003, 24, 366-376). Both Class Ia PI3K enzymes and the single Class Ib enzyme have important roles in cells of the immune system (Koyasu, Nature Immunology, 2003, 4, 313-319) and thus they are therapeutic targets for inflammatory and allergic indications. Recent reports demonstrate that mice deficient in PI3Kγ and PI3Kδ are viable, but have attenuated inflammatory and allergic responses (Ali et al., Nature, 2004, 431 (7011), 1007-11). Inhibition of PI3K is also useful to treat cardiovascular disease via anti-inflammatory effects or directly by affecting cardiac myocytes (Prasad et al., Trends in Cardiovascular Medicine, 2003, 13, 206-212). Thus, inhibitors of Class I PI3K enzymes are expected to be of value in the prevention and treatment of a wide variety of diseases in addition to cancer.

Several compounds that inhibit PI3Ks and phosphatidylinositol (PI) kinase-related kinase (PI3KKs) have been identified, including wortmannin and the quercetin derivative LY294002. These compounds are reasonably specific inhibitors of PI3Ks and PI3KKs over other kinases but they lack potency and display little selectivity within the PI3K families.

Accordingly, it would be desirable to provide further effective mTOR and/or PI3K inhibitors for use in the treatment of cancer, inflammatory or obstructive airways diseases, immune or cardiovascular diseases.

Morpholino pyrimidine derivatives and PI3K inhibitors are known in the art.

International Patent Application WO 2004/048365 discloses compounds that possess PI3K enzyme inhibitory activity and are useful in the treatment of cancer. These compounds are arylamino- and heteroarylamino-substituted pyrimidines which differ from the compounds of the present invention by virtue of their arylamino- and heteroarylamino substituents. WO 2004/048365 does not disclose compounds with the —XR$^1$ substituents of the present invention. Inhibitors of PI3K activity useful in the treatment of cancer are also disclosed in European Patent Application 1 277 738 which mentions 4-morpholino-substituted bicyclic heteroaryl compounds such as quinazoline and pyrido[3,2-d]pyrimidine derivatives and 4-morpholino-substituted tricyclic heteroaryl compounds but not monocyclic pyrimidine derivatives.

WO2007/080382, WO2008/023180 and WO2008/023159 disclose compounds that possess mTOR and/or PI3K enzyme inhibitory activity and are useful in the treatment of cancer. WO2007/080382, WO2008/023180 and WO2008/023159 do not disclose compounds comprising a thiourea substituent.

A number of compounds such as 4-morpholin-4-yl-6-(phenylsulfonylmethyl)-2-pyridin-4-yl-pyrimidine and 4-{6-[(phenylsulfonyl)methyl]-2-pyridin-2-ylpyrimidin-4-yl}morpholine have been registered in the Chemical Abstracts database but no utility has been indicated and there is no suggestion that these compounds have mTOR and/or PI3K inhibitory activity or useful therapeutic properties.

Surprisingly, we have found that certain morpholino pyrimidine derivatives possess useful therapeutic properties. Without wishing to be bound by theoretical constraints, it is believed that the therapeutic usefulness of the derivatives is derived from their inhibitory activity against mTOR kinase and/or one or more PI3K enzyme (such as the Class Ia enzyme and/or the Class Ib enzyme). Because signalling pathways mediated by the PI3K/mTOR families have a central role in a number of cell processes including proliferation and survival, and because deregulation of these pathways is a causative factor in a wide spectrum of human cancers and other diseases, it is expected that the derivatives will be therapeutically useful. In particular, it is expected that the derivatives will have anti-proliferative and/or apoptotic properties which means that they will be useful in the treatement of proliferative disease such as cancer. The compounds of the present invention may also be useful in inhibiting the uncontrolled cellular proliferation which arises from various non-malignant diseases such as inflammatory diseases, obstructive airways diseases, immune diseases or cardiovascular diseases.

Generally, the compounds of the present invention possess potent inhibitory activity against mTOR kinase but the compound may also possess potent inhibitory activity against one or more PI3K enzyme (such as the Class Ia enzyme and/or the Class Ib enzyme).

In accordance with an aspect of the present invention, there is provided a compound of formula (I)

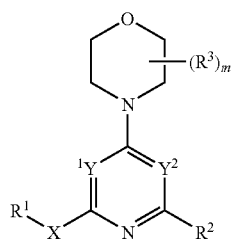

formula (I)

or a pharmaceutically acceptable salt thereof; wherein
m is 0, 1, 2, 3 or 4;
$^1Y$ and $Y^2$ are independently N or $CR^8$ provided that one of $^1Y$ and $Y^2$ is N and the other is $CR^8$;
X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7C$≡C—, —$NR^4CR^6R^7$—, —$OCR^6R^7$—, —$SCR^6R^7$—, —S(O)$CR^6R^7$—, —$S(O)_2CR^6R^7$, —C(O)$NR^4CR^6R^7$—, —$NR^4C(O)CR^6R^7$—, —$NR^4C(O)NR^5CR^6R^7$—, —$NR^4S(O)_2CR^6R^7$—, —$S(O)_2NR^4CR^6R^7$—, —C(O)$NR^4$—, —$NR^4C(O)NR^5$—, —$S(O)_2NR^4$— and —$NR^4S(O)_2$—;
$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —$OR^9$, —$SR^9$, —$SOR^9$, —$SO_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and —$NR^9SO_2R^{10}$;
$R^2$ is a group selected from $C_{1-6}$alkyl, carbocyclyl and heterocyclyl which group is substituted by —$NR^{17}CSNR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;
each $R^3$, when present, is independently selected from halo, cyano, nitro, —$R^{13}$, —$OR^{13}$, —$SR^{13}$, —$SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$NR^{13}CO_2R^{14}$ and —$NR^{13}SO_2R^{14}$;
$R^4$ and $R^5$ are independently hydrogen or $C_{1-6}$alkyl;
or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^6$ and $R^7$ are independently selected from hydrogen, halo, cyano, nitro and $C_{1-6}$alkyl;

$R^8$ is selected from hydrogen, halo, cyano and $C_{1-6}$alkyl;
$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$ alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided a compound of formula (I)

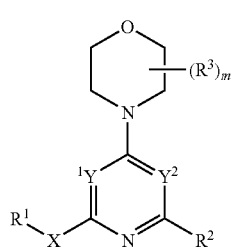

formula (I)

or a pharmaceutically acceptable salt thereof; wherein
m is 0, 1, 2, 3 or 4;
$^1Y$ and $Y^2$ are independently N or $CR^8$ provided that one of $^1Y$ and $Y^2$ is N and the other is $CR^8$;
X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;
$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, $-OR^9$, $-SR^9$, $-SOR^9$, $-SO_2R^9$, $-COR^9$, $-CO_2R^9$, $-CONR^9R^{10}$, $-NR^9R^{10}$, $-N^9COR^{10}$, $-NR^9CO_2R^{10}$, $-NR^9CONR^{10}R^{15}$, $-NR^9COCONR^{10}R^{15}$ and $-NR^9SO_2R^{10}$;
or $X-R^1$ is $-CR^6R^7OH$;
$R^2$ is a group selected from $C_{1-6}$alkyl, carbocyclyl and heterocyclyl which group is substituted by $-NR^{17}CSNR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;
each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;
$R^4$ and $R^5$ are independently hydrogen or $C_{1-6}$alkyl;
or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;
$R^8$ is selected from hydrogen, halo, cyano and $C_{1-6}$alkyl;
$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino , $C_{1-6}$alkanoyl($C_{1-6}$alkyl)amino, carbamoyl, $C_{1-6}$alkylcarbamoyl and bis($C_{1-6}$alkyl)carbamoyl;
$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl,
for use as a medicament in the treatment of proliferative disease.

In accordance with another aspect of the present invention, there is provided a compound of formula (I)

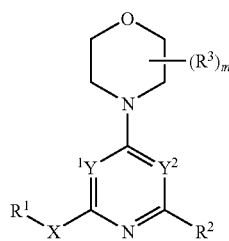

formula (I)

or a pharmaceutically acceptable salt thereof; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)NR^5CR^6R^7-$, $-S(O)_2NR^4CR^6R^7$, $-C(O)NR^4-$, $-NR^4C(O)-$, $-NR^4C(O)NR^5-$, $-S(O)_2NR^4-$ and $-NR^4S(O)_2-$;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

or $X-R^1$ is $-CR^6R^7OH$;

$R^2$ is a group selected from $C_{1-6}$alkyl, carbocyclyl and heterocyclyl which group is substituted by $-NR^{17}CSNR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl for use as a medicament in the treatment of proliferative disease.

In accordance with another aspect of the present invention, there is provided the use of a compound of formula (I)

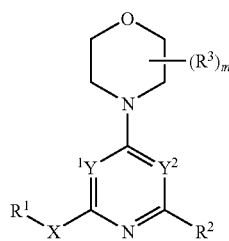

formula (I)

or a pharmaceutically acceptable salt thereof; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from $-CR^4=CR^5-$, $-CR^4=CR^5CR^6R^7-$, $-CR^6R^7CR^5=CR^4-$, $-C\equiv C-$, $-C\equiv CCR^6R^7-$, $-CR^6R^7C\equiv C-$, $-NR^4CR^6R^7-$, $-OCR^6R^7-$, $-SCR^6R^7-$, $-S(O)CR^6R^7-$, $-S(O)_2CR^6R^7-$, $-C(O)NR^4CR^6R^7-$, $-NR^4C(O)CR^6R^7-$, $-NR^4C(O)NR^5CR^6R^7-$, $-NR^4S(O)_2CR^6R^7-$, $-S(O)_2NR^4CR^6R^7-$, $-C(O)NR^4-$, $-NR^4C(O)-$, $-NR^4C(O)NR^5-$, $-S(O)_2NR^4-$ and $-NR^4S(O)_2-$;

$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $-R^9$, $-OR^9$, $-SR^9$, $-SOR^9$, $-SO_2R^9$, $-COR^9$, $-CO_2R^9$, $-CONR^9R^{10}$, $-NR^9R^{10}$, $-NR^9COR^{10}$, $-NR^9CO_2R^{10}$, $-NR^9CONR^{10}R^{15}$, $-NR^9COCONR^{10}R^{15}$ and $-NR^9SO_2R^{10}$;

$R^2$ is a group selected from $C_{1-6}$alkyl, carbocyclyl and heterocyclyl which group is substituted by $-NR^{17}CSNR^{18}R^{19}$ and optionally substituted by one or more substituent group independently selected from halo, cyano, nitro, $-R^{11}$, $-OR^{11}$, $-SR^{11}$, $-SOR^{11}$, $-SO_2R^{11}$, $-COR^{11}$, $-CO_2R^{11}$, $-CONR^{11}R^{12}$, $-NR^{11}R^{12}$, $-NR^{11}COR^{12}$, and $-NR^{11}COCONR^{12}R^{16}$;

each $R^3$, when present, is independently selected from halo, cyano, nitro, $-R^{13}$, $-OR^{13}$, $-SR^{13}$, $-SOR^{13}$, $-SO_2R^{13}$, $-COR^{13}$, $-CO_2R^{13}$, $-CONR^{13}R^{14}$, $-NR^{13}R^{14}$, $-NR^{13}COR^{14}$, $-NR^{13}CO_2R^{14}$ and $-NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with another aspect of the present invention, there is provided the use of a compound of formula (I)

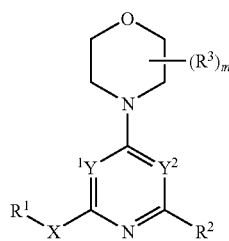

formula (I)

or a pharmaceutically acceptable salt thereof; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —CR$^4$=CR$^5$—, —CR$^4$=CR$^5$CR$^6$R$^7$—, —CR$^6$R$^7$CR$^5$=CR$^4$—, —C≡C—, —C≡CCR$^6$R$^7$—, —CR$^6$R$^7$C≡C—, —NR$^4$CR$^6$R$^7$—, —OCR$^6$R$^7$—, —SCR$^6$R$^7$—, —S(O) CR$^6$R$^7$—, —S(O)$_2$CR$^6$R$^7$—, —C(O)NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —S(O)$_2$NR$^4$CR$^6$R$^7$—, —C(O) NR$^4$—, —NR$^4$C(O)—, —NR$^4$C(O)NR$^5$—, —S(O)$_2$NR$^4$— and —NR$^4$S(O)$_2$—;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, —R$^9$, —OR$^9$, —SR$^9$, —SOR$^9$, —SO$_2$R$^9$, —COR$^9$, —CO$_2$R$^9$, —CONR$^9$R$^{10}$, —NR$^9$R$^{10}$, —NR$^9$COR$^{10}$, —NR$^9$CO$_2$R$^{10}$, —NR$^9$CONR$^{10}$R$^{15}$, —NR$^9$COCONR$^{10}$R$^{15}$ and —NR$^9$SO$_2$R$^{10}$;

or X—R$^1$ is —CR$^6$R$^7$OH;

$R^2$ is a group selected from $C_{1-6}$alkyl, carbocyclyl and heterocyclyl which group is substituted by —NR$^{17}$CSNR$^{18}$R$^{19}$ and optionally substituted by one or more substituent group independently selected from halo, cyano, nitro, —R$^{11}$, —OR$^{11}$, —SR$^{11}$, —SOR$^{11}$, —SO$_2$R$^{11}$, —COR$^{11}$, —CO$_2$R$^{11}$, —CONR$^{11}$R$^{12}$, —NR$^{11}$R$^{12}$, —NR$^{11}$COR$^{12}$, and —NR$^{11}$COCONR$^{12}$R$^{16}$;

each $R^3$, when present, is independently selected from halo, cyano, nitro, —R$^{13}$, —OR$^{13}$, —SR$^{13}$, —SOR$^{13}$, —SO$_2$R$^{13}$, —COR$^{13}$, —CO$_2$R$^{13}$, —CONR$^{13}$R$^{14}$, —NR$^{13}$R$^{14}$, —NR$^{13}$COR$^{14}$, —NR$^{13}$CO$_2$R$^{14}$ and —NR$^{13}$SO$_2$R$^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl) amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl) amino, carbamoyl, $C_{1-6}$alkylcarbamoyl and bis($C_{1-6}$alkyl) carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl) amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl) amino, carbamoyl, $C_{1-6}$alkylcarbamoyl and bis($C_{1-6}$alkyl) carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$ alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$ alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$ alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl) amino, carbamoyl, $C_{1-6}$alkylcarbamoyl and bis($C_{1-6}$alkyl) carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$ alkyl, $C_{1-6}$alkoxy$C_{1-6}$alkoxy, amino, $C_{1-6}$alkylamino, bis ($C_{1-6}$alkyl)amino, amino$C_{1-6}$alkyl, ($C_{1-6}$alkyl)amino$C_{1-6}$ alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis ($C_{1-6}$alkyl)sulfamoyl, $C_{1-6}$alkanoylamino, $C_{1-6}$alkanoyl ($C_{1-6}$alkyl)amino, carbamoyl, $C_{1-6}$alkylcarbamoyl and bis ($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituents selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with another aspect of the present invention, there is provided the use of a compound of formula (I)

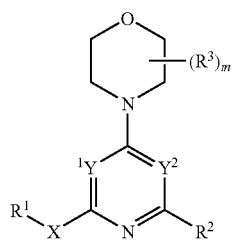

formula (I)

or a pharmaceutically acceptable salt; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7C$≡C—, —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$C(O)NR^4$—, —$NR^4C(O)$—, —$NR^4C(O)NR^5$—, —$S(O)_2NR^4$— and —$NR^4S(O)_2$—;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, —$R^9$, —$OR^9$, —$SR^9$, —$SOR^9$, —$SO_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and —$NR^9SO_2R^{10}$;

or X—$R^1$ is —$CR^6R^7OH$ $R^2$ is a group selected from $C_{1-6}$alkyl, carbocyclyl and heterocyclyl which group is substituted by —$NR^{17}CSNR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;

each $R^3$, when present, is independently selected from halo, cyano, nitro, —$R^{13}$, —$OR^{13}$, —$SR^{13}$, —$SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$R^{13}CO_2R^{14}$ and —$NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl in the manufacture of a medicament for use in the treatment of proliferative disease.

In accordance with a further aspect of the present invention, there is also provided a compound of formula (I)

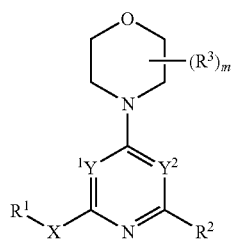

formula (I)

or a pharmaceutically acceptable salt thereof; wherein
m is 0, 1, 2, 3 or 4;
$^1Y$ and $Y^2$ are independently N or $CR^8$ provided that one of $^1Y$ and $Y^2$ is N and the other is $CR^8$;
X is a linker group selected from $—CR^4\!=\!CR^5—$, $—CR^4\!=\!CR^5CR^6R^7—$, $—CR^6R^7CR^5\!=\!CR^4$, $—C\!\equiv\!C—$, $—C\!\equiv\!CCR^6R^7—$, $—CR^6R^7C\!\equiv\!C—$, $—NR^4CR^6R^7—$, $—OCR^6R^7—$, $—SCR^6R^7—$, $—S(O)CR^6R^7—$, $—S(O)_2CR^6R^7—$, $—C(O)NR^4CR^6R^7—$, $—NR^4C(O)CR^6R^7—$, $—NR^4C(O)NR^5CR^6R^7—$, $—NR^4S(O)_2CR^6R^7—$, $—S(O)_2NR^4CR^6R^7—$, $—C(O)NR^4—$, $—NR^4C(O)—$, $—NR^4C(O)NR^5—$, $—(O)_2NR^4—$ and $—NR^4S(O)_2—$;
$R^1$ is a group selected from hydrogen, $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $—R^9$, $—OR^9$, $—SR^9$, $—SOR^9$, $—O_2R^9$, $—COR^9$, $—CO_2R^9$, $—CONR^9R^{10}$, $—NR^9R^{10}$, $—NR^9COR^{10}$, $—NR^9CO_2R^{10}$, $—NR^9CONR^{10}R^{15}$, $—NR^9COCONR^{10}R^{15}$ and $NR^9SO_2R^{10}$;
$R^2$ is a group selected from $C_{1-6}$alkyl, carbocyclyl and heterocyclyl which group is substituted by $—NR^{17}CSNR^{18}R^{19}$ and optionally substituted by one or more substituent group independently selected from halo, cyano, nitro, $—R^{11}$, $—OR^{11}$, $—SR^{11}$, $—SOR^{11}$, $—SO_2R^{11}$, $—COR^{11}$, $—CO_2R^{11}$, $—CONR^{11}R^{12}$, $—NR^{11}R^{12}$, $—NR^{11}R^{12}$, $—NR^{11}COR^{12}$, and $—NR^{11}COCONR^{12}R^{16}$;
each $R^3$, when present, is independently selected from halo, cyano, nitro, $—R^{13}$, $—OR^{13}$, $—R^{13}$, $^-SOR^{13}$, $—SO_2R^{13}$, $—COR^{13}$, $—CO_2R^{13}$, $—CONR^{13}R^{14}$, $—NR^{13}R^{14}$, $—NR^{13}COR^{14}$, $—NR^{13}CO2R^{14}$ and $—NR^{13}SO_2R^{14}$;
$R^4$ and $R^5$ are independently hydrogen or $C_{1-6}$alkyl;
or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^6$ and $R^7$ are independently selected from hydrogen, halo, cyano, nitro and $C_{1-6}$alkyl;
$R^8$ is selected from hydrogen, halo, cyano and $C_{1-6}$alkyl;
$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl) amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;
$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis ($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis ($C_{1-6}$alkyl)sulfamoyl, $C_{1-6}$alkanoylamino, $C_{1-6}$alkanoyl ($C_{1-6}$alkyl)amino, carbamoyl, $C_{1-6}$alkylcarbamoyl and bis ($C_{1-6}$alkyl)carbamoyl;
or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In accordance with a further aspect of the present invention, there is also provided a compound of formula (I)

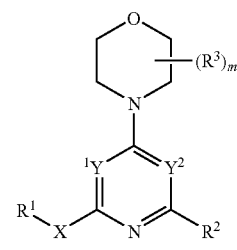

formula (I)

or a pharmaceutically acceptable salt thereof; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡$CCR^6R^7$—, —$CR^6R^7$C≡C—, —$NR^4CR^6R^7$—, —$OCR^6R^7$—, —$SCR^6R^7$—, —S(O)$CR^6R^7$—, —S(O)$_2CR^6R^7$—, —C(O)$NR^4CR^6R^7$—, —$NR^4$C(O)$CR^6R^7$—, —$NR^4$C(O)$NR^5CR^6R^7$—, —$NR^4$S(O)$_2CR^6R^7$—, —S(O)$_2NR^4CR^6R^7$—, —C(O)$NR^4$—, —$NR^4$C(O)$NR^5$—, —(O)$_2NR^4$— and —$NR^4$S(O)$_2$—;

$R^1$ is a group selected from $C_{1-6}$alkyl, $C_{2-6}$alkenyl, $C_{2-6}$alkynyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, —$R^9$, —$OR^9$, —$SR^9$, —$SOR^9$, —$O_2R^9$, —$COR^9$, —$CO_2R^9$, —$CONR^9R^{10}$, —$NR^9R^{10}$, —$NR^9COR^{10}$, —$NR^9CO_2R^{10}$, —$NR^9CONR^{10}R^{15}$, —$NR^9COCONR^{10}R^{15}$ and $NR^9SO_2R^{10}$;

or X—$R^1$ is —$CR^6R^7$OH;

$R^2$ is a group selected from $C_{1-6}$alkyl, carbocyclyl and heterocyclyl which group is substituted by —$NR^{17}CSNR^{18}R^{19}$ and optionally substituted by one or more substituent group independently selected from halo, cyano, nitro, —$R^{11}$, —$OR^{11}$, —$SR^{11}$, —$SOR^{11}$, —$SO_2R^{11}$, —$COR^{11}$, —$CO_2R^{11}$, —$CONR^{11}R^{12}$, —$NR^{11}R^{12}$, —$NR^{11}COR^{12}$, and —$NR^{11}COCONR^{12}R^{16}$;

each $R^3$, when present, is independently selected from halo, cyano, nitro, —$R^{13}$, —$OR^{13}$, —$R^{13}$, $^-SOR^{13}$, —$SO_2R^{13}$, —$COR^{13}$, —$CO_2R^{13}$, —$CONR^{13}R^{14}$, —$NR^{13}R^{14}$, —$NR^{13}COR^{14}$, —$NR^{13}CO2R^{14}$ and —$NR^{13}SO_2R^{14}$;

$R^4$ and $R^5$ are independently hydrogen or $C_{1-6}$alkyl;

or $R^1$ and $R^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{11}$, $R^{12}$, $R^{17}$ and $R^{18}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^{13}$, $R^{14}$, $R^{15}$, $R^{16}$ and $R^{19}$ are independently hydrogen or a group selected from $C_{1-6}$alkyl, carbocyclyl, carbocyclyl$C_{1-6}$alkyl, heterocyclyl and heterocyclyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In accordance with a further aspect of the present invention, there is also provided a compound of formula (I)

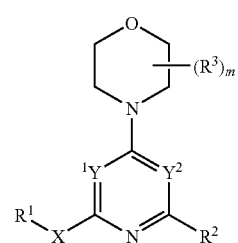

formula (I)

or a pharmaceutically acceptable salt thereof; wherein m is 0, 1, 2, 3 or 4;

$^1Y$ and $Y^2$ are independently N or $CR^8$ provided that one of $^1Y$ and $Y^2$ is N and the other is $CR^8$;

X is a linker group selected from —$CR^4$=$CR^5$—, —$CR^4$=$CR^5CR^6R^7$—, —$CR^6R^7CR^5$=$CR^4$—, —C≡C—, —C≡CCR$^6$R$^7$—, —CR$^6$R$^7$C≡C—, —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)NR$^5$CR$^6$R$^7$—, —S(O)$_2$NR$^4$CR$^6$R$^7$—, —C(O)NR$^4$—, —NR$^4$C(O)—, —NR$^4$C(O)NR$^5$—, —S(O)$_2$NR$^4$— and —NR$^4$S(O)$_2$—;

R$^1$ is a group selected from C$_{1-6}$alkyl, C$_{2-6}$alkenyl, C$_{2-6}$alkynyl, carbocyclyl, carbocyclylC$_{1-6}$alkyl, heterocyclyl and heterocyclylC$_{1-6}$alkyl, which group is optionally substituted by one or more substituent group selected from halo, cyano, nitro, —R$^9$, —OR$^9$, —SR$^9$, —SOR$^9$, —O$_2$R$^9$, —COR$^9$, —CO$_2$R$^9$, —CONR$^9$R$^{10}$, —NR$^9$R$^{10}$, —NR$^9$COR$^{10}$, —NR$^9$CO$_2$R$^{10}$, —NR$^9$CONR$^{10}$R$^{15}$, —NR$^9$COCONR$^{10}$R$^{15}$ and NR$^9$SO$_2$R$^{10}$;

or X—R$^1$ is —CR$^6$R$^7$OH;

R$^2$ is a group selected from C$_{1-6}$alkyl, carbocyclyl and heterocyclyl which group is substituted by —NR$^{17}$CSNR$^{18}$R$^{19}$ and optionally substituted by one or more substituent group independently selected from halo, cyano, nitro, —R$^{11}$, —OR$^{11}$, —SR$^{11}$, —SOR$^{11}$, —SO$_2$R$^{11}$, —COR$^{11}$, —CO$_2$R$^{11}$, —CONR$^{11}$R$^{12}$, —NR$^{11}$R$^{12}$, —NR$^{11}$COR$^{12}$, and —NR$^{11}$COCONR$^{12}$R$^{16}$;

each R$^3$, when present, is independently selected from halo, cyano, nitro, —R$^{13}$, —OR$^{13}$, —R$^{13}$, -SOR$^{13}$, —SO$_2$R$^{13}$, —COR$^{13}$, —CO$_2$R$^{13}$, —CONR$^{13}$R$^{14}$, —NR$^{13}$R$^{14}$, —NR$^{13}$COR$^{14}$, —NR$^{13}$CO2R$^{14}$ and —NR$^{13}$SO$_2$R$^{14}$;

R$^4$ and R$^5$ are independently hydrogen or C$_{1-6}$alkyl;

or R$^1$ and R$^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^6$ and R$^7$ are independently selected from hydrogen, halo, cyano, nitro and C$_{1-6}$alkyl;

R$^8$ is selected from hydrogen, halo, cyano and C$_{1-6}$alkyl;

R$^9$ and R$^{10}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^{11}$, R$^{12}$, R$^{17}$ and R$^{18}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^{13}$, R$^{14}$, R$^{15}$, R$^{16}$ and R$^{19}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

or R$^{18}$ and R$^{19}$ together with the nitrogen atom to which they are attached form a 3- to 10-membered heterocyclic ring wherein 1 or 2 ring carbon atoms is optionally replaced with N, O or S and which ring is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention. Solvates and mixtures thereof also form an aspect of the present invention. For example, a suitable solvate of a compound of formula (I) is, for example, a hydrate such as a hemi-hydrate, a mono-hydrate, a di-hydrate or a tri-hydrate or an alternative quantity thereof.

The present invention relates to the compounds of formula (I) as herein defined as well as to salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to furmarate, methanesulfonate, hydrochloride, hydrobromide, citrate and maleate salts and salts formed with phosphoric and sulfuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl, 1,3-dioxolen-2-onylmethyl esters for example 5-methyl-1,3-dioxolen-2-onylmethyl, and $C_{1-6}$alkoxycarbonyloxyethyl esters for example 1-methoxycarbonyloxyethyl; and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example formyl, acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$alkylaminoethyl)-N—$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^A C(O)OC_{1-6}$alkyl-CO—, wherein $R^A$ is for example, benzyloxy-$C_{1-4}$alkyl, or phenyl. Suitable substituents on a phenyl group in such esters include, for example, 4-$C_{1-4}$piperazino-$C_{1-4}$alkyl, piperazino-$C_{1-4}$alkyl and morpholino-$C_{1-4}$alkyl.

The compounds of the formula (I) may be also be administered in the form of a prodrug which is broken down in the human or animal body to give a compound of the formula (I). Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

In this specification the generic term "$C_{p-q}$alkyl" includes both straight-chain and branched-chain alkyl groups. However references to individual alkyl groups such as "propyl" are specific for the straight chain version only (i.e. n-propyl and isopropyl) and references to individual branched-chain alkyl groups such as "tert-butyl" are specific for the branched chain version only.

The prefix $C_{p-q}$ in $C_{p-q}$alkyl and other terms (where p and q are integers) indicates the range of carbon atoms that are present in the group, for example $C_{1-4}$alkyl includes $C_1$alkyl (methyl), $C_2$alkyl(ethyl), $C_3$alkyl (propyl as n-propyl and isopropyl) and $C_4$alkyl (n-butyl, sec-butyl, isobutyl and tert-butyl).

The term $C_{p-q}$alkoxy comprises —O—$C_{p-q}$alkyl groups.
The term $C_{p-q}$alkanoyl comprises —C(O)alkyl groups.
The term halo includes fluoro, chloro, bromo and iodo.

"Carbocyclyl" is a saturated, unsaturated or partially saturated monocyclic, bicyclic or tricyclic ring system containing from 3 to 14 ring atoms, wherein a ring $CH_2$ group may be replaced with a C=O group. "Carbocyclyl" includes "aryl", "$C_{p-q}$cycloalkyl" and "$C_{p-q}$cycloalkenyl".

"aryl" is an aromatic monocyclic, bicyclic or tricyclic carbcyclyl ring system.

"$C_{p-q}$cycloalkenyl" is an unsaturated or partially saturated monocyclic, bicyclic or tricyclic carbocyclyl ring system containing at least 1 C=C bond and wherein a ring $CH_2$ group may be replaced with a C=O group.

"$C_{p-q}$cycloalkyl" is a saturated monocyclic, bicyclic or tricyclic carbocyclyl ring system and wherein a ring $CH_2$ group may be replaced with a C=O group.

"Heterocyclyl" is a saturated, unsaturated or partially saturated monocyclic, bicyclic or tricyclic ring system containing from 3 to 14 ring atoms of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group. "Heterocyclyl" includes "heteroaryl", "cycloheteroalkyl" and "cycloheteroalkenyl".

"Heteroaryl" is an aromatic monocyclic, bicyclic or tricyclic heterocyclyl, particularly having 5 to 10 ring atoms, of which 1, 2, 3 or 4 ring atoms are chosen from nitrogen, sulfur or oxygen where a ring nitrogen or sulfur may be oxidised.

"Cycloheteroalkenyl" is an unsaturated or partially saturated monocyclic, bicyclic or tricyclic heterocyclyl ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

"Cycloheteroalkyl" is a saturated monocyclic, bicyclic or tricyclic heterocyclic ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

This specification may make use of composite terms to describe groups comprising more than one functionality. Unless otherwise described herein, such terms are to be interpreted as is understood in the art. For example carbocyclyl$C_{p-q}$ alkyl comprises $C_{p-q}$alkyl substituted by carbocyclyl, heterocyclyl$C_{p-q}$alkyl comprises $C_{p-q}$alkyl substituted by heterocyclyl, and bis($C_{p-q}$alkyl)amino comprises amino substituted by 2 $C_{p-q}$alkyl groups which may be the same or different.

Halo$C_{p-q}$alkyl is a $C_{p-q}$alkyl group that is substituted by 1 or more halo substituents and particuarly 1, 2 or 3 halo substituents. Similarly, other generic terms containing halo such as halo$C_{p-q}$alkoxy may contain 1 or more halo substituents and particluarly 1, 2 or 3 halo substituents.

Hydroxy$C_{p-q}$alkyl is a $C_{p-q}$alkyl group that is substituted by 1 or more hydroxyl substituents and particularly by 1, 2 or 3 hydroxy substituents. Similarly other generic terms containing hydroxy such as hydroxyC$_{p-q}$alkoxy may contain 1 or more and particularly 1, 2 or 3 hydroxy substituents.

C$_{p-q}$alkoxyC$_{p-q}$alkyl is a C$_{p-q}$alkyl group that is substituted by 1 or more C$_{p-q}$alkoxy substituents and particularly 1, 2 or 3 C$_{p-q}$alkoxy substituents. Similarly other generic terms containing C$_{p-q}$alkoxy such as C$_{p-q}$alkoxyC$_{p-q}$alkoxy may contain 1 or more C$_{p-q}$alkoxy substituents and particularly 1, 2 or 3 C$_{p-q}$alkoxy substituents.

Where optional substituents are chosen from "1 or 2", from "1, 2, or 3" or from "1, 2, 3 or 4" groups or substituents it is to be understood that this definition includes all substituents being chosen from one of the specified groups i.e. all substitutents being the same or the substituents being chosen from two or more of the specified groups i.e. the substitutents not being the same.

Compounds of the present invention have been named with the aid of computer software (ACD/Name version 8.0).

"Proliferative disease(s)" includes malignant disease(s) such as cancer as well as non-malignant disease(s) such as inflammatory diseases, obstrucutive airways diseases, immune diseases or cardiovascular diseases.

Suitable values for any R group or any part or substitutent for such groups include:

In one aspect of the invention $^1$Y is N and Y$^2$ is CR$^8$.
In another aspect $^1$Y is N and Y$^2$ is CH.
In yet another aspect $^1$Y is CR$^8$ and Y$^2$ is N.
In a further aspect $^1$Y is CH or CF and Y$^2$ is N.
In yet a further aspect $^1$Y is CH and Y$^2$ is N.
X
In one aspect of the invention X is a linker group selected from —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)NR$^5$CR$^6$R$^7$—, —S(O)$_2$NR$^4$CR$^6$R$^7$—, —NR$^4$C(O)—, —C(O)NR$^4$—, —S(O)$_2$NR$^4$— and —NR$^4$S(O)$_2$—.

In another aspect X is a linker group selected from —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —N$^4$C(O)NR$^5$CR$^6$R$^7$—, —S(O)$_2$NR$^4$CR$^6$R$^7$, —C(O)NR$^4$— and —NR$^4$C(O)—.

In a further aspect X is a linker group selected from —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$—, and —NR$^4$C(O)—.

In a further aspect X is a linker group selected from —NR$^4$CR$^6$R$^7$—, —OCR$^6$R$^7$—, —SCR$^6$R$^7$—, —S(O)CR$^6$R$^7$— and —S(O)$_2$CR$^6$R$^7$—.

| | |
|---|---|
| for C$_{1-4}$alkyl: | methyl, ethyl, propyl, butyl, 2-methylpropyl and tert-butyl; |
| for C$_{1-6}$alkyl: | C$_{1-4}$alkyl, pentyl, 2,2-dimethylpropyl, 3-methylbutyl and hexyl; |
| for C$_{3-6}$cycloalkyl: | cyclopropyl, cyclobutyl, cyclopentyl and cyclohexyl; |
| for C$_{3-6}$cycloalkylC$_{1-4}$alkyl: | cyclopropylmethyl, cyclopropylethyl, cyclobutylmethyl, cyclopentylmethyl and cyclohexylmethyl; |
| for aryl: | phenyl and naphthyl; |
| for arylC$_{1-4}$alkyl: | benzyl, phenethyl, naphthylmethyl and naphthylethyl; |
| for carbocylyl: | aryl, cyclohexenyl and C$_{3-6}$cycloalkyl; |
| for halo: | fluoro, chloro, bromo and iodo; |
| for C$_{1-4}$alkoxy: | methoxy, ethoxy, propoxy and isopropoxy; |
| for C$_{1-6}$alkoxy: | C$_{1-4}$alkoxy, pentyloxy, 1-ethylpropoxy and hexyloxy; |
| for C$_{1-6}$alkanoyl: | acetyl, propanoyl and 2-methylpropanoyl; |
| for heteroaryl: | pyridyl, imidazolyl, quinolinyl, cinnolyl, pyrimidinyl, thienyl, pyrrolyl, pyrazolyl, thiazolyl, thiazolyl, triazolyl, oxazolyl, isoxazolyl, furanyl, pyridazinyl, pyrazinyl, indolyl, benzofuranyl, dibenzofuranyl and benzothienyl; |
| for heteroarylC$_{1-4}$alkyl: | pyrrolylmethyl, pyrrolylethyl, imidazolylmethyl, imidazolylethyl, pyrazolylmethyl, pyrazolylethyl, furanylmethyl, furanylethyl, thienylmethyl, theinylethyl, pyridylmethyl, pyridylethyl, pyrazinylmethyl, pyrazinylethyl, pyrimidinylmethyl, pyrimidinylethyl, pyrimidinylpropyl, pyrimidinylbutyl, imidazolylpropyl, imidazolylbutyl, quinolinylpropyl, 1,3,4-triazolylpropyl and oxazolylmethyl; |
| for heterocyclyl: | heteroaryl, pyrrolidinyl, isoquinolinyl, quinoxalinyl, benzothiazolyl, benzoxazolyl, piperidinyl, piperazinyl, azetidinyl, morpholinyl, tetrahydroisoquinolinyl, tetrahydroquinolinyl, indolinyl, dihydro-2H-pyranyl and tetrahydrofuranyl. |

It should be noted that examples given for terms used in the description are not limiting.

Particular values of m, X, $^1$Y and Y$^2$, X, R$^1$, X—R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{17}$, R$^{18}$ and R$^{19}$ are as follows. Such values may be used individually or in combination where appropriate, in connection with any aspect of the invention, or part thereof, and with any of the definitions, claims or embodiments defined herein.

m
In one aspect of the invention m is 0, 1, 2 or 3.
In another aspect m is 0, 1 or 2.
In a further aspect m is 0 or 1.
In yet another aspect m is 0 so that R$^3$ is absent.
In yet another aspect m is 1 and R$^3$ is methyl.
$^1$Y and Y$^2$ In yet another aspect X is a linker group selected from —SCR$^6$R$^7$—, —S(O)CR$^6$R$^7$— and —S(O)$_2$CR$^6$R$^7$—.

In another aspect X is a linker group selected from —NR$^4$CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)—, —S(O)$_2$C(CH$_3$)$_2$—, —C(O)NR$^4$— and —NR$^4$C(O)—.

In another aspect X is a linker group selected from —NR$^4$CH$_2$—, —OCH$_2$—, —SCH$_2$—, —S(O)CH$_2$—, —S(O)$_2$CH$_2$—, —C(O)NR$^4$—, and —NR$^4$C(O)—.

In another aspect X is a linker group selected from —NR$^4$CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)— and —S(O)$_2$C(CH$_3$)$_2$—.

In another aspect X is a linker group selected from —NR$^4$CH$_2$—, —OCH$_2$—, —SCH$_2$—, —S(O)CH$_2$— and —S(O)$_2$CH$_2$—.

In a further aspect X is a linker group selected from —NHCH$_2$—, —N(CH$_3$)CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)—, —S(O)$_2$C(CH$_3$)$_2$—, —C(O)NH—, —C(O)N(CH$_3$)—, —NHC(O)— and —N(CH$_3$)C(O)—.

In a further aspect X is a linker group selected from —NHCH$_2$—, —N(CH$_3$)CH$_2$—, —OCH$_2$—, —SCH$_2$—, —S(O)CH$_2$—, —S(O)$_2$CH$_2$—, —C(O)NH—, —C(O)N(CH$_3$)—, —NHC(O)— and —N(CH$_3$)C(O)—.

In yet a further aspect X is a linker group selected from —NHCH$_2$—, —N(CH$_3$)CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)— and —S(O)$_2$C(CH$_3$)$_2$—.

In yet a further aspect X is a linker group selected from —NHCH$_2$—, —N(CH$_3$)CH$_2$—, —OCH$_2$—, —SCH$_2$— and —S(O)$_2$CH$_2$—.

In another aspect X is —SCH$_2$— or —S(O)$_2$CH$_2$—.

In another aspect X is —SCH$_2$—, —SCH(CH$_3$)— or —SC(CH$_3$)$_2$—.

In another aspect X is —S(O)CH$_2$—, —S(O)CH(CH$_3$)— or —S(O)C(CH$_3$)$_2$—.

In another aspect X is —S(O)$_2$CH$_2$—, —S(O)$_2$CH(CH$_3$)— or —S(O)$_2$C(CH$_3$)$_2$—.

In another aspect X is —S(O)$_2$CH$_2$—.

In another aspect X is —S(O)$_2$C(CH$_3$)$_2$—.

$R^1$

In one aspect of the invention $R^1$ is a group selected from C$_{1-4}$alkyl, C$_{3-10}$cycloalkyl, aryl, C$_{3-10}$cycloalkylC$_{1-4}$alkyl, arylC$_{1-4}$alkyl, cycloheteroalkyl, heteroaryl, cycloheteroalkylC$_{1-4}$alkyl, heteroarylC$_{1-4}$alkyl, which group is optionally substituted by one or more substituent group selected from halo, cyano, nitro, $R^9$, —OR$^9$, —COR$^9$, —CONR$^9$R$^{10}$, —NR$^9$R$^{10}$ and —NR$^9$COR$^{10}$.

In another aspect, $R^1$ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —OR$^9$, —COR$^9$, —CONR$^9$R$^{10}$, —NR$^9$R$^{10}$ and —NR$^9$COR$^{10}$.

In a further aspect, $R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$.

In yet another aspect $R^1$ is a group selected from methyl, isopropyl, cyclopropyl, cyclohexyl, —CH$_2$CH$_2$OH, —, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrolidin-3-yl-thiazol-2-yl, 4-methylthiazol-2-yl, and 3-methyl-1,3,4-thiadiazol-2-yl.

In yet another aspect $R^1$ is a group selected from methyl, —CH$_2$CH$_2$OH and phenyl.

In yet another aspect $R^1$ is a group selected from methyl and phenyl.

In yet another aspect $R^1$ is methyl.

In yet another aspect $R^1$ is —CH$_2$CH$_2$OH.

In yet another aspect $R^1$ is phenyl.

X—$R^1$

In one embodiment X—$R^1$ is —C(CH$_3$)$_2$OH or —CH$_2$OH.

In one embodiment X—$R^1$ is —CH$_2$OH.

In one embodiment X—$R^1$ is —C(CH$_3$)$_2$OH.

$R^2$

In one aspect of the invention $R^2$ is selected from carbocyclyl or heterocyclyl which group is substituted by —NR$^{17}$CSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from carbocyclyl or heterocyclyl which group is substituted by —NHCSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from carbocyclyl or heterocyclyl which group is substituted by —NHCSNHR$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from 5 or 6 membered carbocyclyl or heterocyclyl which group is substituted by —NR$^{17}$CSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from 5 or 6 membered carbocyclyl or heterocyclyl which group is substituted by —NHCSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from 5 or 6 membered carbocyclyl or heterocyclyl which group is substituted by —NHCSNHR$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from a 6 membered aryl and 5 or 6 membered heteroaryl which group is substituted by —NR$^{17}$CSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention $R^2$ is selected from a 6 membered aryl and 5 or 6 membered heteroaryl which group is substituted by —NHCSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$.

In one aspect of the invention R² is selected from a 6 membered aryl and 5 or 6 membered heteroaryl which group is substituted by —NHCSNHR¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹².

In another aspect R² is selected from phenyl, pyrrolyl, imidazolyl, pyrazolyl, furanyl, thienyl, pyridinyl, pyrimidinyl, pyridazinyl, thiazolyl, which group is substituted by —NR¹⁷CSNR¹⁸R¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹².

In another aspect R² is selected from phenyl, pyrrolyl, imidazolyl, pyrazolyl, furanyl, thienyl, pyridinyl, pyrimidinyl, pyridazinyl, thiazolyl which group is substituted by —NHCSNR¹⁸R¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹².

In another aspect R² is selected from phenyl, pyrrolyl, imidazolyl, pyrazolyl, furanyl, thienyl, pyridinyl, pyrimidinyl, pyridazinyl, thiazolyl which group is substituted by —NHCSNHR¹⁹ and optionally substituted by one or more substituent group independently selected from halo, cyano, nitro, —R¹¹, —OR¹¹, —COR¹¹, —CONR¹¹R¹², —NR¹¹R¹² and —NR¹¹COR¹².

In another aspect R² is selected from phenyl, pyrrolyl, imidazolyl, pyrazolyl, furanyl, thienyl, pyridinyl, pyrimidinyl, pyridazinyl, thiazolyl which group is substituted by —NR¹⁷CSNR¹⁸R¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is selected from phenyl, pyrrolyl, imidazolyl, pyrazolyl, furanyl, thienyl, pyridinyl, pyrimidinyl, pyridazinyl, thiazolyl which group is substituted by —NHCSNR¹⁸R¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is selected from phenyl, pyrrolyl, imidazolyl, pyrazolyl, furanyl, thienyl, pyridinyl, pyrimidinyl, pyridazinyl, thiazolyl which group is substituted by —NHCSNHR¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is phenyl or pyridylsubstituted by —NR¹⁷CSNR¹⁸R¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is phenyl or pyridyl substituted by —NHCSNR¹⁸R¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is phenyl or pyridyl substituted by —NHCSNHR¹⁹ and optionally substituted by one or more substituent group independently selected from fluoro, methyl, methoxy, hydroxymethyl, cyanomethyl, —CONH₂, —CONHCH₃ and —CON(CH₃)₂.

In another aspect R² is phenyl or pyridyl optionally substituted by —NR¹⁷CSNR¹⁸R¹⁹.

In another aspect R² is phenyl or pyridyl optionally substituted by —NHCSNR¹⁸R¹⁹.

In another aspect R² is phenyl or pyridyl optionally substituted by —NHCSNHR¹⁹.

In another aspect R² is

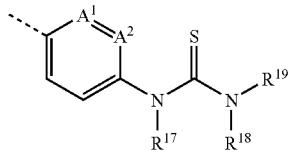

wherein A¹ and A² are selected from CH or N provided that at least one of A¹ or A² is CH.

In another aspect R² is

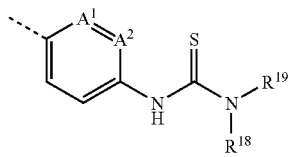

wherein A¹ and A² are selected from CH or N provided that at least one of A¹ or A² is CH.

In another aspect R² is

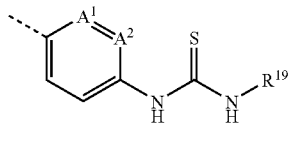

wherein A¹ and A² are selected from CH or N provided that at least one of A¹ or A² is CH.

In another aspect R² is

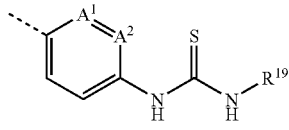

wherein A¹ and A² are CH.

R⁴

In one aspect of the invention R⁴ is hydrogen or methyl.

In another aspect R⁴ is hydrogen.

R⁴ and R¹

In another aspect of the invention, when X is —NR⁴CR⁶R⁷—, —NR⁴C(O)CR⁶R⁷—, —NR⁴C(O)NR⁵CR⁶R⁷—, —NR⁴S(O)₂CR⁶R⁷—, —NR⁴C(O)—, —NR⁴C(O)NR⁵— or —NR⁴S(O)₂—, R¹ and R⁴ together with the atom or atoms to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, C₁₋₆alkyl, C₁₋₆alkoxy, haloC₁₋₆alkyl, haloC₁₋₆alkoxy, hydroxyC₁₋₆alkyl, hydroxyC₁₋₆alkoxy, C₁₋₆alkoxyC₁₋₆alkyl, C₁₋₆alkoxyC₁₋₆alkoxy, amino, C₁₋₆alkylamino, bis(C₁₋₆alkyl)amino, aminoC₁₋₆alkyl, (C₁₋₆alkyl)aminoC₁₋₆alkyl, bis(C₁₋₆alkyl)aminoC₁₋₆alkyl, cyanoC₁₋₆alkyl, C₁₋₆alkylsulfonyl, C₁₋₆alkylsulfonylamino, C₁₋₆alkylsulfonyl(C₁₋₆alkyl)

amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —$NR^4CR^6R^7$—, —$NR^4C(O)CR^6R^7$—, —$NR^4C(O)NR^5CR^6R^7$—, —$NR^4S(O)_2CR^6R^7$—, —$NR^4C(O)$—, —$NR^4C(O)NR^5$— or —$NR^4S(O)_2$—, $R^1$ and $R^4$ together with the atom or atoms to which they are attached form a 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention, when X is —$NR^4CR^6R^7$—, —$NR^4C(O)CR^6R^7$—, —$NR^4C(O)NR^5CR^6R^7$—, —$NR^4S(O)_2CR^6R^7$—, —$NR^4C(O)$—, —$NR^4C(O)NR^5$— or —$NR^4S(O)_2$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

$R^5$

In one aspect of the invention $R^5$ is hydrogen or methyl.
In another aspect $R^5$ is hydrogen.
In another aspect $R^5$ is methyl.

$R^6$

In one aspect of the invention $R^6$ is hydrogen or methyl.
In another aspect $R^6$ is hydrogen.
In another aspect $R^6$ is methyl.

$R^7$

In one aspect of the invention $R^7$ is hydrogen or methyl.
In another aspect $R^7$ is hydrogen.
In another aspect $R^7$ is methyl.

$R^8$

In one aspect of the invention $R^8$ is hydrogen or halo.
In another aspect $R^8$ is hydrogen or fluoro.
In a further aspect $R^8$ is hydrogen.

$R^9$

In one aspect of the invention $R^9$ is hydrogen or $C_{1-4}$alkyl optionally substituted by 1, 2 or 3 substituent groups selected from halo, cyano, nitro, hydroxy, $C_{1-4}$alkoxy, amino, $C_{1-4}$alkylamino and bis($C_{1-4}$alkyl)amino.
In another aspect $R^9$ is hydrogen or $C_{1-4}$alkyl optionally substituted by 1, 2 or 3 halo substituents.
In a further aspect $R^9$ is hydrogen, methyl or trifluoromethyl.

$R^{10}$

In one aspect of the invention $R^{10}$ is hydrogen.

$R^{11}$

In one aspect of the invention $R^{11}$ is hydrogen or a group selected from $C_{1-4}$alkyl, aryl and cycloheteroalkyl which group is optionally substituted by 1, 2 or 3 groups selected from halo, hydroxy and cyano.
In another aspect $R^{11}$ is hydrogen, methyl optionally substituted with hydroxy or cyano, phenyl or pyrrolidinyl.
In another aspect $R^{11}$ is hydrogen or methyl.

$R^{12}$

In one aspect of the invention $R^{12}$ is hydrogen or methyl.

$R^{17}$

In one aspect of the invention $R^{17}$ is hydrogen or a group selected from $C_{1-4}$alkyl, aryl and cycloheteroalkyl which group is optionally substituted by 1, 2 or 3 groups selected from halo, hydroxy and cyano.
In another aspect $R^{17}$ is hydrogen, methyl optionally substituted with hydroxy or cyano, phenyl or pyrrolidinyl.
In another aspect $R^{17}$ is hydrogen or methyl.
In another aspect $R^{17}$ is hydrogen.

$R^{18}$

In one aspect of the invention $R^{18}$ is hydrogen or methyl.
In one aspect of the invention $R^{18}$ is hydrogen $R^{19}$ In one aspect of the invention $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from $C_{1-6}$alkyl, $C_{3-6}$cycloakyl, phenyl, naphthyl, pyrrolyl, imidazolyl, isoxazolyl, pyrazolyl, furanyl, thienyl, pyridinyl, pyrimidinyl, pyridazinyl, azaindolyl, indolyl, quinolinyl, benzimidazolyl, benzofuranyl, dibenzofuranyl, benzothienyl, phenyl$C_{1-6}$alkyl, naphthyl$C_{1-6}$alkyl, pyrrolyl$C_{1-6}$alkyl, imidazolyl$C_{1-6}$alkyl, isoxazolyl$C_{1-6}$alkyl, pyrazolyl$C_{1-6}$alkyl, furanyl$C_{1-6}$alkyl, thienyl$C_{1-6}$alkyl, pyridinyl$C_{1-6}$alkyl, pyrimidinyl$C_{1-6}$alkyl, pyridazinyl$C_{1-6}$alkyl, azaindolyl$C_{1-6}$alkyl, indolyl$C_{1-6}$alkyl, quinolinyl$C_{1-6}$alkyl, benzimidazolyl$C_{1-6}$alkyl, benzofuranyl$C_{1-6}$alkyl, dibenzofuranyl$C_{1-6}$alkyl, benzothienyl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyridinyl and pyrimidinyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —$CH_2$(cyclopropyl), —$CH_2CH_2NMe_2$, —$CH(CH_3)CH_2OH$, —$C(CH_3)_2CH_2OH$, —$CH_2CH_2OH$, —$CH_2CH_2CH_2OH$, 4-methylphenyl, 4-chlorophenyl, 4-trifluoromethylphenyl, 4-flurophenyl, 4-methoxyphenyl, 3,4-difluorophenyl, phenyl, thien-2-yl, —$CH_2$(imidazol-2-yl), —$CH_2$(imidazol-3-yl), isoxazolyl-3-yl, 6-oxo-1H-pryrdin-2-yl, 5-methylisoxazol-3-yl, —$CH_2$(1-methylpyrazol-4-yl), 1-methylpyrazol-4-yl, 6-methoxypryridin-3-yl, 5-fluoropyridin-2-yl, pyrimidin-2-yl, and 1H-pyrazol-3-yl.

In one aspect of the invention $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —$CH_2$(cyclopropyl), —$CH_2CH_2NMe_2$, —$CH(CH_3)CH_2OH$, —$C(CH_3)_2CH_2OH$, —$CH_2CH_2OH$, —$CH_2CH_2CH_2OH$, 4-methylphenyl, 4-chlorophenyl, 4-trifluoromethylphenyl, 4-flurophenyl, 4-methoxyphenyl, 3,4-difluorophenyl, thien-2-yl, —$CH_2$(imidazol-2-yl), —$CH_2$(imidazol-3-yl), isoxazolyl-3-yl, 6-oxo-1H-pryrdin-2-yl, 5-methylisoxazol-3-yl, —$CH_2$(1-methylpyrazol-4-yl), 1-methylpyrazol-4-yl, 6-methoxypryridin-3-yl, 5-fluoropyridin-2-yl, pyrimidin-2-yl, and 1H-pyrazol-3-yl.

In one aspect of the invention $R^{19}$ is a group selected from methyl, ethyl, cyclopropyl, —$CH_2CH_2NMe_2$, —$CH_2CH_2OH$, 4-fluorophenyl, 4-methoxyphenyl, and phenyl.

In one aspect of the invention $R^{19}$ is hydrogen or a group selected from ethyl, cyclopropyl, 4-fluorophenyl, 4-methoxyphenyl, and phenyl.

In one aspect of the invention $R^{19}$ is —$CH_2CH_2OH$.

$R^{18}$ and $R^{19}$

In one aspect of the invention, $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one aspect of the invention, $R^{18}$ and $R^{19}$ together with the nitrogen atom to which they are attached form a morpholine ring.

In one aspect of the invention there is provided a subset of compounds of formula (I), or a pharmaceutically acceptable salt thereof;

m is 0, 1 or 2;

$Y^1$ and $Y^2$ are independently N or $CR^8$ provided that one of $Y^1$ and $Y^2$ is N and the other is $CR^8$;

X is a linker group selected from —$NR^4CR^6R^7$—, —$OCR^6R^7$—, —$SCR^6R^7$—, —$S(O)CR^6R^7$—, —$S(O)_2CR^6R^7$—, —$C(O)NR^4CR^6R^7$—, —$NR^4C(O)NR^5CR^6R^7$—, —$S(O)_2NR^4CR^6R^7$—, —$NR^4C(O)$—, —$S(O)_2NR^4$— and —$NR^4S(O)_2$—;

$R^1$ is a group selected from $C_{1-6}$alkyl, carbocyclyl, carbocyclyl$C_{1-6}$alkyl, heterocyclyl and heterocyclyl$C_{1-6}$alkyl, which group is optionally substituted by one or more substituent group selected from halo, cyano, nitro, $R^9$, —$OR^9$, —$COR^9$, —$CONR^9R^{10}$, —$NR^9R^{10}$ and —$NR^9COR^{10}$;

or X—$R^1$ is —$C(CH_3)_2OH$ or —$CH_2OH$;

$R^2$ is selected from aryl and heteroaryl which group is substituted by —$NR^{17}CSNR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

each $R^3$, when present, is methyl;

$R^4$ and $R^5$ are independently hydrogen or $C_{1-6}$alkyl;

or, when X is —$NR^4CR^6R^7$—, —$NR^4C(O)NR^5CR^6R^7$—, —$NR^4C(O)$— or —$NR^4S(O)_2$—, $R^1$ and $R^4$ together with the atom or atoms to which they are attached form a 5-, 6- or 7-membered heterocyclic ring wherein 1 ring carbon atom is optionally replaced with N or O and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; $R^6$ and $R^7$ are independently selected from hydrogen, halo, cyano, nitro and $C_{1-6}$alkyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$, $R^{17}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another aspect of the invention there is provided a subset of compounds of formula (I), or a pharmaceutically acceptable salt thereof;

m is 0, 1 or 2;

$^1Y$ and $Y^2$ are independently N or $CR^8$ provided that one of $^1Y$ and $Y^2$ is N and the other is $CR^8$;

X is a linker group selected from —$NR^4CH_2$—, —$OCH_2$—, —$OCH(CH_3)$—, —$OC(CH_3)_2$—, —$SCH_2$—, —$SCH(CH_3)$—, —$SC(CH_3)_2$—, —$S(O)CH_2$—, —$S(O)CH(CH_3)$—, —$S(O)C(CH_3)_2$—, —$S(O)_2CH_2$—, —$S(O)_2CH(CH_3)$—, —$S(O)_2C(CH_3)_2$—, —$C(O)NR^4$— and —$NR^4C(O)$—;

$R^1$ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, $R^9$, —$OR^9$, —$COR^9$, —$CONR^9R^{10}$, —$NR^9R^{10}$ and —$NR^9COR^{10}$;

or X—$R^1$ is —$C(CH_3)_2OH$ or —$CH_2OH$;

$R^2$ is selected from 5 or 6 membered aryl and heteroaryl which group is substituted by —$NHCSNR^{18}R^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

each $R^3$, when present, is methyl;

$R^4$ is hydrogen or $C_{1-6}$alkyl;

or, when X is —$NR^4CH_2$— or —$NR^4C(O)$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (I), or a pharmaceutically acceptable salt thereof;

m is 0 or 1;

$^1Y$ is CH and $Y^2$ is N;

X is a linker group selected from —$S(O)_2CH_2$—, —$S(O)_2CH(CH_3)$— and —$S(O)_2C(CH_3)_2$—;

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NHCOCH_3$, —$CONH_2$ and —$CONHCH_3$;

or —$XR^1$ is —$C(CH_3)_2OH$ or —$CH_2OH$;

$R^2$ is selected from phenyl, pyrrolyl, imidazolyl, pyrazolyl, furanyl, thienyl, pyridinyl, pyrimidinyl, pyridazinyl, thiazolyl which group is substituted by —$NHCSNHR^{19}$ and optionally substituted by one or more substituent group independently selected from halo, cyano nitro —$R^{11}$, —$OR^{11}$, —$COR^{11}$, —$CONR^{11}R^{12}$, —$NR^{11}R^{12}$ and —$NR^{11}COR^{12}$;

$R^3$, when present, is methyl;

$R^{11}$, $R^{12}$ and $R^{18}$ are independent hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In a further particular class of compound of formula (I), or a pharmaceutically acceptable salt thereof;

m is 1;

X is a linker group selected from —$S(O)_2CH_2$—, —$S(O)_2CH(CH_3)$— and —$S(O)_2C(CH_3)_2$—;

$^1Y$ is CH and $Y^2$ is N.

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NHCOCH_3$, —$CONH_2$ and —$CONHCH_3$;

$R^2$ is phenyl or pyridyl substituted by —$NHCSNHR^{19}$ and optionally substituted by one or more substituent group independently selected from fluoro, methyl, methoxy, hydroxymethyl, cyanomethyl, —$CONH_2$, —$CONHCH_3$ and —$CON(CH_3)_2$;

$R^3$ is methyl; and $R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyridinyl and pyrimidinyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In a further particular class of compound of formula (I), or a pharmaceutically acceptable salt thereof;

m is 1;

X is a linker group selected from —$S(O)_2CH_2$—, —$S(O)_2CH(CH_3)$— and —$S(O)_2C(CH_3)_2$—;

$^1Y$ is CH and $Y^2$ is N.

$R^1$ is a group selected from methyl, isopropyl, cyclopropyl, cyclohexyl, —$CH_2CH_2OH$, —, —$CH_2CH_2NC(O)CH_3$, —$CH_2CONH_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrolidin-3-yl, thiazol-2-yl, 4-methylthiazol-2-yl, and 3-methyl-1,3,4-thiadiazol-2-yl;

$R^2$ is

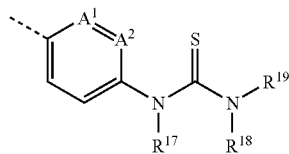

wherein $A^1$ and $A^2$ are selected from CH or N provided that at least one of $A^1$ or $A^2$ is CH;

$R^{17}$ is hydrogen;

$R^{18}$ is hydrogen;

$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —$CH_2$(cyclopropyl), —$CH_2CH_2NMe_2$, —$CH(CH_3)CH_2OH$, —$C(CH_3)_2CH_2OH$, —$CH_2CH_2OH$, —$CH_2CH_2CH_2OH$, 4-methylphenyl, 4-chlorophenyl, 4-trifluoromethylphenyl, 4-flurophenyl, 4-methoxyphenyl, 3,4-difluorophenyl, thien-2-yl, —$CH_2$(imidazol-2-yl), —$CH_2$(imidazol-3-yl), isoxazolyl-3-yl, 6-oxo-1H-pryrdin-2-yl, 5-methylisoxazol-3-yl, 1-methylpyrazol-4-yl, —$CH_2$(1-methylpyrazol-4-yl), 6-methoxypryridin-3-yl, 5-fluoropyridin-2-yl, pyrimidin-2-yl, and 1H-pyrazol-3-yl;

and, $R^3$ is methyl.

In one aspect of the invention there is provided a subset of compounds of formula (Ia) or (Ib)

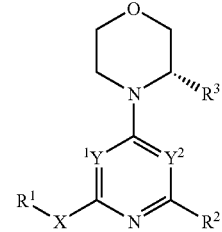

(Ia)

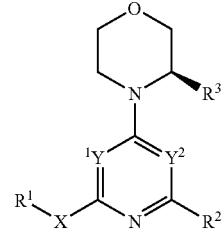

(Ib)

or a pharmaceutically acceptable salt thereof;

$^1Y$ and $Y^2$ are independently N or $CR^8$ provided that one of $^1Y$ and $Y^2$ is N and the other is $CR^8$;

X is a linker group selected from —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)NR$^5$CR$^6$R$^7$—, —S(O)$_2$NR$^4$CR$^6$R$^7$—, —NR$^4$C(O)—, —S(O)$_2$NR$^4$— and —NR$^4$S(O)$_2$—;

R$^1$ is a group selected from C$_{1-6}$alkyl, carbocyclyl, carbocyclylC$_{1-6}$alkyl, heterocyclyl and heterocyclylC$_{1-6}$alkyl, which group is optionally substituted by one or more substituent group selected from halo, cyano, nitro, R$^9$, —OR$^9$, —COR$^9$, —CONR$^9$R$^{10}$, —NR$^9$R$^{10}$ and —NR$^9$COR$^{10}$;

or X—R$^1$ is —C(CH$_3$)$_2$OH or —CH$_2$OH;

R$^2$ is selected from aryl and heteroaryl which group is substituted by —NR$^{17}$CSNR$^{18}$R$^{19}$ and optionally substituted by one or more substituent group independently selected from halo, cyano, nitro, —R$^{11}$, —OR$^{11}$, —COR$^{11}$, —CONR$^{11}$R$^{12}$, —NR$^{11}$R$^{12}$ and —NR$^{11}$COR$^{12}$;

R$^3$ is methyl;

R$^4$ and R$^5$ are independently hydrogen or C$_{1-6}$alkyl or, when X is —NR$^4$CR$^6$R$^7$—, —NR$^4$C(O)NR$^5$CR$^6$R$^7$—, —NR$^4$C(O)— or —NR$^4$S(O)$_2$—, R$^1$ and R$^4$ together with the atom or atoms to which they are attached form a 5-, 6- or 7-membered heterocyclic ring wherein 1 ring carbon atom is optionally replaced with N or O and which ring is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^6$ and R$^7$ are independently selected from hydrogen, halo, cyano, nitro and C$_{1-6}$alkyl;

R$^8$ is selected from hydrogen, halo, cyano and C$_{1-6}$alkyl;

R$^9$ and R$^{10}$ are independently hydrogen or a group selected from C$_{1-6}$alkyl, carbocyclyl and heterocyclyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino and bis(C$_{1-6}$alkyl)amino;

R$^{11}$, R$^{12}$, R$^{17}$ and R$^{18}$ are independently hydrogen or a group selected from C$_{1-6}$alkyl, carbocyclyl and heterocyclyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino and bis(C$_{1-6}$alkyl)amino; and R$^{19}$ is hydrogen or a group selected from C$_{1-6}$alkyl, C$_{3-6}$cycloakyl, aryl, heteroaryl, arylC$_{1-6}$alkyl and heteroarylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

or R$^{18}$ and R$^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In another aspect of the invention there is provided a subset of compounds of formula (Ia) or (Ib)

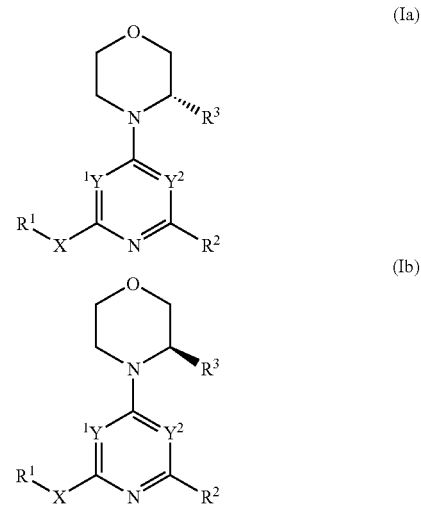

or a pharmaceutically acceptable salt thereof;

$^1$Y and Y$^2$ are independently N or CR$^8$ provided that one of $^1$Y and Y$^2$ is N and the other is CR$^8$;

X is a linker group selected from —NR$^4$CH$_2$—, —OCH$_2$—, —OCH(CH$_3$)—, —OC(CH$_3$)$_2$—, —SCH$_2$—, —SCH(CH$_3$)—, —SC(CH$_3$)$_2$—, —S(O)CH$_2$—, —S(O)CH(CH$_3$)—, —S(O)C(CH$_3$)$_2$—, —S(O)$_2$CH$_2$—, —S(O)$_2$CH(CH$_3$)—, —S(O)$_2$C(CH$_3$)$_2$—, —C(O)NR$^4$— and —NR$^4$C(O)—;

R$^1$ is a group selected from adamantyl, methyl, ethyl, propyl, butyl, isobutyl, tert-butyl, cyclopentyl, cyclohexyl, phenyl, benzyl, phenethyl, pyrrolidinyl, pyrrolyl, imidazolyl, pyrazolyl, furanyl, thienyl, pyridinyl, pyrimidinyl, pyrazinyl, pyrrolidinylmethyl, pyrrolidinylethyl, pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridinylmethyl, pyridinylethyl, pyrimidinylmethyl, pyrimidinylethyl, pyrazinylmethyl and pyrazinylethyl, which group is optionally substituted by 1, 2 or 3 substituent group selected from halo, cyano, nitro, R$^9$, —OR$^9$, —COR$^9$, —CONR$^9$R$^{10}$, —NR$^9$R$^{10}$ and —NR$^9$COR$^{10}$;

or X—R$^1$ is —C(CH$_3$)$_2$OH or —CH$_2$OH;

R$^2$ is selected from 5 or 6 membered aryl and heteroaryl which group is substituted by —NHCSNR$^{18}$R$^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

$R^3$ is methyl;

$R^4$ is hydrogen or $C_{1-6}$alkyl;

or, when X is —$NR^4CH_2$— or —$NR^4C(O)$—, $R^1$ and $R^4$ together with the atom or atoms to which they are attached form a 5- or 6-membered heterocyclic ring wherein 1 ring carbon atom is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^8$ is selected from hydrogen, halo, cyano and $C_{1-6}$alkyl;

$R^9$ and $R^{10}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

or $R^{18}$ and $R^{19}$ together with the nitrogen atom to which they are attached form a 6-membered heterocyclic ring wherein 1 ring carbon atoms is optionally replaced with N or O and which ring is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In another particular class of compound of formula (Ia) or (Ib),

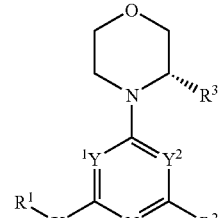
(Ia)

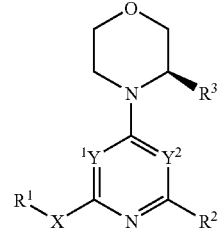
(Ib)

or a pharmaceutically acceptable salt thereof;

$^1Y$ is CH and $Y^2$ is N;

X is a linker group selected from —$S(O)_2CH_2$—, —$S(O)_2CH(CH_3)$— and —$S(O)_2C(CH_3)_2$—;

$R^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —$NHCOCH_3$, —$CONH_2$ and —$CONHCH_3$;

or —$XR^1$ is —$C(CH_3)_2OH$ or —$CH_2OH$;

$R^2$ is selected from phenyl, pyrrolyl, imidazolyl, pyrazolyl, furanyl, thienyl, pyridinyl, pyrimidinyl, pyridazinyl, thiazolyl which group is substituted by —$NHCSNHR^{19}$ and optionally substituted by one or more substituent group independently selected from halo, cyano, nitro, —$R^{11}$, —$OR^{11}$, —$COR^{11}$, —$CONR^{11}R^{12}$, —$NR^{11}R^{12}$ and —$NR^{11}COR^{12}$;

$R^3$ is methyl;

$R^{11}$, $R^{12}$ and $R^{18}$ are independently hydrogen or a group selected from $C_{1-6}$alkyl, carbocyclyl and heterocyclyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino and bis($C_{1-6}$alkyl)amino; and $R^{19}$ is hydrogen or a group selected from $C_{1-6}$alkyl, $C_{3-6}$cycloakyl, aryl, heteroaryl, aryl$C_{1-6}$alkyl and heteroaryl$C_{1-6}$alkyl which group is optionally substituted by one or more substituent groups selected from halo, cyano, nitro, hydroxy, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (Ia) or (Ib)

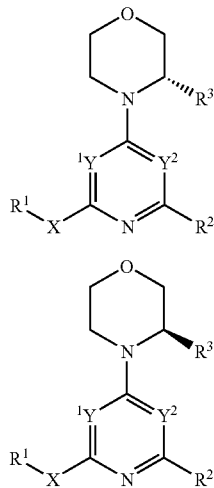

or a pharmaceutically acceptable salt thereof;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N.

R$^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$;

R$^2$ is phenyl or pyridyl substituted by —NHCSNHR$^{19}$ and optionally substituted by one or more substituent group independently selected from fluoro, methyl, methoxy, hydroxymethyl, cyanomethyl, —CONH$_2$, —CONHCH$_3$ and —CON(CH$_3$)$_2$;

R$^3$ is methyl; and

R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyridinyl and pyrimidinyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

In a further particular class of compound of formula (Ia) or (Ib)

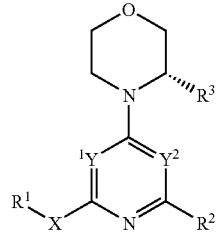

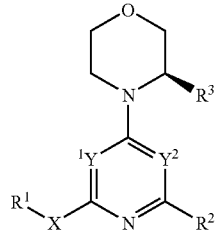

or a pharmaceutically acceptable salt thereof;

m is 1;

X is a linker group selected from —S(O)$_2$CH$_2$—, —S(O)$_2$CH(CH$_3$)— and —S(O)$_2$C(CH$_3$)$_2$—;

$^1$Y is CH and Y$^2$ is N;

R$^1$ is a group selected from methyl, isopropyl, cyclopropyl, cyclohexyl, —CH$_2$CH$_2$OH, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrolidin-3-yl, thiazol-2-yl, 4-methylthiazol-2-yl, and 3-methyl-1,3,4-thiadiazol-2-yl;

R$^2$ is

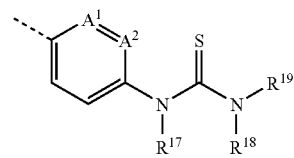

wherein A$^1$ and A$^2$ are selected from CH or N provided that at least one of A$^1$ or A$^2$ is CH;

R$^{17}$ is hydrogen;

R$^{18}$ is hydrogen; and

R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, 4-methylphenyl, 4-chlorophenyl, 4-trifluoromethylphenyl, 4-flurophenyl, 4-methoxyphenyl, 3,4-difluorophenyl, thien-2-yl, —CH$_2$(imidazol-2-yl), —CH$_2$(imidazol-3-yl), is oxazolyl-3-yl, 6-oxo-1H-pryrdin-2-yl, 5-methylisoxazol-3-yl, 1-methylpyrazol-4-yl, —CH$_2$(1-methylpyrazol-4-yl), 6-methoxypryridin-3-yl, 5-fluoropyridin-2-yl, pyrimidin-2-yl, and 1H-pyrazol-3-yl;

and, R$^3$ is methyl.

In a further particular class of compound of formula (Ia) or (Ib)

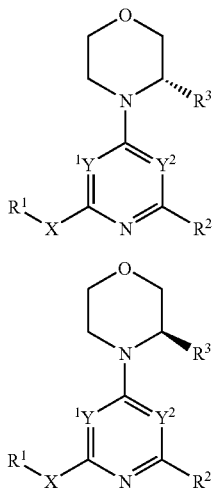

(Ia)

(Ib)

or a pharmaceutically acceptable salt thereof;
m is 1;
$Y^1$ is CH and $Y^2$ is N;
X is a linker group selected from —S(O)$_2$CH$_2$—, —S(O)$_2$CH(CH$_3$)— and —S(O)$_2$C(CH$_3$)$_2$—; and
$R^1$ is a group selected from methyl, isopropyl, cyclopropyl, cyclohexyl, —CH$_2$CH$_2$OH, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrolidin-3-yl, thiazol-2-yl, 4-methylthiazol-2-yl, and 3-methyl-1,3,4-thiadiazol-2-yl; or —XR$^1$ is C(CH$_3$)$_2$OH;
$R^2$ is

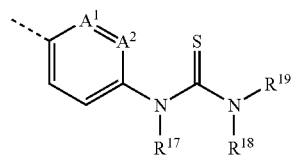

wherein A$^1$ and A$^2$ are selected from CH or N provided that at least one of A$^1$ or A$^2$ is CH;
$R^{17}$ is hydrogen;
$R^{18}$ is hydrogen; and
$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, phenyl, 4-methylphenyl, 4-chlorophenyl, 4-trifluoromethylphenyl, 4-flurophenyl, 4-methoxyphenyl, 3,4-difluorophenyl, thien-2-yl, —CH$_2$(imidazol-2-yl), —CH$_2$(imidazol-3-yl), isoxazolyl-3-yl, 6-oxo-1H-pryrdin-2-yl, 5-methylisoxazol-3-yl, 1-methylpyrazol-4-yl, —CH$_2$(1-methylpyrazol-4-yl), 6-methoxypryridin-3-yl, 5-fluoropyridin-2-yl, pyrimidin-2-yl, and 1H-pyrazol-3-yl;
and, $R^3$ is methyl.

In a further particular class of compound of formula (Ia) or (Ib)

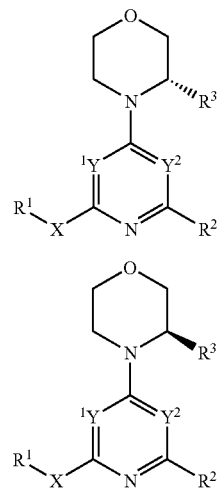

(Ia)

(Ib)

or a pharmaceutically acceptable salt thereof;
m is 1;
$Y^1$ is CH and $Y^2$ is N;
X is a linker group selected from —S(O)$_2$CH$_2$—, —S(O)$_2$CH(CH$_3$)— and —S(O)$_2$C(CH$_3$)$_2$—; and
$R^1$ is a group selected from methyl, isopropyl, cyclopropyl, cyclohexyl, —CH$_2$CH$_2$OH, —CH$_2$CH$_2$NC(O)CH$_3$, —CH$_2$CONH$_2$, phenyl, 4-fluorophenyl, 2-chlorophenyl, 2-trifluoromethylphenyl, 2-methoxyphenyl, 2-methylphenyl, 4-acetamidophenyl, 4-aminophenyl, pyridin-4-yl, pyridin-2-yl, 2-oxopyrolidin-3-yl, thiazol-2-yl, 4-methylthiazol-2-yl, and 3-methyl-1,3,4-thiadiazol-2-yl; or —XR$^1$ is C(CH$_3$)$_2$OH;
$R^2$ is

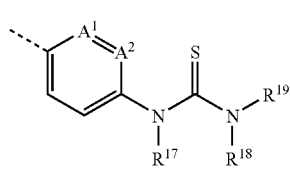

wherein A$^1$ and A$^2$ are CH;
$R^{17}$ is hydrogen;
$R^{18}$ is hydrogen; and
$R^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, —CH$_2$(cyclopropyl), —CH$_2$CH$_2$NMe$_2$, —CH(CH$_3$)CH$_2$OH, —C(CH$_3$)$_2$CH$_2$OH, —CH$_2$CH$_2$OH, —CH$_2$CH$_2$CH$_2$OH, phenyl, 4-methylphenyl, 4-chlorophenyl, 4-trifluoromethylphenyl, 4-fluorophenyl, 4-methoxyphenyl, 3,4-difluorophenyl, thien-2-yl, —CH$_2$(imidazol-2-yl), —CH$_2$(imidazol-3-yl), isoxazolyl-3-yl, 6-oxo-1H-pryrdin-2-yl, 5-methylisoxazol-3-yl, 1-methylpyrazol-4-yl, —CH$_2$(1-methylpyrazol-4-yl), 6-methoxypryridin-3-yl, 5-fluoropyridin-2-yl, pyrimidin-2-yl, and 1H-pyrazol-3-yl;
and, $R^3$ is methyl.

In a further particular class of compound of formula (Ia) or (Ib)

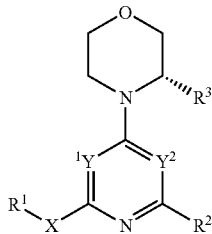
(Ia)

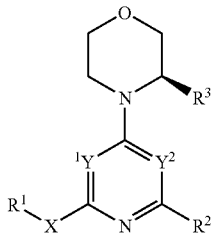
(Ib)

or a pharmaceutically acceptable salt thereof;
m is 1;
$^1Y$ is CH and $Y^2$ is N;
X is a linker group selected from —S(O)$_2$CH$_2$—, —S(O)$_2$CH(CH$_3$)— and —S(O)$_2$C(CH$_3$)$_2$—; and
R$^1$ is a group selected from methyl, —CH$_2$CH$_2$OH and phenyl; or
—XR$^1$ is C(CH$_3$)$_2$OH;
R$^2$ is

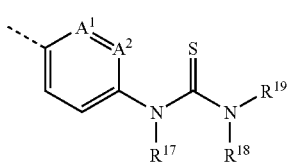

wherein A$^1$ and A$^2$ are selected from CH or N provided that at least one of A$^1$ or A$^2$ is CH;
R$^{17}$ is hydrogen;
R$^{18}$ is hydrogen; and
R$^{19}$ is a group selected from methyl, ethyl, cyclopropyl, —CH$_2$CH$_2$NMe$_2$, —CH$_2$CH$_2$OH, phenyl, 4-flurophenyl, and 4-methoxyphenyl;
and, R$^3$ is methyl.

In a further particular class of compound of formula (Ia) or (Ib)

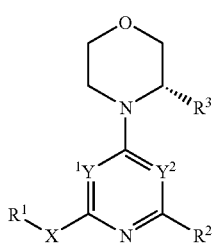
(Ia)

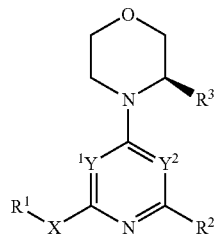
(Ib)

or a pharmaceutically acceptable salt thereof;
m is 1;
$^1Y$ is CH and $Y^2$ is N;
X is a linker group selected from —S(O)$_2$CH$_2$—, —S(O)$_2$CH(CH$_3$)— and —S(O)$_2$C(CH$_3$)$_2$—; and
R$^1$ is a group selected from methyl, —CH$_2$CH$_2$OH and phenyl; or
—XR$^1$ is C(CH$_3$)$_2$OH;
R$^2$ is

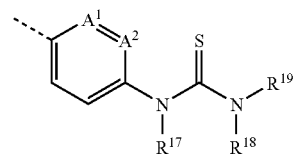

wherein A$^1$ and A$^2$ are CH;
R$^{17}$ is hydrogen;
R$^{18}$ is hydrogen; and
R$^{19}$ is a group selected from methyl, ethyl, cyclopropyl, —CH$_2$CH$_2$NMe$_2$, —CH$_2$CH$_2$OH, phenyl, 4-flurophenyl, and 4-methoxyphenyl;
and, R$^3$ is methyl.

In a further particular class of compound of formula (Ia) or (Ib)

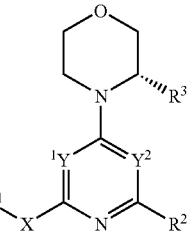
(Ia)

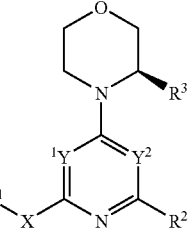
(Ib)

or a pharmaceutically acceptable salt thereof;
m is 1;
$^1Y$ is CH and $Y^2$ is N;
X is a linker group —S(O)$_2$C(CH$_3$)$_2$—; and
R$^1$ is a group selected from methyl and phenyl; or
—XR$^1$ is —C(CH$_3$)$_2$OH;

$R^2$ is

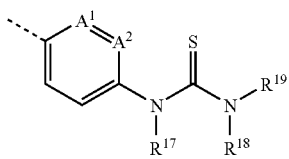

wherein $A^1$ and $A^2$ are CH;
$R^{17}$ is hydrogen;
$R^{18}$ is hydrogen; and
$R^{19}$ is a —CH$_2$CH$_2$OH;
and, $R^3$ is methyl.

Another aspect of the invention provides a compound, or a combination of compounds, selected from any one of the Examples or a pharmaceutically acceptable salt thereof.

Another aspect of the invention provides a compound, or a combination of compounds, selected from 3-ethyl-1-[4-[4-[(3S)-3-methylmorpholin-4-yl]-6-(methylsulfonylmethyl)pyrimidin-2-yl]phenyl]thiourea, 3-Cyclopropyl-1-[4-[4-[(3S)-3-methylmorpholin-4-yl]-6-(methylsulfonylmethyl)pyrimidin-2-yl]phenyl]thiourea, 3-(4-fluorophenyl)-1-[4-[4-[(3S)-3-methylmorpholin-4-yl]-6-(methylsulfonylmethyl)pyrimidin-2-yl]phenyl]thiourea, 1-[4-[4-[(3S)-3-methylmorpholin-4-yl]-6-(methylsulfonylmethyl)pyrimidin-2-yl]phenyl]-3-phenyl-thiourea, 3-(4-methoxyphenyl)-1-[4-[4-[(3S)-3-methylmorpholin-4-yl]-6-(methylsulfonylmethyl)pyrimidin-2-yl]phenyl]thiourea, 3-cyclopropyl-1-[4-[4-[(3S)-3-methylmorpholin-4-yl]-6-(2-methylsulfonylpropan-2-yl)pyrimidin-2-yl]phenyl]thiourea, 3-methyl-1-[4-[4-[(3S)-3-methylmorpholin-4-yl]-6-(2-methylsulfonylpropan-2-yl)pyrimidin-2-yl]phenyl]thiourea, 3-ethyl-1-[4-[4-[(3S)-3-methylmorpholin-4-yl]-6-(2-methylsulfonylpropan-2-yl)pyrimidin-2-yl]phenyl]thiourea, 3-(2-hydroxyethyl)-1-[4-[4-[(3S)-3-methylmorpholin-4-yl]-6-(2-methylsulfonylpropan-2-yl)pyrimidin-2-yl]phenyl]thiourea, 3-(2-dimethylaminoethyl)-1-[4-[4-[(3S)-3-methylmorpholin-4-yl]-6-(2-methylsulfonylpropan-2-yl)pyrimidin-2-yl]phenyl]thiourea, 1-[4-[4-[2-(Benzenesulfonyl)propan-2-yl]-6-[(3S)-3-methylmorpholin-4-yl]pyrimidin-2-yl]phenyl]-3-methylthiourea, 1-[4-[4-[2-(benzenesulfonyl)propan-2-yl]-6-[(3S)-3-methylmorpholin-4]pyrimidin-2-yl]phenyl]-3-cyclopropylthiourea, 1-[4-[4-[2-(benzenesulfonyl)propan-2-yl]-6-[(3S)-3-methylmorpholin-4-yl]pyrimidin-2-yl]phenyl]-3-ethylthiourea, 1-[4-[4-[2-(benzenesulfonyl)propan-2-yl]-6-[(3S)-3-methylmorpholin-4-yl]pyrimidin-2-yl]phenyl]-3-(2-hydroxyethyl)thiourea, 3-(2-hydroxyethyl)-1-[4-[4-[2-(3-hydroxypropylsulfonyl)propan-2-yl]-6-[(3S)-3-methylmorpholin-4-yl]pyrimidin-2-yl]phenyl]thiourea, 1-[4-[4-[2-(3-hydroxypropylsulfonyl)propan-2-yl]-6-[(3S)-3-methylmorpholin-4-yl]pyrimidin-2-yl]phenyl]-3-methylthiourea, 3-cyclopropyl-1-[4-[4-[2-(3-hydroxypropylsulfonyl)propan-2-yl]-6-[(3S)-3-methylmorpholin-4-yl]pyrimidin-2-yl]phenyl]thiourea, 3-ethyl-1-[4-[4-[2-(3-hydroxypropylsulfonyl)propan-2-yl]-6-[(3S)-3-methylmorpholin-4-yl]pyrimidin-2-yl]phenyl]thiourea, 3-(2-hydroxyethyl)-1-[4-[4-(2-hydroxypropan-2-yl)-6-[(3S)-3-methylmorpholin-4-yl]pyrimidin-2-yl]phenyl]thiourea, 1-[4-[4-(2-hydroxypropan-2-yl)-6-[(3S)-3-methylmorpholin-4-yl]pyrimidin-2-yl]phenyl]-3-methylthiourea, 3-cyclopropyl-1-[4-[4-(2-hydroxypropan-2-yl)-6-[(3S)-3-methylmorpholin-4-yl]pyrimidin-2-yl]phenyl]thiourea, and 3-ethyl-1-[4-[4-(2-hydroxypropan-2-yl)-6-[(3S)-3-methylmorpholin-4-yl]pyrimidin-2-yl]phenyl]thiourea or a pharmaceutically acceptable salt thereof.

The invention also provides processes for the preparation of a compound of formula (I) or a pharmaceutically acceptable salt thereof.

A compound of formula (I), wherein X=—S(O)$_2$CR$^6$R$^7$—, may be prepared by oxidising a compound of the formula (I), wherein X=SCR$^6$R$^7$—, for example by using Oxone® at room temperature in a mixed solvent system of water and ethanol

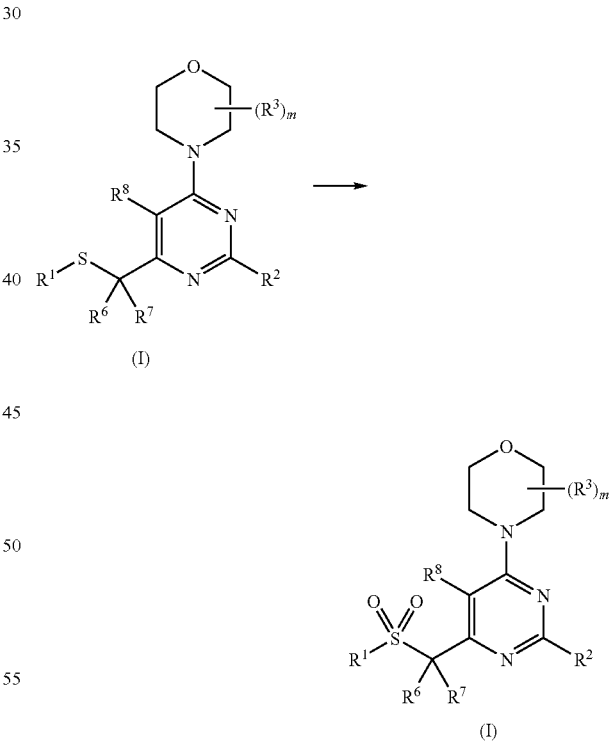

A compound of formula (I), wherein R$^1$X=R$^1$OCR$^6$R$^7$—, may be prepared by the reaction of a compound of formula (I), wherein R$^1$X=HOCR$^6$R$^7$—, with a compound of formula (II), wherein L$^1$ is a leaving group (such as halo, tosyl, mesyl etc.) optionally in the presence of a suitable base such as triethylamine and a solvent such as tetrahydrofuran or N,N-dimethylformamide.

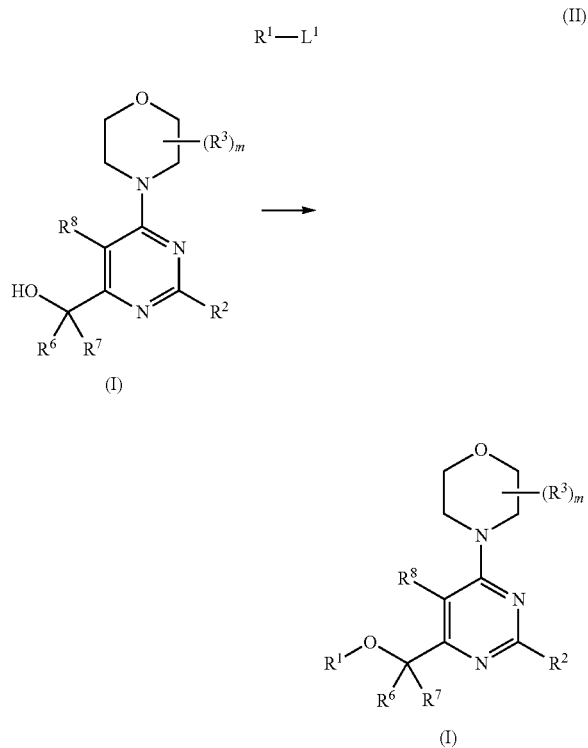

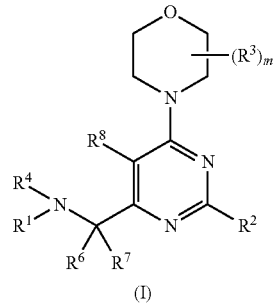

A compound of formula (I), wherein R¹X═R¹R⁴NCR⁶R⁷—, may be prepared by the reaction of a compound of formula (I), wherein R¹X═HR⁴NCR⁶R⁷—, with a compound of formula (II), wherein L¹ is a leaving group (such as halo, tosyl, mesyl etc.) optionally in the presence of a suitable base such as triethylamine and a solvent such as tetrahydrofuran or N,N-dimethylformamide; or by the reaction of a compound of formula (I), wherein R¹X═HR⁴NCR⁶R⁷—, with a compound of formula (III) in the presence of a suitable reducing agent such as NaCNBH₃.

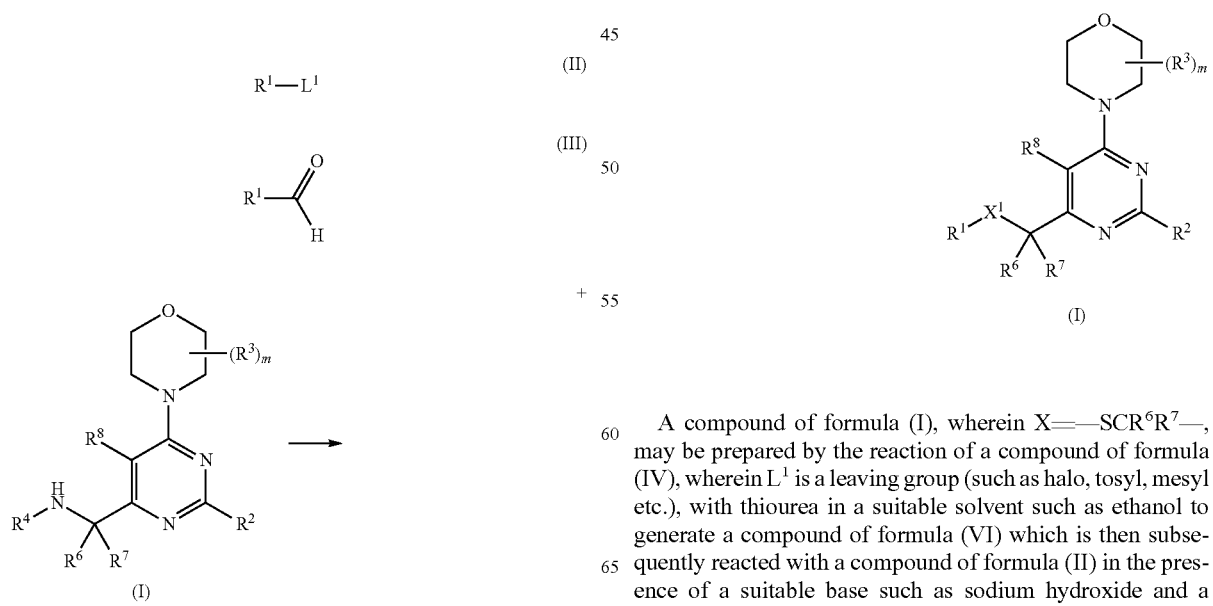

A compound of formula (I), wherein X¹═—S(O)₂CR⁶R⁷—, —SCR⁶R⁷—, —OCR⁶R⁷—, —R⁴NCR⁶R⁷—, —S(O)CR⁶R⁷—, may be prepared by the reaction of a compound of formula (IV), wherein L¹ is a leaving group (such as halo, tosyl, mesyl etc.), with a compound of formula (V) optionally in the presence of a suitable base such as triethylamine and a solvent such as tetrahydrofuran or N,N-dimethylformamide.

A compound of formula (I), wherein X═—SCR⁶R⁷—, may be prepared by the reaction of a compound of formula (IV), wherein L¹ is a leaving group (such as halo, tosyl, mesyl etc.), with thiourea in a suitable solvent such as ethanol to generate a compound of formula (VI) which is then subsequently reacted with a compound of formula (II) in the presence of a suitable base such as sodium hydroxide and a solvent such as N,N-dimethylformamide.

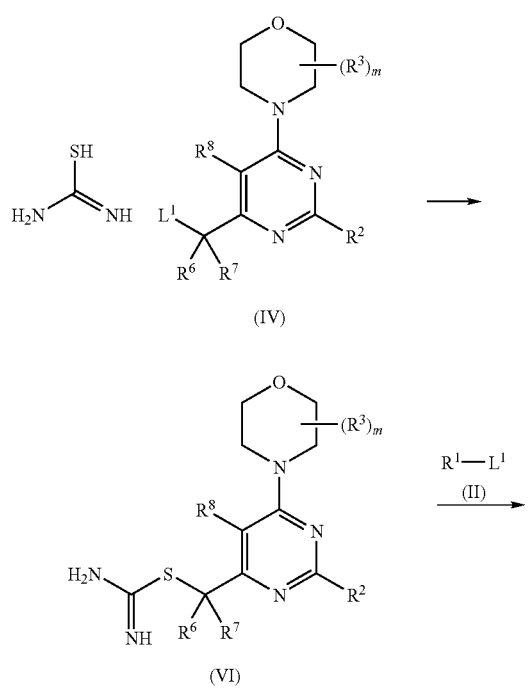

(IV)

(VI)

(I)

A compound of formula (I), wherein X=—R⁴NC(O)—, may be prepared by the reaction of a compound of formula (VII) with an amine of formula R¹R⁴NH following the suitable activation of the carboxylic acid by methods known in the literature such as the use of a coupling agent such as HATU or the conversion to an acyl chloride.

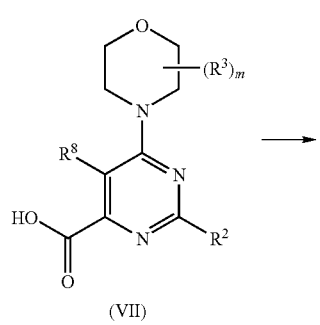

(VII)

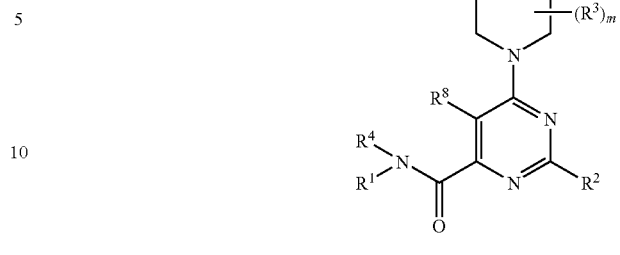

(I)

A compound of formula (I), wherein X=—S(O)$_2$CR⁶R⁷—, may be prepared by the sequential reaction of a compound of formula (I), wherein X=—S(O)$_2$CH$_2$—, with a compound of formula (VIII) followed by reaction with a compound of formula (IX), wherein L¹ is a leaving group (such as halo, tosyl, mesyl etc.), in the presence of a suitable base such as sodium hydride or potassium tert-butoxide in a suitable solvent such as tetrahydrofuran or N,N-dimethylformamide.

R⁶—L¹ (VIII)

R⁷—L¹ (IX)

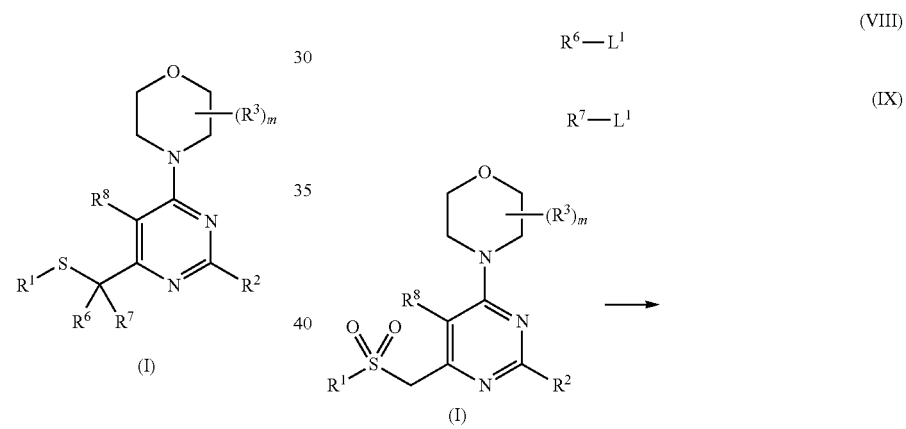

A compound of formula (I), wherein R¹X=HOCR⁶R⁷—, may be prepared by the reaction of a compound of formula (X), with suitable organometallic reagents of formula (XI) and formula (XII) such as the grignard reagent in a suitable solvent. Where R⁶ and R⁷ are different then it may be possible to use techniques known in the literature such the conversion of a compound of formula (X) to the Weinreb amide and reaction with an organometallic reagent of formula (XI) and then reaction with an organometallic reagent of formula (XII) in a subsequent step.

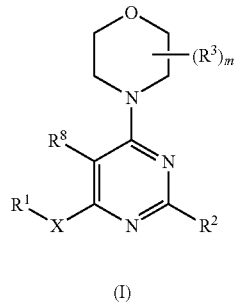

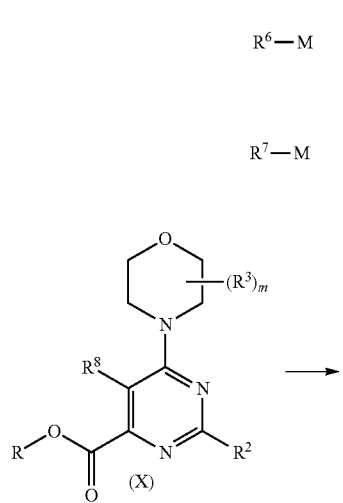

It will be appreciated that a compound of formula (XIII) may be transformed into another compound of formula (XIII) by techniques such as oxidation, alkylation, reductive amination etc., either listed above or otherwise known in the literature.

A compound of formula (XIII), wherein $X^1$=—S(O)$_2$CR$^6$R$^7$—, —SCR$^6$R$^7$—, —OCR$^6$R$^7$—, —R$^4$NCR$^6$R$^7$—, —S(O)CR$^6$R$^7$—, may be prepared by the reaction of a compound of formula (XIV), wherein L$^1$ is a leaving group (such as halo, tosyl, mesyl etc.), with a compound of formula (V) optionally in the presence of a suitable base such as triethylamine and a solvent such as tetrahydrofuran or N,N-dimethylformamide.

A compound of formula (I) may be prepared from a compound of formula (XIII), wherein L$^2$ is a leaving group (such as halo, tosyl, mesyl, —SMe, —S(O)$_2$Me etc.), with a suitable organometallic reagent (such as the boronic acid R$^2$B(OH)$_2$ or the boronic ester R$^2$B(OR)$_2$ etc.) in the presence of a suitable metal catalyst (such as palladium or copper) in a suitable solvent such as 1,4-dioxane. Alternatively where R$^2$ connects to the pyrimidine ring through a nitrogen, oxygen or sulphur atom a compound of formula (I) may be prepared from a compound of formula (XIII), wherein L$^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

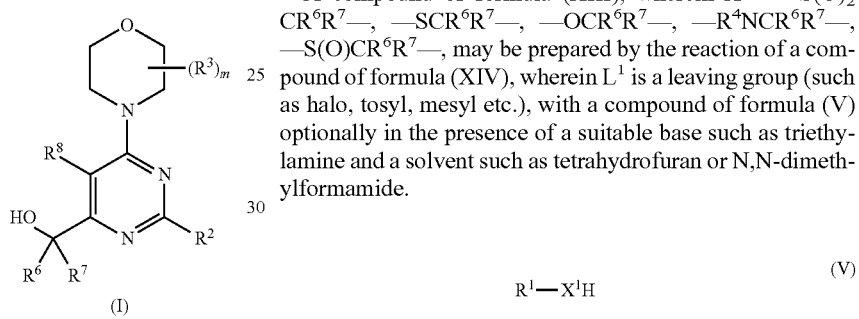

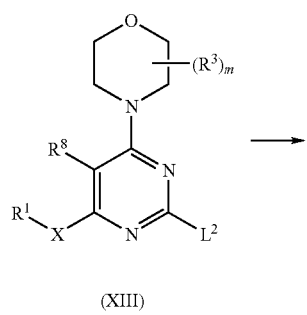

A compound of formula (XIII), wherein X=—SCR$^6$R$^7$—, may be prepared by the reaction of a compound of formula (XIV), wherein L$^1$ is a leaving group (such as halo, tosyl, mesyl etc.), with thiourea in a suitable solvent such as ethanol to generate a compound of formula (XV) which is then subsequently reacted with a compound of formula (II) in the presence of a suitable base such as sodium hydroxide and a solvent such as N,N-dimethylformamide.

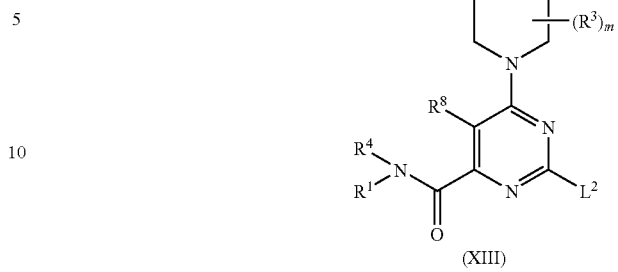

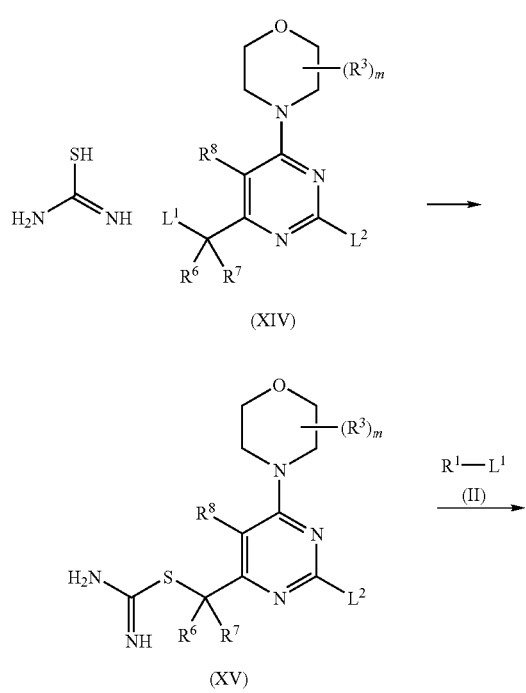

A compound of formula (XIII), wherein X=—S(O)$_2$ CR$^6$R$^7$—, may be prepared by the sequential reaction of a compound of formula (XIII), wherein X=—S(O)$_2$CH$_2$—, with a compound of formula (VIII) followed by reaction with a compound of formula (IX), wherein L$^1$ is a leaving group (such as halo, tosyl, mesyl etc.), in the presence of a suitable base such as sodium hydride or potassium tert-butoxide in a suitable solvent such as tetrahydrofuran or N,N-dimethylformamide.

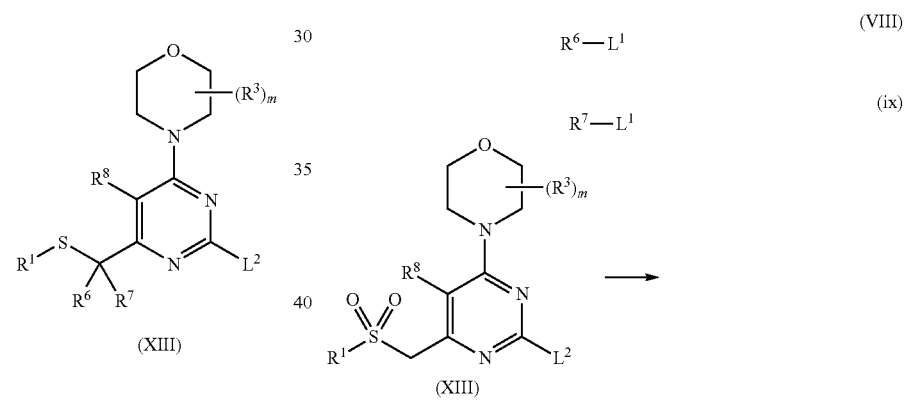

A compound of formula (XIII), wherein X=—R$^4$NC (O)—, may be prepared by the reaction of a compound of formula (XVI) with an amine of formula R$^1$R$^4$NH following the suitable activation of the carboxylic acid by methods known in the literature such as the use of a coupling agent such as HATU or the conversion to an acyl chloride.

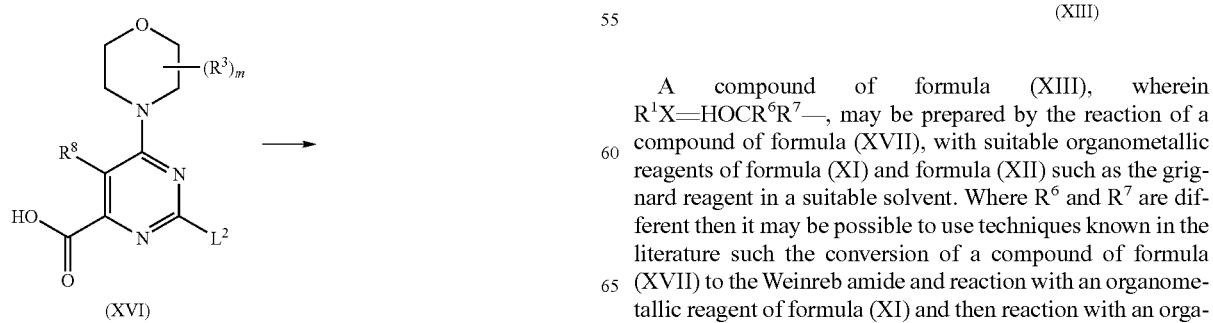

A compound of formula (XIII), wherein R$^1$X=HOCR$^6$R$^7$—, may be prepared by the reaction of a compound of formula (XVII), with suitable organometallic reagents of formula (XI) and formula (XII) such as the grignard reagent in a suitable solvent. Where R$^6$ and R$^7$ are different then it may be possible to use techniques known in the literature such the conversion of a compound of formula (XVII) to the Weinreb amide and reaction with an organometallic reagent of formula (XI) and then reaction with an organometallic reagent of formula (XII) in a subsequent step.

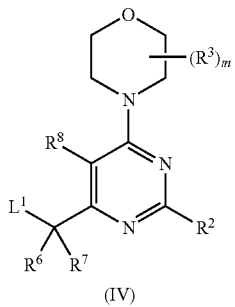

(XI)

(XIi)

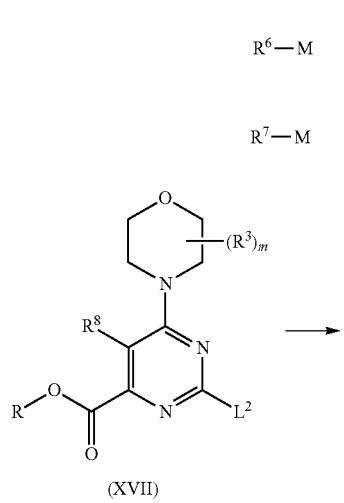

(XVII)

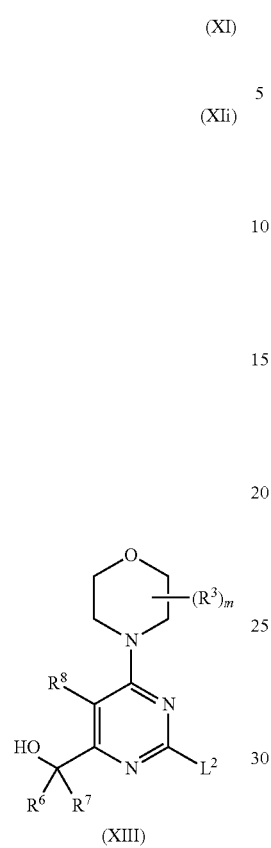

(XIII)

A compound of formula (IV) may be prepared from a compound of formula (XIV), wherein $L^2$ is a leaving group (such as halo, tosyl, mesyl, —SMe, —S(O)$_2$Me etc.) and $L^1$ is a leaving group (such as halo, tosyl, mesyl etc.), with a suitable organometallic reagent (such as the boronic acid $R^2B(OH)_2$ or the boronic ester $R^2B(OR)_2$ etc.) in the presence of a suitable metal catalyst (such as palladium or copper) in a suitable solvent such as 1,4-dioxane. Alternatively where $R^2$ connects to the pyrimidine ring through a nitrogen, oxygen or sulphur atom a compound of formula (IV) may be prepared from a compound of formula (XIV), wherein $L^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

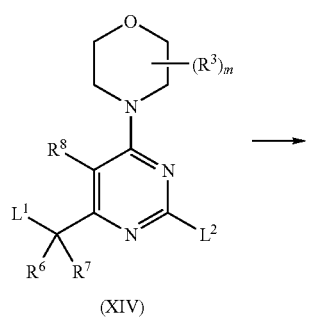

(XIV)

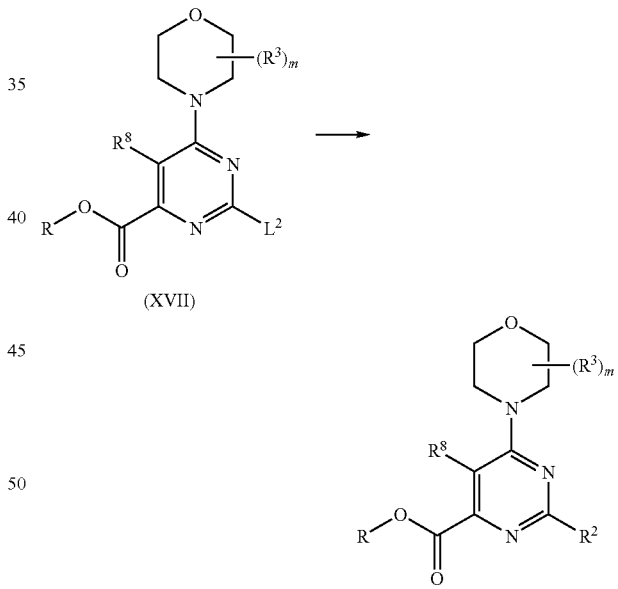

A compound of formula (X) may be prepared from a compound of formula (XVII), wherein $L^2$ is a leaving group (such as halo, tosyl, mesyl, —SMe, —S(O)$_2$Me etc.) and R is a hydrogen or $C_{1-4}$alkyl group, with a suitable organometallic reagent (such as the boronic acid $R^2B(OH)_2$ or the boronic ester $R^2B(OR)_2$ etc.) in the presence of a suitable metal catalyst (such as palladium or copper) in a suitable solvent such as 1,4-dioxane. Alternatively where $R^2$ connects to the pyrimidine ring through a nitrogen, oxygen or sulphur atom a compound of formula (X) may be prepared from a compound of formula (XVII), wherein $L^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

A compound of formula (XVIII) may be prepared from a compound of formula (XIX), wherein $L^2$ is a leaving group (such as halo, tosyl, mesyl, —SMe, —S(O)$_2$Me etc.), with a suitable organometallic reagent (such as the boronic acid $R^2B(OH)_2$ or the boronic ester $R^2B(OR)_2$ etc.) in the presence of a suitable metal catalyst (such as palladium or copper) in a suitable solvent such as 1,4-dioxane. Alternatively where $R^2$ connects to the pyrimidine ring through a nitrogen, oxygen or sulphur atom a compound of formula (XVIII) may be prepared from a compound of formula (XIX), wherein $L^2$ is a leaving group (such as halo, tosyl, mesyl, —SMe, —S(O)$_2$ Me etc.), by reaction with the required amine, alcohol or thiol in the presence of a suitable base such as potassium carbonate in a suitable solvent such as N,N-dimethylformamide.

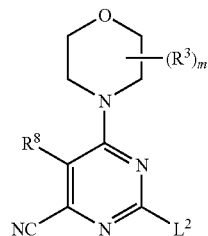

(XIX)

A compound of formula (XX) may be prepared from a compound of formula (XXI), wherein $L^2$ is a leaving group (such as halo, tosyl, mesyl, —SMe, —S(O)$_2$Me etc.), with a suitable organometallic reagent (such as the boronic acid $R^2B(OH)_2$ or the boronic ester $R^2B(OR)_2$ etc.) in the presence of a suitable metal catalyst (such as palladium or copper) in a suitable solvent such as 1,4-dioxane. Alternatively where $R^2$ connects to the pyrimidine ring through a nitrogen, oxygen or sulphur atom a compound of formula (XX) may be prepared from a compound of formula (XXI), wherein $L^2$ is a leaving group (such as halo, tosyl, mesyl, —SMe, —S(O)$_2$Me etc.), by reaction with the required amine, alcohol or thiol in the presence of a suitable base such as potassium carbonate in a suitable solvent such as N,N-dimethylformamide.

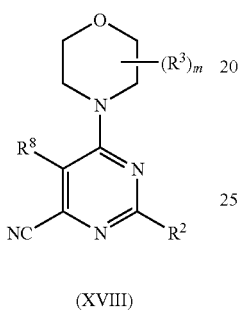

(XVIII)

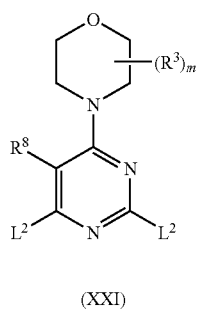 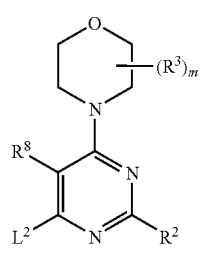

(XXI)  (XX)

A compound of formula (I), wherein $L^1$ is a leaving group (such as halo, tosyl, mesyl etc.), may be prepared by the reaction of a compound of formula (XXII) with a compound of formula (XXIII) optionally in the presence of a suitable base such as triethylamine in a suitable solvent such as N,N-dimethylformamide.

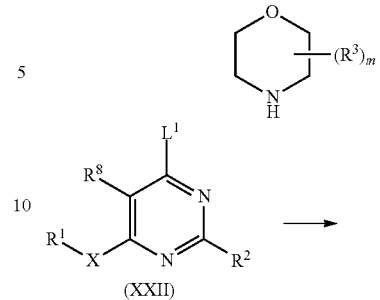

(XXIII)

(XXII)

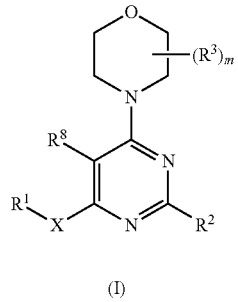

(I)

It will be appreciated that a compound of formula (XXII) may be transformed into another compound of formula (XXII) by techniques such as oxidation, alkylation, reductive amination etc., either listed above or otherwise known in the literature.

A compound of formula (IV), wherein $L^1$ is a leaving group (such as halo, tosyl, mesyl etc.), may be prepared by the reaction of a compound of formula (XXIV) with a compound of formula (XXIII) optionally in the presence of a suitable base such as triethylamine in a suitable solvent such as N,N-dimethylformamide.

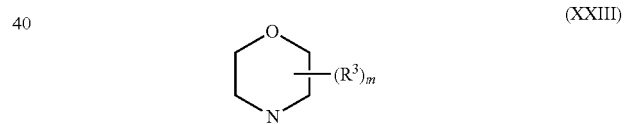

(XXIII)

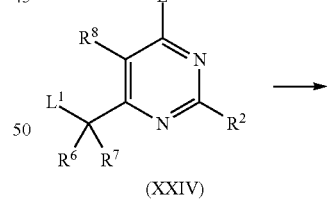

(XXIV)

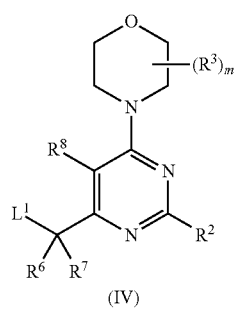

(IV)

A compound of formula (X), wherein $L^1$ is a leaving group (such as halo, tosyl, mesyl etc.) and R is a hydrogen or a C$_{1-4}$alkyl group, may be prepared by the reaction of a compound of formula (XXV) with a compound of formula (XXIII) optionally in the presence of a suitable base such as triethylamine in a suitable solvent such as N,N-dimethylformamide.

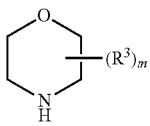

(XXIII)

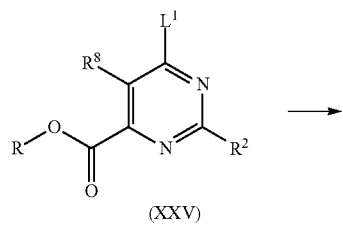

(XXV)

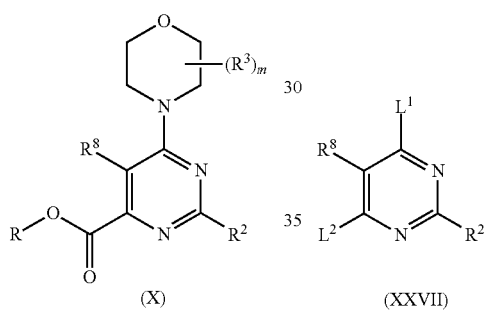

(X)

A compound of formula (XVIII), wherein L$^1$ is a leaving group (such as halo, tosyl, mesyl etc.), may be prepared by the reaction of a compound of formula (XXVI) with a compound of formula (XXIII) optionally in the presence of a suitable base such as triethylamine in a suitable solvent such as N,N-dimethylformamide.

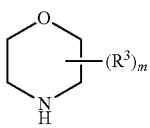

(XXIII)

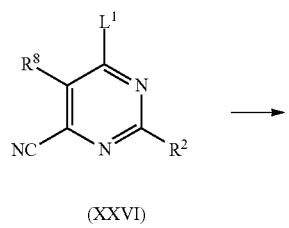

(XXVI)

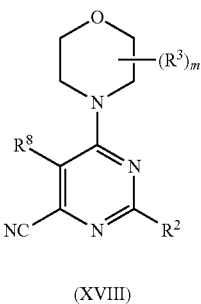

(XVIII)

A compound of formula (XX), wherein L$^1$ is a leaving group (such as halo, tosyl, mesyl etc.) and L$^2$ is a leaving group (such as halo, tosyl, mesyl, —SMe, —S(O)$_2$Me etc.), may be prepared by the reaction of a compound of formula (XXVII) with a compound of formula (XXIII) optionally in the presence of a suitable base such as triethylamine in a suitable solvent such as N,N-dimethylformamide.

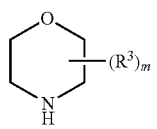

(XXIII)

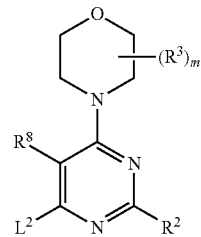

(XXVII)

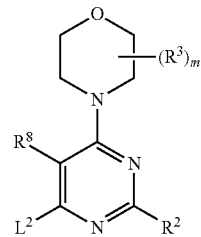

(XX)

A compound of formula (XIII), wherein L$^1$ is a leaving group (such as halo, tosyl, mesyl etc.) and L$^2$ is a leaving group (such as halo, tosyl, mesyl, —SMe, —S(O)$_2$Me etc.), may be prepared by the reaction of a compound of formula (XXVIII) with a compound of formula (XXIII) optionally in the presence of a suitable base such as triethylamine in a suitable solvent such as N,N-dimethylformamide.

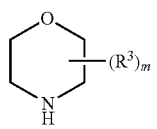

(XXIII)

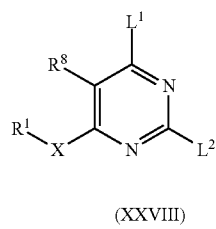

(XXVIII)

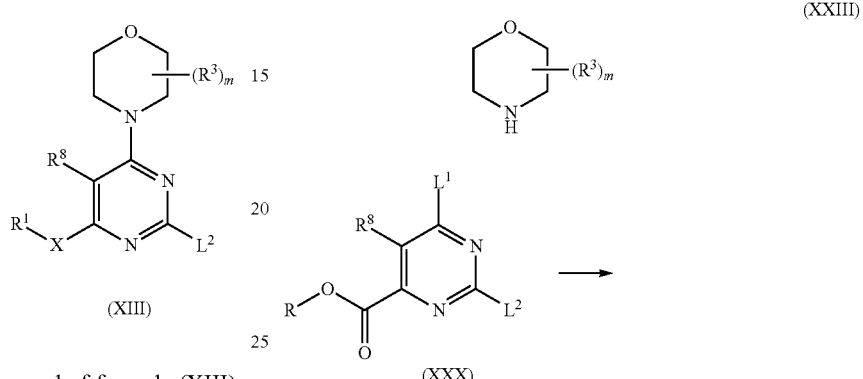

It will be appreciated that a compound of formula (XIII) may be transformed into another compound of formula (XIII) by techniques such as oxidation, alkylation, reductive amination etc., either listed above or otherwise known in the literature.

A compound of formula (XIV), wherein $L^1$ is a leaving group (such as halo, tosyl, mesyl etc.) and $L^2$ is a leaving group (such as halo, tosyl, mesyl, —SMe, —S(O)$_2$Me etc.), may be prepared by the reaction of a compound of formula (XXIX) with a compound of formula (XXIII) optionally in the presence of a suitable base such as triethylamine in a suitable solvent such as N,N-dimethylformamide.

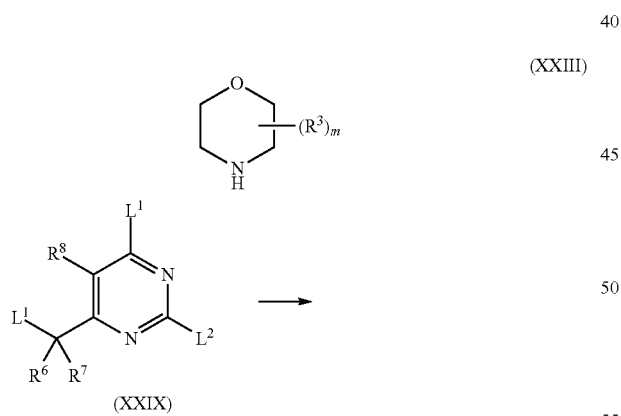

A compound of formula (XVII), wherein $L^1$ is a leaving group (such as halo, tosyl, mesyl etc.) and $L^2$ is a leaving group (such as halo, tosyl, mesyl, —SMe, —S(O)$_2$Me etc.) and R is a hydrogen or a $C_{1-4}$alkyl group, may be prepared by the reaction of a compound of formula (XXX) with a compound of formula (XXIII) optionally in the presence of a suitable base such as triethylamine in a suitable solvent such as N,N-dimethylformamide.

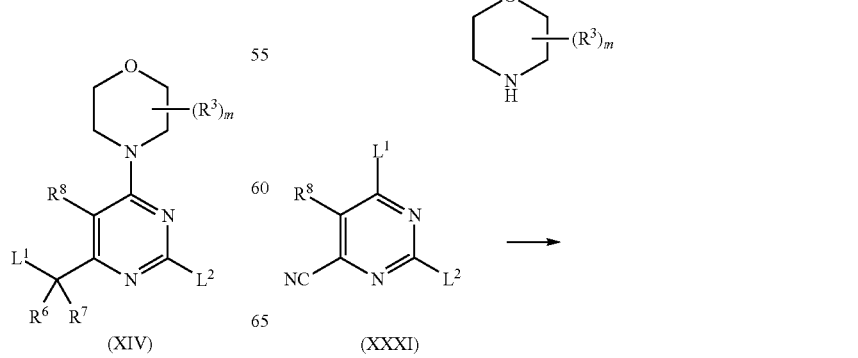

A compound of formula (XIX), wherein $L^1$ is a leaving group (such as halo, tosyl, mesyl etc.) and $L^2$ is a leaving group (such as halo, tosyl, mesyl, —SMe, —S(O)$_2$Me etc.), may be prepared by the reaction of a compound of formula (XXXI) with a compound of formula (XXIII) optionally in the presence of a suitable base such as triethylamine in a suitable solvent such as N,N-dimethylformamide.

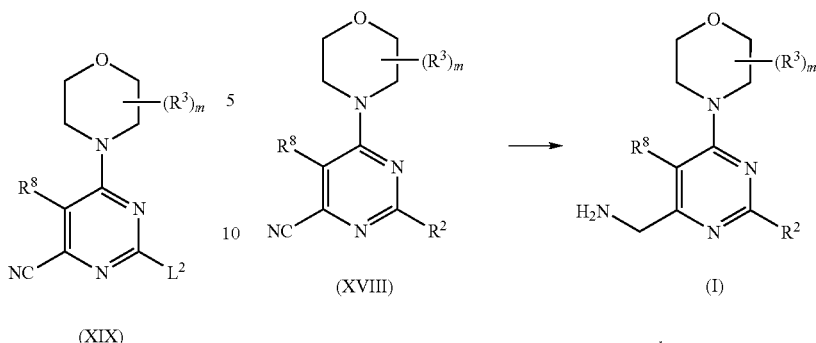

A compound of formula (I), wherein $R^1X=H_2NC(O)—$, may be prepared from a compound of formula (XVIII) by hydrolysis with, for example, sodium hydroxide in a suitable solvent such as a water ethanol mix.

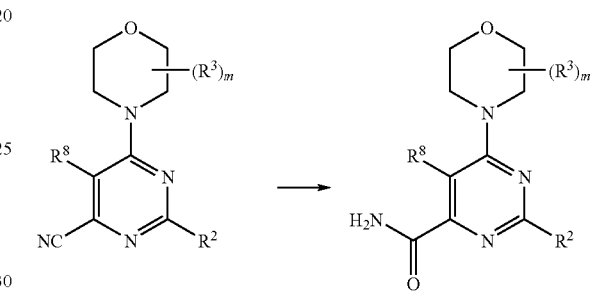

A compound of formula (XXI), wherein $L^1$ is a leaving group (such as halo, tosyl, mesyl etc.) and $L^2$ is a leaving group (such as halo, tosyl, mesyl, —SMe, —S(O)$_2$Me etc.), may be prepared by the reaction of a compound of formula (XXXII) with a compound of formula (XXIII) optionally in the presence of a suitable base such as triethylamine in a suitable solvent such as N,N-dimethylformamide.

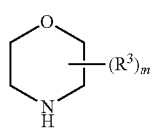

(XXIII)

A compound of formula (I), wherein $R^1X=H_2NCR^6R^7—$, may be prepared from a compound of formula (XVIII) by reaction with organometallic reagents (XI) and (XII).

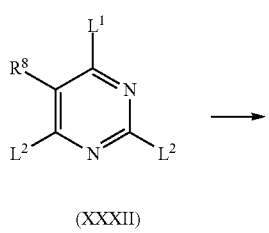

(XXXII)

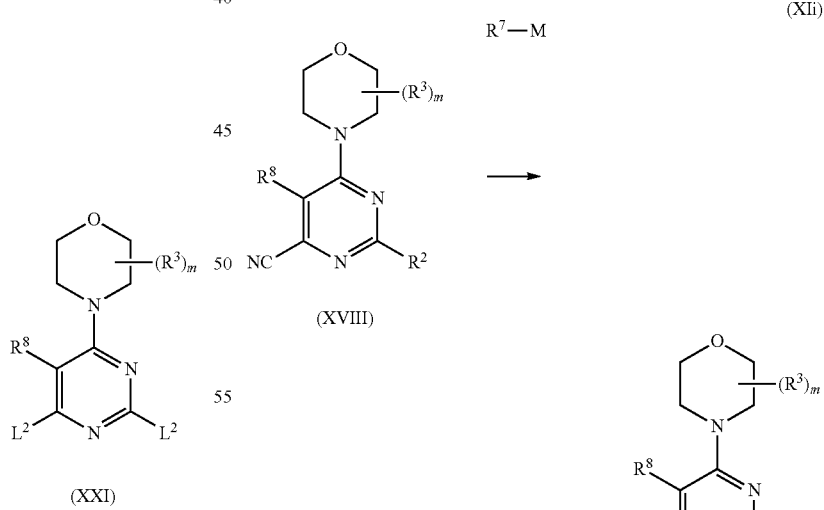

A compound of formula (I), wherein $R^1X=H_2NCH_2—$, may be prepared from a compound of formula (XVIII) by a reduction such as hydrogenation with hydrogen gas and a suitable catalyst such as Palladium on carbon in a suitable solvent such as ethanol.

A compound of formula (XIII), wherein $R^1X=H_2NCH_2—$, may be prepared from a compound of formula (XIX) by a reduction such as hydrogenation with hydrogen gas and a is suitable catalyst such as Palladium on carbon in a suitable solvent such as ethanol.

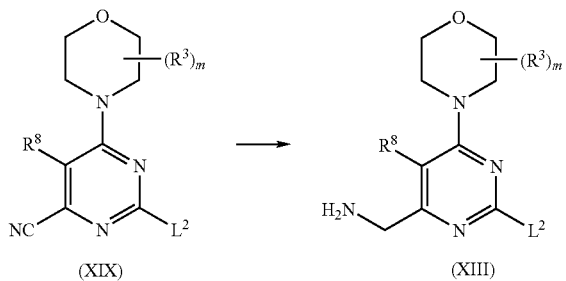

A compound of formula (XIII), wherein $R^1X=H_2NC(O)-$, may be prepared from a compound of formula (XIX) by hydrolysis with, for example, sodium hydroxide in a suitable solvent such as a water ethanol mix.

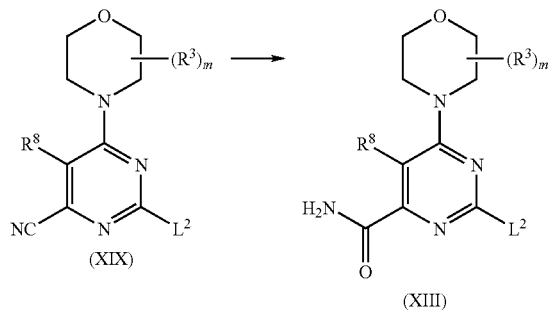

A compound of formula (XIII), wherein $R^1X=H_2NCR^6R^7-$, may be prepared from a compound of formula (XIX) by reaction with organometallic reagents (XI) and (XII).

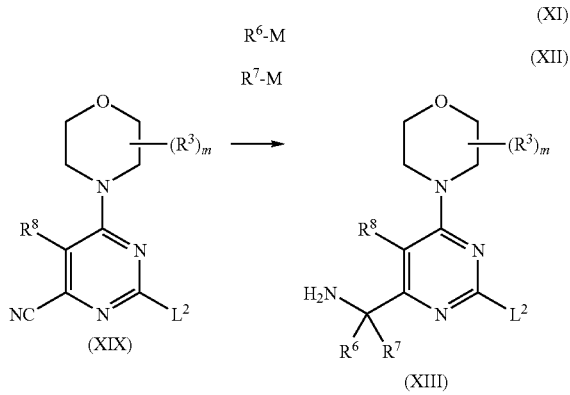

It will be appreciated that the $R^2$ group may be introduced at any stage initially as a carbocyclic or heterocyclic amine (optionally with the nitrogen protected, such protecting groups include but are not limited to nitro, tert-butoxy carbamate etc.) which can be transformed at a subsequent stage in the synthesis (after appropriate deprotection) to a thiourea by either direct reaction with a isothiocyanate (or otherwise activated group) or by activation of the amine (such as with thiophosgene or 1,1'-thiocarbonyldiimidazole) and subsequent reaction with an appropriate amine, or other methods of forming a thiourea known in the literature.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of formula (I) my be converted into further compounds of formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tent-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel and these are provided as a further feature of the invention.

Biological Assays

The following assays can be used to measure the effects of the compounds of the present invention as mTOR kinase inhibitors, as PI3 kinase inhibitors, as inhibitors in vitro of the activation of PI3 kinase signalling pathways and as inhibitors in vitro of the proliferation of MDA-MB-468 human breast adenocarcinoma cells.

(a)(i) In Vitro mTOR Kinase Assay

The assay used AlphaScreen technology (Gray et al., Analytical Biochemistry, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., Journal of Biochemistry, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulfate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one). A 30 µl mixture of recombinant purified mTOR enzyme, 1 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-$NH_2$; Bachem UK Ltd), ATP (20 µM) and a buffer solution [comprising Tris-HCl pH7.4 buffer (50 mM), EGTA (0.1 mM), bovine serum albumin (0.5 mg/mL), DTT (1.25 mM) and manganese chloride (10 mM)] was agitated at room temperature for 90 minutes.

Control wells that produced a maximum signal corresponding to maximum enzyme activity were created by using 5% DMSO instead of test compound. Control wells that produced a minimum signal corresponding to fully inhibited enzyme were created by adding EDTA (83 mM) instead of test compound. These assay solutions were incubated for 2 hours at room temperature.

Each reaction was stopped by the addition of 10 µl of a mixture of EDTA (50 mM), bovine serum albumin (BSA; 0.5 mg/mL) and Tris-HCl pH7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng; Perkin Elmer, Catalogue No. 6760002B and 6760137R respectively) were added and the assay plates were left for about 20 hours at room temperature in the dark. The resultant signals arising from laser light excitation at 680 nm were read using a Packard Envision instrument.

Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead : acceptor bead complex produces a signal that can be measured. Accordingly, the presence of mTOR kinase activity results in an assay signal. In the presence of an mTOR kinase inhibitor, signal strength is reduced.

mTOR enzyme inhibition for a given test compound was expressed as an $IC_{50}$ value.

(a)(ii) In Vitro mTOR Kinase Assay (Echo)

The assay used AlphaScreen technology (Gray et al., Analytical Biochemistry, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., Journal of Biochemistry, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulfate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted in into waterDMSO as required to give a range of final assay concentrations. Aliquots (120 nl2 µl) of each compound dilution were acoustically dispensedplaced using a Labcyte Echo 550 into a well of a Greiner 384-well low volume (LV) white polystyrene plate (Greiner Bio-one). A 1230 µl mixture of recombinant purified mTOR enzyme, 1 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-$NH_2$; Bachem UK Ltd), ATP (20 µM) and a buffer solution [comprising Tris-HCl pH7.4 buffer (50 mM), EGTA (0.1 mM), bovine serum albumin (0.5 mg/mL), DTT (1.25 mM) and manganese chloride (10 mM)] was incubated at room temperature for 12090 minutes.

Control wells that produced a maximum signal corresponding to maximum enzyme activity were created by using 100 5% DMSO instead of test compound. Control wells that produced a minimum signal corresponding to fully inhibited enzyme were created by adding LY294002EDTA (100 uM83 mM) compound. These assay solutions were incubated for 2 hours at room temperature.

Each reaction was stopped by the addition of 510 μl of a mixture of EDTA (50 mM), bovine serum albumin (BSA; 0.5 mg/mL) and Tris-HCl pH7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng; Perkin Elmer, Catalogue No. 6760002B and 6760137R respectively) were added and the assay plates were left overnight at room temperature in the dark. The resultant signals arising from laser light excitation at 680 nm were read using a Packard Envision instrument.

Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead : acceptor bead complex produces a signal that can be measured. Accordingly, the presence of mTOR kinase activity results in an assay signal. In the presence of an mTOR kinase inhibitor, signal strength is reduced. mTOR enzyme inhibition for a given test compound was expressed as an $IC_{50}$ value.

(b)(i) In Vitro PI3K Enzyme Assay

The assay used AlphaScreen technology (Gray et al., Analytical Biochemistry, 2003, 313: 234-245) to determine the ability of test compounds to inhibit phosphorylation by recombinant Type I PI3K enzymes of the lipid PI(4,5)P2.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ respectively) were sub-cloned into a pDEST10 vector (Invitrogen Limited, Fountain Drive, Paisley, UK). The vector is a Gateway-adapted version of Fastbacl containing a 6-His epitope tag. A truncated form of Type Ib human PI3K p110γ isoform corresponding to amino acid residues 144-1102 (EMBL Accession No. X8336A) and the full length human p85α regulatory subunit (EMBL Accession No. HSP13KIN) were also sub-cloned into pFastBacl vector containing a 6-His epitope tag. The Type Ia p110 constructs were co-expressed with the p85α regulatory subunit. Following expression in the baculovirus system using standard baculovirus expression techniques, expressed proteins were purified using the His epitope tag using standard purification techniques.

DNA corresponding to amino acids 263 to 380 of human general receptor for phosphoinositides (Grp1) PH domain was isolated from a cDNA library using standard molecular biology and PCR cloning techniques. The resultant DNA fragment was sub-cloned into a pGEX 4T1 E. coli expression vector containing a GST epitope tag (Amersham Pharmacia Biotech, Rainham, Essex, UK) as described by Gray et al., *Analytical Biochemistry,* 2003, 313: 234-245). The GST-tagged Grp1 PH domain was expressed and purified using standard techniques.

Test compounds were prepared as 10 mM stock solutions in DMSO and diluted into water as required to give a range of final assay concentrations. Aliquots (2 μl) of each compound dilution were placed into a well of a Greiner 384-well low volume (LV) white polystyrene plate (Greiner Bio-one, Brunel Way, Stonehouse, Gloucestershire, UK Catalogue No. 784075). A mixture of each selected recombinant purified PI3K enzyme (15 ng), DiC8-PI(4,5)P2 substrate (40 μM; Cell Signals Inc , Kinnear Road, Columbus, USA, Catalogue No. 901), adenosine triphosphate (ATP; 4 μM) and a buffer solution [comprising Tris-HCl pH7.6 buffer (40 mM, 10 μl), 3-[(3-cholamidopropyl)dimethylammonio]-1-propane-sulfonate (CHAPS; 0.04%), dithiothreitol (DTT; 2 mM) and magnesium chloride (10 mM)] was agitated at room temperature for 20 minutes.

Control wells that produced a minimum signal corresponding to maximum enzyme activity were created by using 5% DMSO instead of test compound. Control wells that produced a maximum signal corresponding to fully inhibited enzyme were created by adding wortmannin (6 μM; Calbiochem/Merck Bioscience, Padge Road, Beeston, Nottingham, UK, Catalogue No. 681675) instead of test compound. These assay solutions were also agitated for 20 minutes at room temperature.

Each reaction was stopped by the addition of 10 μl of a mixture of EDTA (100 mM), bovine serum albumin (BSA, 0.045%) and Tris-HCl pH7.6 buffer (40 mM).

Biotinylated-DiC8-PI(3,4,5)P3 (50 nM; Cell Signals Inc., Catalogue No. 107), recombinant purified GST-Grp1 PH protein (2.5 nM) and AlphaScreen Anti-GST donor and acceptor beads (100 ng; Packard Bioscience Limited, Station Road, Pangbourne, Berkshire, UK, Catalogue No. 6760603M) were added and the assay plates were left for about 5 to 20 hours at room temperature in the dark. The resultant signals arising from laser light excitation at 680 nm were read using a Packard AlphaQuest instrument.

PI(3,4,5)P3 is formed in situ as a result of PI3K mediated phosphorylation of PI(4,5)P2. The GST-Grp1 PH domain protein that is associated with AlphaScreen Anti-GST donor beads forms a complex with the biotinylated PI(3,4,5)P3 that is associated with Alphascreen Streptavidn acceptor beads. The enymatically-produced PI(3,4,5)P3 competes with biotinylated PI(3,4,5)P3 for binding to the PH domain protein. Upon laser light excitation at 680 nm, the donor bead: acceptor bead complex produces a signal that can be measured. Accordingly, PI3K enzme activity to form PI(3,4,5)P3 and subsequent competition with biotinylated PI(3,4,5)P3 results in a reduced signal. In the presence of a PI3K enzyme inhibitor, signal strength is recovered.

PI3K enzyme inhibition for a given test compound was expressed as an $IC_{50}$ value.

(b)(ii) In Vitro PI3K Enzyme Assay (Echo)

The assay used AlphaScreen technology (Gray et al., Analytical Biochemistry, 2003, 313: 234-245) to determine the ability of test compounds to inhibit phosphorylation by recombinant Type I PI3K enzymes of the lipid PI(4,5)P2.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ respectively) were sub-cloned into a pDEST10 vector (Invitrogen Limited, Fountain Drive, Paisley, UK). The vector is a Gateway-adapted version of Fastbacl containing a 6-His epitope tag. A truncated form of Type Ib human PI3K p110γ isoform corresponding to amino acid residues 144-1102 (EMBL Accession No. X8336A) and the full length human p85α regulatory subunit (EMBL Accession No. HSP13KIN) were also sub-cloned into pFastBacl vector containing a 6-His epitope tag. The Type Ia p110 constructs were co-expressed with the p85α regulatory subunit. Following expression in the baculovirus system using standard baculovirus expression techniques, expressed proteins were purified using the His epitope tag using standard purification techniques.

DNA corresponding to amino acids 263 to 380 of human general receptor for phosphoinositides (Grp1) PH domain was isolated from a cDNA library using standard molecular biology and PCR cloning techniques. The resultant DNA fragment was sub-cloned into a pGEX 4T1 *E. coli* expression vector containing a GST epitope tag (Amersham Pharmacia Biotech, Rainham, Essex, UK) as described by Gray et al., *Analytical Biochemistry*, 2003, 313: 234-245). The GST-tagged Grp1 PH domain was expressed and purified using standard techniques.

Test compounds were prepared as 10 mM stock solutions in DMSO and diluted in DMSO to wateras required to give a range of final assay concentrations. Aliquots (120 nl2 μl) of each compound dilution were acoustically dispensed using a Labcyte Echo 550 placed into a well of a Greiner 384-well low volume (LV) white polystyrene plate (Greiner Bio-one, Brunel Way, Stonehouse, Gloucestershire, UK Catalogue No. 784075). A mixture of each selected recombinant purified PI3K enzyme (15 ng), DiC8-PI(4,5)P2 substrate (40 μM; Cell Signals Inc., Kinnear Road, Columbus, USA, Catalogue No. 901), adenosine triphosphate (ATP; 4 μM) and a buffer solution [comprising Tris-HCl pH7.6 buffer (40 mM, 10 μl), 3-[(3-cholamidopropyl)dimethylammonio]-1-propanesulfonate (CHAPS; 0.04%), dithiothreitol (DTT; 2 mM) and magnesium chloride (10 mM)] was agitated incubated at room temperature for 20 minutes.

Control wells that produced a minimum signal corresponding to maximum enzyme activity were created by using 1005% DMSO instead of test compound. Control wells that produced a maximum signal corresponding to fully inhibited enzyme were created by adding Wwortmannin (6 μM; Calbiochem/Merck Bioscience, Padge Road, Beeston, Nottingham, UK, Catalogue No. 681675) instead of test compound. These assay solutions were also incubatedagitated for 20 minutes at room temperature.

Each reaction was stopped by the addition of 10 10 μl of a mixture of EDTA (100 mM), bovine serum albumin (BSA, 0.045%) and Tris-HCl pH7.6 buffer (40 mM).

Biotinylated-DiC8-PI(3,4,5)P3 (50 nM; Cell Signals Inc., Catalogue No. 107), recombinant purified GST-Grp1 PH protein (2.5 nM) and AlphaScreen Anti-GST donor and acceptor beads (100 ng; Packard Bioscience Limited, Station Road, Pangbourne, Berkshire, UK, Catalogue No. 6760603M) were added and the assay plates were left for about 5 to overnight 20 hours at room temperature in the dark. The resultant signals arising from laser light excitation at 680 nm were read using a Packard AlphaQuest instrument.

PI(3,4,5)P3 is formed in situ as a result of PI3K mediated phosphorylation of PI(4,5)P2. The GST-Grp1 PH domain protein that is associated with AlphaScreen Anti-GST donor beads forms a complex with the biotinylated PI(3,4,5)P3 that is associated with Alphascreen Streptavidn acceptor beads. The enymatically-produced PI(3,4,5)P3 competes with biotinylated PI(3,4,5)P3 for binding to the PH domain protein. Upon laser light excitation at 680 nm, the donor bead : acceptor bead complex produces a signal that can be measured. Accordingly, PI3K enzme activity to form PI(3,4,5)P3 and subsequent competition with biotinylated PI(3,4,5)P3 results in a reduced signal. In the presence of a PI3K enzyme inhibitor, signal strength is recovered.

PI3K enzyme inhibition for a given test compound was expressed as an $IC_{50}$ value.

(c) In Vitro phospho-Ser473 Akt Assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning.

A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in DMEM containing 10% heat-inactivated FCS and 1% L-glutamine.

For the assay, the cells were detached from the culture flask using 'Accutase' (Innovative Cell Technologies Inc., San Diego, Calif., USA; Catalogue No. AT104) using standard tissue culture methods and resuspended in media to give $1.7 \times 10^5$ cells per mL. Aliquots (90 μl) were seeded into each of the inner 60 wells of a black Packard 96 well plate (PerkinElmer, Boston, Mass., USA; Catalogue No. 6005182) to give a density of ~15000 cells per well. Aliquots (90 μl) of culture media were placed in the outer wells to prevent edge effects. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and serially diluted as required with growth media to give a range of concentrations that were 10-fold the required final test concentrations. Aliquots (10 μl) of each compound dilution were placed in a well (in triplicate) to give the final required concentrations. As a minimum reponse control, each plate contained wells having a final concentration of 100 μM LY294002 (Calbiochem, Beeston, UK, Catalogue No. 440202). As a maximum response control, wells contained 1% DMSO instead of test compound. Following incubation, the contents of the plates were fixed by treatment with a 1.6% aqueous formaldehyde solution (Sigma, Poole, Dorset, UK, Catalogue No. F1635) at room temperature for 1 hour.

All subsequent aspiration and wash steps were carried out using a Tecan 96 well plate washer (aspiration speed 10 mm/sec). The fixing solution was removed and the contents of the plates were washed with phosphate-buffered saline (PBS; 50 μl; Gibco, Catalogue No. 10010015). The contents of the plates were treated for 10 minutes at room temperature with an aliquot (50 μl) of a cell permeabilisation buffer consisting of a mixture of PBS and 0.5% Tween-20. The 'permeabilisation' buffer was removed and non-specific binding sites were blocked by treatment for 1 hour at room temperature of an aliquot (50 μl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at room temperature with rabbit anti phospho-Akt (Ser473) antibody solution (50 μl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at room temperature with Alexafluor488 labelled goat anti-rabbit IgG (50 μl per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 μl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

(d) In Vitro MDA-MB-468 Human Breast Adenocarcinoma Proliferation Assay

This assay determines the ability of test compounds to inhibit cell proliferation as assessed using Cellomics Arrayscan technology. A MDA-MB-468 human breast adenocarcinoma cell line (LGC Promochem, Catalogue No. HTB-132) was routinely maintained as described in Biological Assay (b) herein.

For the proliferation assay, the cells were detached from the culture flask using Accutase and seeded into the inner 60 wells of a black Packard 96 well plate at a density of 8000 cells per well in 100 μl of complete growth media. The outer wells contained 100 μl of sterile PBS. The cells were incubated overnight at 37° C. with 5% $CO_2$ to allow them to adhere.

On day 2, the cells were treated with test compounds and incubated for 48 hours at 37° C. with 5% $CO_2$. Test compounds were prepared as 10 mM stock solutions in DMSO and serially diluted as required with growth media to give a range of test concentrations. Aliquots (50 μl) of each compound dilution were placed in a well and the cells were incubated for 2 days at 37° C. with 5% $CO_2$. Each plate contained control wells without test compound.

On day 4, BrdU labelling reagent (Sigma, Catalogue No. B9285) at a final dilution of 1:1000 was added and the cells were incubated for 2 hours at 37° C. The medium was removed and the cells in each well were fixed by treatment with 100 μl of a mixture of ethanol and glacial acetic acid (90% ethanol, 5% glacial acetic acid and 5% water) for 30 minutes at room temperature. The cells in each well were washed twice with PBS (100 μl). Aqueous hydrochloric acid (2M, 100 μl) was added to each well. After 20 minutes at room temperature, the cells were washed twice with PBS. Hydrogen peroxide (3%, 50 μl; Sigma, Catalogue No. H1009) was added to each well. After 10 minutes at room temperature, the wells were washed again with PBS.

BrdU incorporation was detected by incubation for 1 hour at room temperature with mouse anti-BrdU antibody (50 μl; Caltag, Burlingame, Calif., US; Catalogue No. MD5200) that was diluted 1:40 in PBS containing 1% BSA and 0.05% Tween-20. Unbound antibody was removed with two washes of PBS. For visualisation of incorporated BrdU, the cells were treated for 1 hour at room temperature with PBS (50 μl) and 0.05% Tween-20 buffer containing a 1:1000 dilution of Alexa fluor 488-labelled goat anti-mouse IgG. For visualisation of the cell nucleus, a 1:1000 dilution of Hoechst stain (Molecular Probes, Catalogue No. H3570) was added. Each plate was washed in turn with PBS. Subsequently, PBS (100 μl) was added to each well and the plates were analysed using a Cellomics array scan to assess total cell number and number of BrdU positive cells.

Fluorescence dose response data obtained with each compound were analysed and the degree of inhibition of MDA-MB-468 cell growth was expressed as an $IC_{50}$ value.

Although the pharmacological properties of the compounds of formula (I) vary with structural change as expected, in general, it is believed that activity possessed by compounds of formula (I) may be demonstrated at the following concentrations or doses in one or more of the above tests (a) to (d):

Test (a)(i):—$IC_{50}$ versus mTOR kinase at less than 10 μM, in particular 0.001-0.5 μM for many compounds; for example 1b the IC50 was measured, the values was 0.55 μM.

Test (b)(i):—$IC_{50}$ versus p110γ Type Ib human PI3K at less than 10 μM, in particular 0.001-0.5 μM for many compounds; and $IC_{50}$ versus p110α Type Ia human PI3K at less than 10 μM, in particular 0.001-0.5 μM for many compounds;

for example 1b the IC50 was measured on three occasions, the values were 39.75, 11.74 and 3.20 μM.

Test (c):—$IC_{50}$ versus Serine 473 in Akt at less than 10 μM, in particular 0.1-20 μM for many compounds); for example 1b the IC50 was measured on two occasions, the values were 1.93 and 1.74 μM;

Test (d):—$IC_{50}$ at less than 20 μM;

The following examples were tested in enzyme assay Test (a)(ii):

| Ex No. | Test (a)(ii) $IC_{50}$ (μM) |
| --- | --- |
| 1a | 0.0177 |
| 1 | 0.0197 |
| 1d | 0.0215 |
| 1b | 0.0816 |
| 1c | 0.0688 |
| 2 | 0.00477 |
| 2a | 0.0051 |
| 2b | 0.0068 |
| 2c | 0.000828 |
| 2d | 0.305 |
| 3 | 0.011 |
| 3a | 0.00717 |
| 3b | 0.0124 |
| 3c | 0.00308 |
| 4a | 0.0155 |
| 4b | 0.154 |
| 4 | 0.161 |
| 4c | 0.0585 |
| 5 | 0.0079 |
| 5a | 0.0367 |
| 5b | 0.0384 |
| 5c | 0.0374 |

The compounds of the present invention are advantageous in that they possess pharmacological activity. In particular, the compounds of the present invention modulate (in particular, inhibit) mTOR kinase and/or phosphatidylinositol-3-kinase (PI3K) enzymes, such as the Class Ia PI3K enzymes (e.g. PI3Kalpha, PI3Kbeta and PI3Kdelta) and the Class Ib PI3K enzyme (PI3Kgamma). More particularly compounds of the present invention modulate (in particular, inhibit) mTOR kinase. More particularly compounds of the present invention modulate (in particular, inhibit) one or more PI3K enzyme. The inhibitory properties of compounds of formula (I) may be demonstrated using the test procedures set out herein and in the experimental section. Accordingly, the compounds of formula (I) may be used in the treatment (therapeutic or prophylactic) of conditions/diseases in human and non-human animals which are mediated by mTOR kinase and/or one or more PI3K enzyme(s), and in particular by mTOR kinase.

The invention also provides a pharmaceutical composition comprising a compound of formula (I), or a pharmaceutically acceptable salt thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of formula I will naturally vary according to the nature and severity of the disease state, the age and sex of the animal or patient and the route of administration, according to well known principles of medicine.

In using a compound of formula (I) for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Typically, unit dosage forms will contain about 10 mg to 0.5 g of a compound of this invention.

As stated herein, it is known that mTOR kinase and the PI3K enzymes have roles in tumourigenesis as well as numerous other diseases. We have found that the compounds of formula (I) possess potent anti-tumour activity which it is believed is obtained by way of inhibition of mTOR kinase and/or one or more of the PI3K enzymes.

Accordingly, the compounds of the present invention are of value as anti-tumour agents. Particularly, the compounds of the present invention are of value as anti-proliferative, apoptotic and/or anti-invasive agents in the containment and/or treatment of solid and/or liquid tumour disease. Particularly, the compounds of the present invention are expected to be useful in the prevention or treatment of those tumours which are sensitive to inhibition of mTOR and/or one or more of the PI3K enzymes such as the Class Ia PI3K enzymes and the Class Ib PI3K enzyme. Further, the compounds of the present invention are expected to be useful in the prevention or treatment of those tumours which are mediated alone or in part by mTOR and/or one or more of the PI3K enzymes such as the Class Ia PI3K enzymes and the Class Ib PI3K enzyme. The compounds may thus be used to produce an mTOR enzyme inhibitory effect in a warm-blooded animal in need of such treatment. Certain compounds may be used to produce an PI3K enzyme inhibitory effect in a warm-blooded animal in need of such treatment.

As stated herein, inhibitors of mTOR kinase and/or one or more PI3K enzymes should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

According to a further aspect of the invention there is provided a compound of formula (I), or a pharmaceutically acceptable salt thereof, as defined herein for use as a medicament in a warm-blooded animal such as man.

According to a further aspect of the invention, there is provided a compound of formula (I), or a pharmaceutically acceptable salt thereof, as defined herein for use in the production of an anti-proliferative effect in a warm-blooded animal such as man.

According to a further aspect of the invention, there is provided a compound of formula (I), or a pharmaceutically acceptable salt thereof, as defined herein for use in the production of an apoptotic effect in a warm-blooded animal such as man.

According to a further feature of the invention there is provided a compound of formula (I), or a pharmaceutically acceptable salt thereof, as defined herein for use in a warm-blooded animal such as man as an anti-invasive agent in the containment and/or treatment of proliferative disease such as cancer.

According to a further aspect of the invention, there is provided the use of a compound of formula (I), or a pharmaceutically acceptable salt thereof, as defined herein for the production of an anti-proliferative effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an anti-proliferative effect in a warm-blooded animal such as man.

According to a further aspect of the invention, there is provided the use of a compound of formula (I), or a pharmaceutically acceptable salt thereof, as defined herein for the production of an apoptotic effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an apoptotic effect in a warm-blooded animal such as man.

According to a further feature of the invention there is provided the use of a compound of formula (I), or a pharmaceutically acceptable salt thereof, as defined herein in the manufacture of a medicament for use in a warm-blooded animal such as man as an anti-invasive agent in the containment and/or treatment of proliferative disease such as cancer.

According to a further feature of this aspect of the invention there is provided a method for producing an anti-proliferative effect in a warm-blooded animal, such as man, in need of such treatment which comprises administering to said animal an effective amount of a compound of formula (I), or a pharmaceutically acceptable salt thereof, as defined herein.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a compound of formula (I), or a pharmaceutically acceptable salt thereof, as defined herein.

According to a further aspect of the invention there is provided the use of a compound of formula (I), or a pharmaceutically acceptable salt thereof, as defined herein in the manufacture of a medicament for use in the prevention or treatment of proliferative disease such as cancer in a warm-blooded animal such as man.

According to a further feature of this aspect of the invention there is provided a method for the prevention or treatment of proliferative disease such as cancer in a warm-blooded animal, such as man, in need of such treatment which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided the use of a compound of formula (I), or a pharmaceutically acceptable salt thereof, as defined herein in the manufacture of a medicament for use in the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of mTOR kinase and/or one or more PI3K enzymes (such as the Class Ia enzymes and/or the Class Ib PI3K enzyme) that are involved in the signal transduction steps which lead to the proliferation, survival, invasiveness and migratory ability of tumour cells which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in providing a mTOR kinase inhibitory effect and/or a PI3K enzyme inhibitory effect (such as a Class Ia PI3K enzyme or Class Ib PI3K enzyme inhibitory effect).

According to a further feature of this aspect of the invention there is provided the use of a compound of formula (I), or a pharmaceutically acceptable salt thereof, as defined herein in the manufacture of a medicament for use in providing a mTOR kinase inhibitory effect and/or a PI3K enzyme inhibitory effect (such as a Class Ia PI3K enzyme or Class Ib PI3K enzyme inhibitory effect).

According to a further aspect of the invention there is also provided a method for providing a mTOR kinase inhibitory effect and/or a PI3K enzyme inhibitory effect (such as a Class Ia PI3K enzyme or Class Ib PI3K enzyme inhibitory effect) which comprises administering an effective amount of a compound of formula I, or a pharmaceutically acceptable salt thereof, as defined herein.

According to a further feature of the invention there is provided a compound of formula I, or a pharmaceutically acceptable salt thereof, as defined herein for use in the treatment of cancer, inflammatory diseases, obstructive airways diseases, immune diseases or cardiovascular diseases.

According to a further feature of the invention there is provided a compound of formula I, or a pharmaceutically acceptable salt thereof, as defined herein for use in the treatment of solid tumours such as carcinoma and sarcomas and the leukaemias and lymphoid malignancies.

According to a further feature of the invention there is provided a compound of formula I, or a pharmaceutically acceptable salt thereof, as defined herein for use in the treatment of cancer of the breast, colorectum, lung (including small cell lung cancer, non-small cell lung cancer and bronchioalveolar cancer) and prostate.

According to a further feature of the invention there is provided a compound of formula (I), or a pharmaceutically acceptable salt thereof, as defined herein for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided the use of a compound of formula (I), or a pharmaceutically acceptable salt thereof, as defined herein in the manufacture of a medicament for use in the treatment of cancer, inflammatory diseases, obstructive airways diseases, immune diseases or cardiovascular diseases.

According to a further feature of the invention there is provided the use of a compound of formula (I), or a pharmaceutically acceptable salt thereof, as defined herein in the manufacture of a medicament for use in the treatment of solid tumours such as carcinoma and sarcomas and the leukaemias and lymphoid malignancies.

According to a further feature of the invention there is provided the use of a compound of formula (I), or a pharmaceutically acceptable salt thereof, as defined herein in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a compound of formula (I), or a pharmaceutically acceptable salt thereof, as defined herein in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a compound of formula (I), or a pharmaceutically acceptable salt thereof, as defined herein.

According to a further feature of the invention there is provided a method for treating solid tumours such as carcinoma and sarcomas and the leukaemias and lymphoid malignancies in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a compound of formula (I), or a pharmaceutically acceptable salt thereof, as defined herein.

As stated herein, the in vivo effects of a compound of formula (I) may be exerted in part by one or more metabolites that are formed within the human or animal body after administration of a compound of formula (I).

The invention further relates to combination therapies wherein a compound of formula (I), or a pharmaceutically acceptable salt thereof, or a pharmaceutical composition or formulation comprising a compound of formula (I) is administered concurrently or sequentially or as a combined preparation with another treatment of use in the control of oncology disease.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment of cancer.

Suitable agents to be used in combination include:—
(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);
(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat and inhibitors of urokinase plasminogen activator receptor function);
(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Aid kinases;
(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];
(vi) vascular damaging agents such as combretastatin A4 and compounds disclosed in International Patent Applications WO 99/02166, WO 00/40529, WO 00/41669, WO 01/92224, WO 02/04434 and WO 02/08213;
(vii) antisense therapies, for example those which are directed to the targets listed above, such as ISIS 2503, an anti-ras antisense agent;
(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be further explained by reference to the following illustrative examples.

Unless stated otherwise, starting materials were commercially available. All solvents and commercial reagents were of laboratory grade and were used as received.

In the examples $^1$H NMR spectra were recorded on a Bruker DPX 300 (300 MHz), Bruker DRX 400 (400 MHz) instrument or a Bruker DRX 500 (500 MHz) instrument. The central peaks of chloroform-d ($\delta_H$ 7.27 ppm), dimethylsulfoxide-d$_6$ ($\delta_H$ 2.50 ppm) or acetone-d$_6$ ($\delta_H$ 2.05 ppm) were used as internal references. The following abbreviations have been used: s, singlet; d, doublet;
t, triplet; q, quartet; m, multiplet; br, broad.

Column chromatography was carried out using silica gel (0.04-0.063 mm, Merck). In general, a Kromasil KR-100-5-C18 reversed-phase column (250×20 mm, Akzo Nobel) was used for preparative HPLC with mixtures of acetonitrile and water [containing 0.1% trifluoroacetic acid (TFA)] used as the eluent at a flow rate of 10 mL/min.

The following methods were used for liquid chromatography (LC)/mass spectral (MS) analysis:—

| HPLC: | Agilent 1100 or Waters Alliance HT (2790 & 2795) |
|---|---|
| Mass Spectrometer: | Waters ZQ ESCi |

HPLC Column

The standard HPLC column used is the Phemonenex Gemini C18 5☐82 m, 50×2 mm.

Acidic HPLC Methods

| The mobile phases used are: | Mobile phase A: | Water |
|---|---|---|
| | Mobile Phase B: | Acetonitrile |
| | Mobile Phase C: | 1% Formic Acid in 50:50 Water:MeCN (v/v) |

Each method is followed by a rapid equilibration using a 5 mL flow rate for 0.45 min.

Four Generic HPLC Methods are Available:

5 Minute Monitor Acidic method

| Time/ min | Mobile Phase A: | Mobile Phase B: | Mobile Phase C: | Curve | Flow Rate/ mL/min |
|---|---|---|---|---|---|
| 0.00 | 95 | 0 | 5 | 1 | 1.1 |
| 4 | 0 | 95 | 5 | 6 | 1.1 |
| 4.5 | 0 | 95 | 5 | 6 | 1.1 |

Early Acidic Method for Early Eluting Compounds

| Time/ min | Mobile Phase A: | Mobile Phase B: | Mobile Phase C: | Curve | Flow Rate/ mL/min |
|---|---|---|---|---|---|
| 0.00 | 95 | 0 | 5 | 1 | 1.1 |
| 4 | 57.5 | 37.5 | 5 | 6 | 1.1 |
| 4.5 | 57.5 | 37.5 | 5 | 6 | 1.1 |

Mid Acidic Method for Middle Eluting Compounds

| Time/ min | Mobile Phase A: | Mobile Phase B: | Mobile Phase C: | Curve | Flow Rate/ mL/min |
|---|---|---|---|---|---|
| 0.00 | 95 | 0 | 5 | 1 | 1.1 |
| 0.01 | 67.5 | 27.5 | 5 | 6 | 1.1 |
| 4.5 | 27.5 | 67.5 | 5 | 6 | 1.1 |

Late Acidic Method for Late Eluting Compounds

| Time/ min | Mobile Phase A: | Mobile Phase B: | Mobile Phase C: | Curve | Flow Rate/ mL/min |
|---|---|---|---|---|---|
| 0.00 | 95 | 0 | 5 | 1 | 1.1 |
| 0.01 | 27.5 | 67.5 | 5 | 6 | 1.1 |
| 4.5 | 5 | 95 | 5 | 6 | 1.1 |

Basic HPLC Methods

In some instances the standard acidic methods may be unsuitable for either the compound ionisation or the chromatography separation required. In such cases four comparable Basic HPLC methods are available.

| The mobile phases used are: | Mobile phase A: | Water |
|---|---|---|
| | Mobile Phase B: | Acetonitrile |
| | Mobile Phase D: | 0.1% 880 Ammonia in acetonitrile |

Each method is followed by a rapid equilibration using a 5 mL flow rate for 0.45 min.

Minute Monitor Basic Method

| Time/ min | Mobile Phase A: | Mobile Phase B: | Mobile Phase D: | Curve | Flow Rate/ mL/min |
|---|---|---|---|---|---|
| 0.00 | 95 | 0 | 5 | 1 | 1.1 |
| 4 | 0 | 95 | 5 | 6 | 1.1 |
| 4.5 | 0 | 95 | 5 | 6 | 1.1 |

Early Basic Method for Early Eluting Compounds

| Time/ min | Mobile Phase A: | Mobile Phase B: | Mobile Phase D: | Curve | Flow Rate/ mL/min |
|---|---|---|---|---|---|
| 0.00 | 95 | 0 | 5 | 1 | 1.1 |
| 4 | 57.5 | 37.5 | 5 | 6 | 1.1 |
| 4.5 | 57.5 | 37.5 | 5 | 6 | 1.1 |

Mid Basic Method for Middle Eluting Compounds

| Time/ min | Mobile Phase A: | Mobile Phase B: | Mobile Phase D: | Curve | Flow Rate/ mL/min |
|---|---|---|---|---|---|
| 0.00 | 95 | 0 | 5 | 1 | 1.1 |
| 0.01 | 67.5 | 27.5 | 5 | 6 | 1.1 |
| 4.5 | 27.5 | 67.5 | 5 | 6 | 1.1 |

Late Basic Method for Late Eluting Compounds

| Time/ min | Mobile Phase A: | Mobile Phase B: | Mobile Phase C: | Curve | Flow Rate/ mL/min |
|---|---|---|---|---|---|
| 0.00 | 95 | 0 | 5 | 1 | 1.1 |
| 0.01 | 27.5 | 67.5 | 5 | 6 | 1.1 |
| 4.5 | 5 | 95 | 5 | 6 | 1.1 |

The following method was used for liquid chromatography (LC)/mass spectral (MS) analysis:—Instrument: Agilent 1100; Column: Waters 'Symmetry' 2.1×30 mm; Mass Spectral analysis using chemical ionisation (APCI); Flow rate: 0.7 mL/min; Absorption Wavelength: 254 nm; Solvent A: water+ 0.1% TFA; Solvent B: acetonitrile+0.1% TFA; Solvent Gradient: 15-95% Solvent B for 2.7 minutes followed by 95% Solvent B for 0.3 minutes.

The following methods were used for LC analysis:—

Method A:—Instrument: Agilent 1100; Column: Kromasil C18 reversed-phase silica, 100×3 mm, 5 μm particle size; Solvent A: 0.1% TFA/water, Solvent B: 0.08% TFA/acetonitrile; Flow Rate: 1 mL/min; Solvent Gradient: 10-100% Solvent B for 20 minutes followed by 100% Solvent B for 1 minute; Absorption Wavelengths: 220, 254 and 280 nm. In general, the retention time of the product was noted.

Method B:—Instrument: Agilent 1100; Column: Waters 'Xterra' C8 reversed-phase silica, 100×3 mm, 5 μm particle size; Solvent A: 0.015M ammonia in water, Solvent B: acetonitrile; Flow Rate: 1 ml/min, Solvent Gradient: 10-100% Solvent B for 20 minutes followed by 100% Solvent B for 1 minute; Absorption Wavelength: 220, 254 and 280 nm. In general, the retention time of the product was noted.

The following abbreviations are used herein or within the following illustrative examples:—

HPLC High Performance Liquid Chromatography
HBTU O-(benzotriazol-1-yl)-N,N,N',N'-tetramethyluronium hexafluorophosphate;
HATU O-(7-azabenzotriazol-1-yl)-N,N,N',N'-tetramethyluronium hexafluorophosphate;
HOBT 1-hydroxybenzotriazole;
HOAT 1-hydroxy-7-azabenzotriazole;
NMP N-methylpyrrolidin-2-one;
DMSO dimethylsulfoxide;
DMF N,N-dimethylformamide;
DMA N,N-dimethylacetamide;
THF tetrahydrofuran;
DME 1,2-dimethoxyethane;
DCCI dicyclohexylcarbodiimide;
MeOH methanol;
MeCN acetonitrile;
DCM dichloromethane;
DIPEA N,N-diisopropylethylamine;
DBU 1,8-diazabicyclo[5.4.0]undec-7-ene;
RT room temperature (approximately 17 to 25° C.);
tR retention time;
m/z mass/charge ratio.

The chemical names were generated by software which used the Lexichem Toolkit (v. 1.60) from OpenEye Scientific Software (www.eyesopen.com) to generate IUPAC conforming names.

EXAMPLE 1

3-Cyclopropyl-1-[4-[4-[(3S)-3-methylmorpholin-4-yl]-6-(methylsulfonylmethyl)pyrimidin-2-yl]phenyl]thiourea

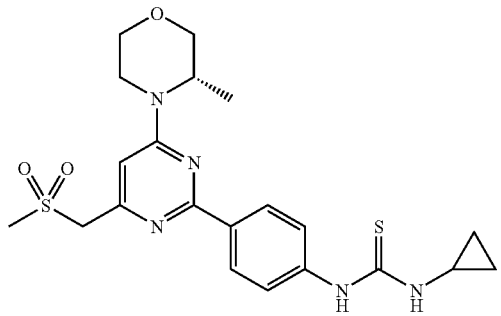

Diimidazol-1-ylmethanethione (55 mg, 0.28 mmol) was dissolved in DCM (1 mL) and the solution added to a stirred solution of 4-[4-[(3S)-3-methylmorpholin-4-yl]-6-(methylsulfonylmethyl)pyrimidin-2-yl]aniline (100 mg, 0.28 mmol) in DCM (1.5 mL) at RT. After stirring for 90 minutes triethylamine (0.039 mL, 0.28 mmol) and cyclopropylamine (0.096 mL, 1.38 mmol) were added and the mixture was stirred at RT for 2 hours. The reaction was evaporated to dryness and purified by flash chromatography on silica, eluting with 0-4% methanol in DCM. The material was further purified by prep HPLC to give the desired material as a white solid (60 mg).

NMR Spectrum: $^1$H NMR (400.13 MHz, DMSO-$d_6$) δ 0.58-0.62 (2H, m), 0.74-0.79 (2H, m), 1.25 (3H, d), 3.21 (3H, s), 3.23-3.28 (1H, m), 3.48-3.54 (1H, m), 3.64-3.68 (1H, m), 3.78 (2H, d), 3.97-4.01 (2H, m), 4.18 (1H, d), 4.51 (2H, s), 6.83 (1H, s), 7.62-7.65 (2H, m), 8.25-8.29 (2H, m), 9.52 (1H, s)

LCMS Spectrum: MH+ 462, Retention Time 1.65 min, Method Monitor Acid The following compounds were made in an analogous manner from 4-[4-[(3S)-3-methylmorpholin-4-yl]-6-(methylsulfonylmethyl)pyrimidin-2-yl]aniline and the appropriate amine.

| Example | Structure | NAME | LCMS MH+ | Retention Time (min) |
|---|---|---|---|---|
| 1a* | 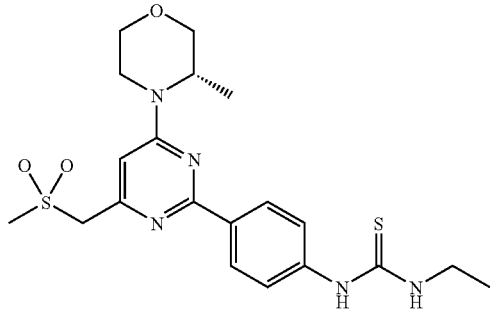 | 3-ethyl-1-[4-[4-[(3S)-3-methylmorpholin-4-yl]-6-(methylsulfonylmethyl)pyrimidin-2-yl]phenyl]thiourea | 450 | 1.70 |

-continued

| Example | Structure | NAME | LCMS MH+ | Retention Time (min) |
|---|---|---|---|---|
| 1b | | 1-[4-[4-[(3S)-3-methylmorpholin-4-yl]-6-(methylsulfonylmethyl)pyrimidin-2-yl]phenyl]-3-phenyl-thiourea | 498 | 2.07 |
| 1c | | 3-(4-methoxyphenyl)-1-[4-[4-[(3S)-3-methylmorpholin-4-yl]-6-(methylsulfonyl-methyl)pyrimidin-2-yl]phenyl]thiourea | 528 | 2.01 |
| 1d | | 3-(4-fluorophenyl)-1-[4-[4-[(3S)-3-methylmorpholin-4-yl]-6-(methylsulfonylmethyl)pyrimidin-2-yl]phenyl]thiourea | 516 | 2.09 |

*Not purified by prep HPLC

EXAMPLE 1a $^1$H NMR (400.13 MHz, DMSO-d$_6$) δ 1.14 (3H, t), 1.25 (3H, d), 3.21 (3H, s), 3.23-3.27 (1H, m), 3.48-3.53 (2H, m), 3.50-3.54 (1H, m), 3.64-3.67 (1H, m), 3.78 (1H, d), 3.97-4.01 (1H, m), 4.15-4.19 (1H, m), 4.50 (3H, s), 6.82 (1H, s), 7.56-7.59 (2H, m), 7.89 (1H, s), 8.25-8.29 (2H, m), 9.63 (1H, s)

EXAMPLE 1b $^1$H NMR (400.13 MHz, DMSO-d$_6$) δ 1.25 (3H, d), 3.21 (3H, s), 3.24 (1H, m), 3.48-3.54 (1H, m), 3.64-3.68 (1H, m), 3.78 (1H, d), 3.97-4.01 (1H, m), 4.18 (1H, d), 4.50 (2H, s), 4.51 (1H, s), 6.83 (1H, s), 7.12-7.17 (1H, m), 7.32-7.37 (2H, m), 7.51 (2H, s), 7.66 (2H, s), 8.27-8.30 (2H, m), 9.89 (1H, s), 9.98 (1H, s)

EXAMPLE 1c $^1$H NMR (400.13 MHz, DMSO-d$_6$) δ 1.25 (3H, d), 3.21 (3H, s), 3.24 (1H, m), 3.48-3.54 (1H, m), 3.64-3.68 (1H, m), 3.76 (3H, s), 3.78 (1H, d), 3.97-4.01 (1H, m), 4.18 (1H, d), 4.50 (2H, s), 4.51 (1H, s), 6.82 (1H, s), 6.90-6.94 (2H, m), 7.36 (2H, d), 7.65 (2H, d), 8.28 (2H, d), 9.71 (1H, s), 9.83 (1H, s)

EXAMPLE 1d $^1$H NMR (400.13 MHz, DMSO-d$_6$) δ 1.25 (3H, d), 3.21 (3H, s), 3.24 (1H, d), 3.48-3.54 (1H, m), 3.64-3.68 (1H, m), 3.77 (1H, d), 3.97-4.01 (1H, m), 4.18 (1H, d), 4.51 (2H, s), 4.51 (1H, s), 6.83 (1H, s), 7.15-7.21 (2H, m), 7.46-7.52 (2H, m), 7.63-7.69 (2H, m), 8.28-8.32 (2H, m), 9.85 (1H, s), 9.99 (1H, s)

The preparation of 4-[4-[(3S)-3-methylmorpholin-4-yl]-6-(methylsulfonylmethyl)pyrimidin-2-yl]aniline is described below.

4-[4-[(3S)-3-Methylmorpholin-4-yl]-6-(methylsulfonylmethyl)pyrimidin-2-yl]aniline

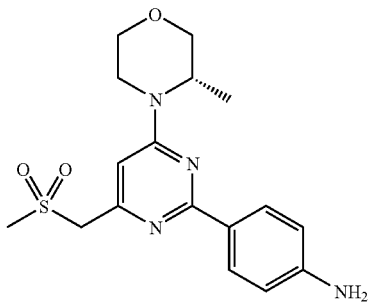

tert-Butyl N-[4-[4-[(3S)-3-methylmorpholin-4-yl]-6-(methylsulfonylmethyl)pyrimidin-2-yl]phenyl]carbamate (1.09 g, 2.35 mmol) was dissolved in methanol (5 mL) and 4M hydrogenchloride in dioxane (5 mL) was added. The solution was stirred at room temperature overnight, then the mixture evaporated to a dark brown oil and dissolved in ethyl acetate (10 mL). Water (5 mL) was added followed by the addition of sodium bicarbonate solution until neutral pH was achieved (~2 mL). The phases were separated and the organic phase washed with water (10 mL). The organic layer was dried over magnesium sulphate and evaporated to a pale yellow foam (805 mg).

NMR Spectrum: $^1$H NMR (399.9 MHz, DMSO-$d_6$) δ 1.23 (3H, d), 3.31 (3H, s), 3.5 (1H, m), 3.64 (1H, m), 3.78 (1H, m), 4.13 (1H, m), 4.49 (2H, m), 5.57 (2H, s), 6.61 (2H, d), 6.68 (1H, s), 8.08 (1H, d)

LCMS Spectrum: MH+ 363, retention time 1.02 min, Method 5 Min Acid tert-Butyl N-[4-[4-[(3S)-3-methylmorpholin-4-yl]-6-(methylsulfonylmethyl)pyrimidin-2-yl]phenyl]carbamate

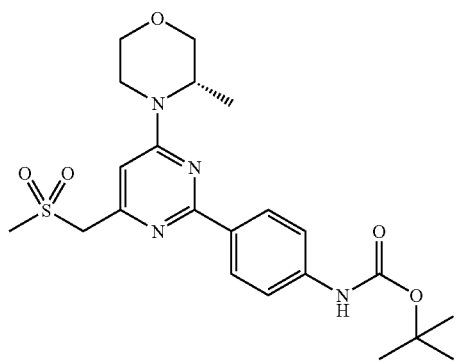

2-Chloro-4-[(3S)-3-methylmorpholin-4-yl]-6-(methylsulfonylmethyl)pyrimidine (1.0 g, 3.27 mmol) was dissolved in a solution of 18% DMF in a mixture of 7:3:2 DME:water:ethanol (7 mL). [4-[(2-Methylpropan-2-yl)oxycarbonylamino]phenyl]boronic acid (1.165 g, 4.91 mmol), 2M sodium carbonate solution (4 mL) and dichlorobis(triphenylphosphine)palladium catalyst (115 mg, 0.16 mmol) were then added to the solution and refluxed at 90° C. for 5 hours under nitrogen atmosphere. The reaction was allowed to cool to room temp then partitioned between ethyl acetate and water. The organics were dried over magnesium sulphate, filtered and concentrated to dryness. The crude oil was dissolved in dichloromethane and filtered to remove insoluble material. A beige solid precipitated from the filtrates and the filtrates were filtered again. The solid was analysed and found to be the excess boronic acid and the filtrates contained the product and some impurities. The filtrates were purified by chromatography on silica, eluting with 0-40% ethyl acetate in isohexane, to give the desired compound as an orange oil (530 mg).

LCMS Spectrum: MH+ 463, retention time 2.23 min, Method 5 Min Acid

2-Chloro-4-[(3S)-3-methylmorpholin-4-yl]-6-(methylsulfonylmethyl)pyrimidine

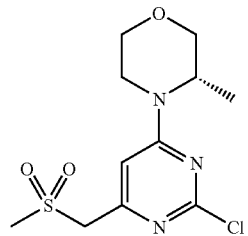

2,4-Dichloro-6-(methylsulfonylmethyl)pyrimidine (30 g, 0.13 mol) was dissolved in dichloromethane and stirred (under nitrogen) at −5° C. Triethylamine (17.4 mL, 0.13 mol) was added to give a clear brown solution. (3S)-3-Methylmorpholine was dissolved in dichloromethane and added dropwise keeping the reaction below −5° C. The cooling bath was then removed and the mixture stirred for 1 hour. The reaction mixture was heated at reflux for 2 hours, then the reaction mixture was washed with water, dried then evaporated. The crude material was purified by preparative HPLC to give the desired material as a to solid (19.3 g).

NMR Spectrum: $^1$H NMR (400.13 MHz, DMSO-$d_6$) δ1.21-1.23 (m, 3H), 3.11 (s, 3H), 3.19-3.26 (m, 1H), 3.42-3.49 (m, 1H), 3.58-3.62 (1H, m), 3.73 (d, 1H), 3.92-3.96 (m, 2H), 4.27-4.31 (m, 1H), 4.45 (s, 2H), 6.92 (s, 1H)

LCMS Spectrum: MH+ 306, retention time 1.42 min, Method 5 Min Acid

2,4-Dichloro-6-(methylsulfonylmethyl)pyrimidine

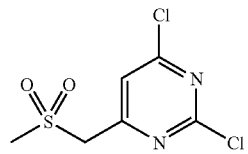

6-(Methylsulfonylmethyl)-1H-pyrimidine-2,4-dione (132 g, 0.65 mol) was added to phosphorus oxychloride (1.2 L) and the mixture heated to reflux for 16 hours, then cooled to room temperature. The excess phosphorus oxychloride was removed in vacuo, the residue azeotroped with toluene (2×500 mL) and dissolved in dichloromethane. This mixture was then poured slowly onto ice (4 L) and stirred for 20 minutes, then extracted with dichloromethane (3×1 L) (the insoluble black material was filtered off and discarded) and ethyl acetate (2×1 L). The extracts were combined, dried, then evaporated to leave the desired material as a dark brown solid (51 g). The material was used without further purification.

NMR Spectrum: $^1$H NMR (400.13 MHz, DMSO-$d_6$) δ 3.13 (s, 3H), 4.79 (s, 2H), 7.87 (s, 1H)

LCMS Spectrum: MH+ 239, retention time 1.21 min, Method 5 Min Acid 6-(Methylsulfonylmethyl)-1H-pyrimidine-2,4-dione

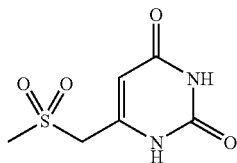

6-(Chloromethyl)-1H-pyrimidine-2,4-dione (175 g, 1.09 mol) was dissolved in DMF (2 L) and methanesulphinic acid sodium salt (133.5 g, 1.31 mol) was added. The reaction was heated to 125° C. for 2 hours then allowed to cool and the suspension filtered and concentrated in vacuo to give a yellow solid. The crude material was washed with water, filtered, then triturated with toluene. The solid was filtered then triturated with isohexane to leave the desired compound as a yellow solid (250 g). The material was used without further purification.

6-(Chloromethyl)-1H-pyrimidine-2,4-dione is a commercially available material.

2-Chloro-4-[(3S)-3-methylmorpholin-4-yl]-6-(methylsulfonylmethyl)pyrimidine can also be prepared by the method described below.

2-Chloro-4-[(3S)-3-methylmorpholin-4-yl]-6-(methylsulfonylmethyl)pyrimidine

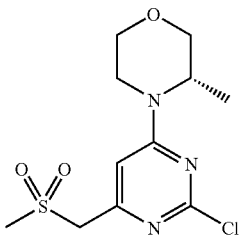

Methanesulfinic acid, sodium salt (11.75 g, 115.11 mmol) was added in one portion to 2-chloro-4-(iodomethyl)-6-[(3S)-3-methylmorpholin-4-yl]pyrimidine (37 g, 104.64 mmol), in acetonitrile (900 mL) and the resulting solution stirred at 85° C. for 24 hours. The organic layers were combined and washed with water (3×100 mL), dried over MgSO$_4$, filtered, and the solvent was removed by evaporation to give the crude product as a dark brown oil, which solidifed (36 g). The crude solid was purified by flash silicachromatography, elution gradient 0 to 30% ethyl acetate in DCM, to give the desired material (22 g) as a cream solid which was identical to previous samples.

2-Chloro-4-(iodomethyl)-6-[(3S)-3-methylmorpholin-4-yl]pyrimidine

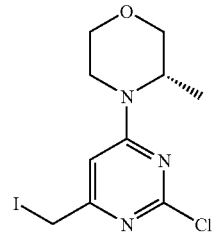

Methanesulfonyl chloride (0.245 mL, 3.14 mmol) was added dropwise over a period of 5 minutes to a solution of triethylamine (0.875 mL, 6.28 mmol) and [2-chloro-6-[(3S)-3-methylmorpholin-4-yl]pyrimidin-4-yl]methanol (510 mg, 2.09 mmol) in DCM (30 mL) at 0° C. under nitrogen. The resulting solution was stirred at RT for 45 minutes. The reaction mixture was diluted with water (20 mL). The organic layer was dried (MgSO$_4$) and filtered. Sodium Iodide (1569 mg, 10.46 mmol) was added and the reaction was heated to 50° C. for 20 hours. The reaction mixture was filtered and evaporated to afford the desired material (761 mg).

NMR Spectrum: $^1$H NMR (400.132 MHz, DMSO) δ 1.19-1.25 (3H, m), 3.18-3.22 (1H, m), 3.40-3.47 (1H, m), 3.57-3.60 (1H, m), 3.71 (1H, d), 3.90-3.94 (1H, m), 3.96-3.98 (1H, m), 4.28-4.32 (3H, m), 6.94 (1H, s).

LCMS Spectrum: m/z (ESI+) (M+H)+=354; HPLC tR=2.10 min.

2-Chloro-4-(iodomethyl)-6-[(3S)-3-methylmorpholin-4-yl]pyrimidine can also be prepared by the dropwise addition of methanesulfonyl chloride (91 mL, 1169.52 mmol) to [2-chloro-6-[(3S)-3-methylmorpholin-4-yl]pyrimidin-4-yl] methanol (190 g, 779.68 mmol) and triethylamine (163 mL, 1169.52 mmol) in DCM (2293 mL) at 0° C. under air. The resulting solution was allowed to warm up slowly to RT over a period of 4 hours. The reaction mixture was quenched with water, extracted with DCM and the organic layer dried over MgSO$_4$, filtered and evaporated to afford [2-chloro-6-[(3S)-3-methylmorpholin-4-yl]pyrimidin-4-yl]methyl methanesulfonate as a yellow gum (251 g). Sodium iodide (234 g, 1560.07 mmol) was added to this material in acetone (3679 mL) and the resulting suspension stirred at RT for 16 hours. The reaction mixture was evaporated to dryness and redissolved in DCM and washed three times with water then with a saturated aqueous solution of sodium thiosulphate. The organic layer was dried over MgSO$_4$, filtered and evaporated to afford crude desired product (270 g). This was purified by chromatography to give an off white solid which was further triturated with ether to give the desired material which was identical to previous samples.

[2-Chloro-6-[(3S)-3-methylmorpholin-4-yl]pyrimidin-4-yl]methanol

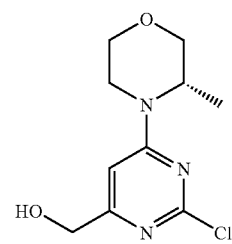

Methyl 2-chloro-6-[(3S)-3-methylmorpholin-4-yl]pyrimidine-4-carboxylate (3.15 g) was dissolved in dry THF (20 mL) and cooled to 0° C. under nitrogen. A solution of lithium borohydride (2.0M in THF, 6.09 mL) was added dropwise and the solution allowed to warm to RT and stirred for 1 hour. The reaction was quenched with water (20 mL) then evaporated to dryness, the residue dissolved in ethyl acetate (150 mL) and washed with water (150 mL) followed by brine (50 mL). The organics were evaporated to dryness to give to the desired material as a white solid (2.44 g).

NMR Spectrum: $^1$H NMR (400.132 MHz, DMSO) δ 1.20-1.21 (3H, m), 3.18-3.22 (1H, m), 3.40-3.47 (1H, m), 3.56-3.60 (1H, m), 3.71 (1H, d), 3.91-3.94 (1H, m), 3.98 (1H, d), 4.35 (3H, d), 5.51 (1H, t), 6.74 (1H, s).

Mass Spectrum; M+H$^+$ 244.

[2-Chloro-6-[(3S)-3-methylmorpholin-4-yl]pyrimidin-4-yl]methanol can also be prepared by the dropwise addition of lithium borohydride (2M in THF) (454 mL, 908.17 mmol) over a period of 15 minutes to a solution of methyl 2-chloro-6-[(3S)-3-methylmorpholin-4-yl]pyrimidine-4-carboxylate (235 g, 864.92 mmol) in the THF (4701 mL) at 0° C. The mixture was stirred at RT for 2 hours then water (1500 mL) was added slowly. A white solid formed which was decanted off and the THF was removed under vacuum. To the residue was added more water (500 mL), and extracted with ethyl acetate (3×700 mL). The combined organics were washed with brine, dried over MgSO$_4$, filtered, and concentrated to a white solid which was identical to previous samples.

Methyl 2-chloro-6-[(3S)-3-methylmorpholin-4-yl]pyrimidine-4-carboxylate

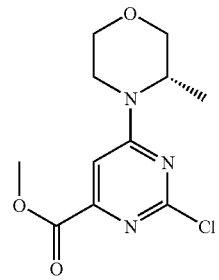

Methyl 2,6-dichloropyrimidine-4-carboxylate (5 g) was dissolved in DCM (120 mL). (3S)-3-Methylmorpholine (2.49 g) dissolved in triethylamine (3.70 mL) and DCM (10 mL) was added dropwise to the solution over 10 minute. The reaction was left to stir at room temperature for 1 hour. The reaction was then evaporated to dryness and dissolved in DCM (300 mL). The organics were washed once with water (150 mL) and dried (MgSO$_4$), filtered and evaporated. The crude material was chromatographed on silica, eluting with 2.5% methanol in DCM, to give the desired material as a white solid (3.15 g).

NMR Spectrum: $^1$H NMR (400.132 MHz, DMSO) δ 1.22-1.24 (3H, m), 3.25 (1H, d), 3.41-3.48 (1H, m), 3.57-3.61 (1H, m), 3.71 (1H, d), 3.87 (3H, s), 3.91-3.95 (1H, m), 4.25 (1H, s), 4.45 (1H, s), 7.29 (1H, s).

Mass Spectrum; M+H$^+$ 272.

Methyl 2-chloro-6-[(3S)-3-methylmorpholin-4-yl]pyrimidine-4-carboxylate can also be prepared by the addition of methyl 2,6-dichloropyrimidine-4-carboxylate (250 g, 1207.65 mmol) to the DCM (2500 mL). Triethylamine (185 mL, 1328.41 mmol) was added and the reaction cooled to 0° C. (3S)-3-Methylmorpholine (128 g, 1268.03 mmol) dissolved in DCM (300 mL), was added dropwise over 30 minutes and the mixture stirred at 5° overnight. Water (800 mL) was added, the phases separated and the aqueous layer extracted with DCM (300 mL). The combined organics were washed with brine (300 mL), dried over MgSO$_4$, filtered and concentrated to a cream solid. The crude solid was dissolved in hot ethyl acetate (3 volumes) then isohexane (5 volumes) added the mixture left to cool with stirring over the weekend to give the desired material as a solid which was identical to previous samples.

EXAMPLE 2

3-Cyclopropyl-1-[4-[4-[(3S)-3-methylmorpholin-4-yl]-6-(2-methylsulfonylpropan-2-yl)pyrimidin-2-yl]phenyl]thiourea

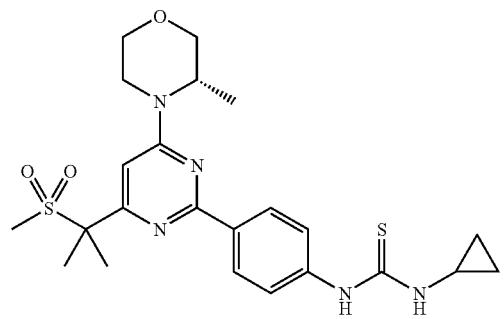

To a solution of 4-[4-[(3S)-3-methylmorpholin-4-yl]-6-(2-methylsulfonylpropan-2-yl)pyrimidin-2-yl]aniline (100 mg, 0.26 mmol) in DCM (2 mL) was added a solution of di(imidazol-1-yl)methanethione (50.2 mg, 0.28 mmol) in DCM (1 mL) and the solution stirred at RT for 2 hours. Cyclopropylamine (0.089 mL, 1.28 mmol) was added followed by triethylamine (0.036 mL, 0.26 mmol) and the solution stirred overnight at RT. The crude product was purified by preparative HPLC, using decreasingly polar mixtures of water (containing 1% NH3) and MeCN as eluents, to give the desired material as a white solid (64.0 mg, 51.0%).

NMR Spectrum: $^1$H NMR (400.13 MHz, DMSO-d$_6$) δ 0.59-0.62 (2H, m), 0.74-0.79 (2H, m), 1.24 (3H, d), 1.78 (6H, s), 2.90-2.95 (1H, m), 3.04 (3H, s), 3.19-3.25 (1H, m), 3.47-3.54 (1H, m), 3.64-3.67 (1H, m), 3.78 (1H, d), 3.96-4.00 (1H, m), 4.22-4.26 (1H, m), 4.59-4.66 (1H, m), 6.78 (1H, s), 7.62 (2H, d), 8.14 (1H, s), 8.29 (2H, d), 9.51 (1H, s)

LCMS Spectrum: m/z (ESI+)(M+H)+=490; HPLC tR=2.08 min.

The compounds below were prepared in an analogous fashion from 4-[4-[(3S)-3-methylmorpholin-4-yl]-6-(2-methylsulfonylpropan-2-yl)pyrimidin-2-yl]aniline using the appropriate amine.

| Example | Structure | NAME | LCMS MH+ | Retention time (min) |
|---|---|---|---|---|
| 2a | 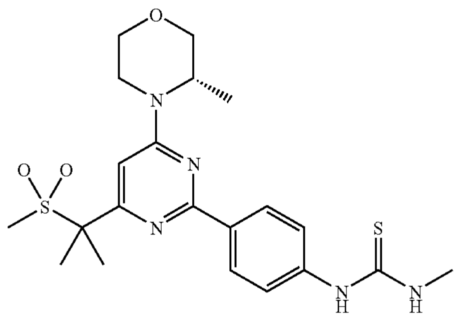 | 3-methyl-1-[4-[4-[(3S)-3-methylmorpholin-4-yl]-6-(2-methylsulfonylpropan-2-yl)pyrimidin-2-yl]phenyl]thiourea | 464 | 1.96 |
| 2b | 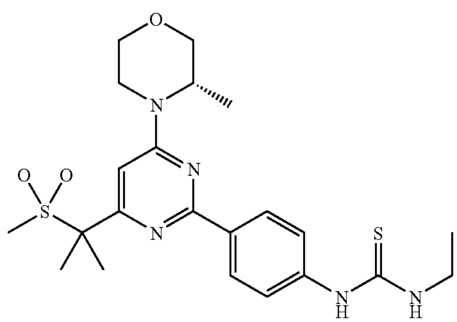 | 3-ethyl-1-[4-[4-[(3S)-3-methylmorpholin-4-yl]-6-(2-methylsulfonylpropan-2-yl)pyrimidin-2-yl]phenyl]thiourea | 478 | 2.14 |
| 2c | 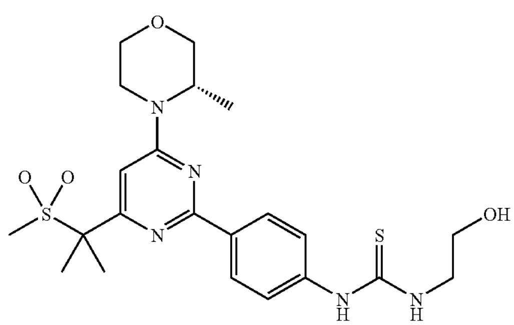 | 3-(2-hydroxyethyl)-1-[4-[4-[(3S)-3-methylmorpholin-4-yl]-6-(2-methylsulfonylpropan-2-yl)pyrimidin-2-yl]phenyl]thiourea | 494 | 1.78 |
| 2d | 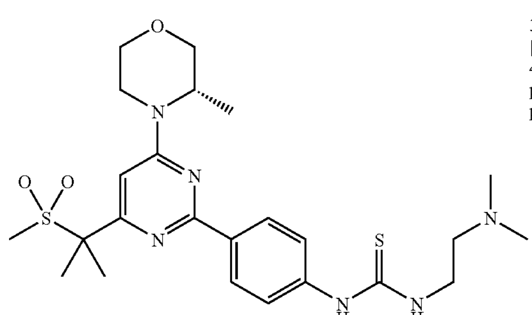 | 3-(2-dimethylaminoethyl)-1-[4-[4-[(3S)-3-methylmorpholin-4-yl]-6-(2-methylsulfonyl-propan-2-yl)pyrimidin-2-yl]phenyl]thiourea | 521 | 2.08 |

EXAMPLE 2a $^1$H NMR (400.13 MHz, DMSO-$d_6$) δ 1.24 (3H, d), 1.78 (6H, s), 2.95 (3H, d), 3.04 (3H, s), 3.17-3.25 (1H, m), 3.48-3.53 (1H, m), 3.63-3.67 (1H, m), 3.77 (1H, d), 3.96-3.99 (1H, m), 4.24 (1H, d), 4.60-4.65 (1H, m), 6.78 (1H, s), 7.55 (2H, d), 7.85 (1H, s), 8.30 (2H, d), 9.73 (1H, s)

EXAMPLE 2b $^1$H NMR (400.13 MHz, DMSO-$d_6$) δ 1.14 (3H, t), 1.24 (3H, d), 1.77 (3H, s), 1.78 (3H, s), 3.03 (3H, s), 3.18-3.25 (1H, m), 3.47-3.52 (3H, m), 3.63-3.67 (1H, m), 3.77 (1H, d), 3.96-4.00 (1H, m), 4.22-4.25 (1H, m), 4.59-4.65 (1H, m), 6.77 (1H, s), 7.56 (2H, d), 7.88 (1H, s), 8.30 (2H, d), 9.63 (1H, s)

EXAMPLE 2c

¹H NMR (400.13 MHz, DMSO-d₆) δ 1.24 (3H, d), 1.78 (6H, s), 3.04 (3H, s), 3.17-3.25 (1H, m), 3.47-3.53 (1H, m), 3.57 (4H, s), 3.63-3.66 (1H, m), 3.77 (1H, d), 3.96-4.00 (1H, m), 4.24 (1H, d), 4.59-4.65 (1H, m), 4.81 (1H, s), 6.78 (1H, s), 7.63 (2H, d), 7.87 (1H, s), 8.30 (2H, d), 9.81 (1H, s)

EXAMPLE 2d

¹H NMR (400.13 MHz, DMSO-d₆) δ 1.24 (3H, d), 1.78 (6H, s), 2.21 (6H, s), 2.45 (2H, t), 3.04 (3H, s), 3.18-3.25 (1H, m), 3.47-3.57 (3H, m), 3.63-3.67 (1H, m), 3.77 (1H, d), 3.96-4.00 (1H, m), 4.22-4.25 (1H, m), 4.59-4.65 (1H, m), 6.78 (1H, s), 7.65 (2H, d), 7.77 (1H, s), 8.30 (2H, d), 9.90 (1H, s)

The preparation of 4-[4-[(3S)-3-methylmorpholin-4-yl]-6-(2-methylsulfonylpropan-2-yl)pyrimidin-2-yl]aniline is described below:

4-[4-[(3S)-3-Methylmorpholin-4-yl]-6-(2-methylsulfonylpropan-2-yl)pyrimidin-2-yl]aniline

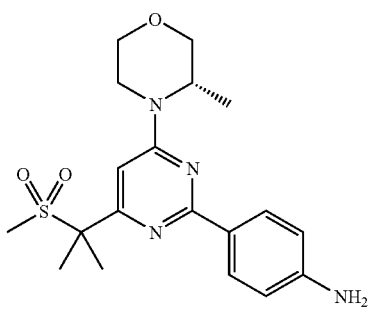

Dichlorobis(triphenylphosphine)palladium(II) (0.287 g, 0.41 mmol) was added to 2-chloro-4-[(3S)-3-methylmorpholin-4-yl]-6-(2-methylsulfonylpropan-2-yl)pyrimidine (2.73 g, 8.18 mmol), 4-(4,4,5,5-tetramethyl-1,3,2-dioxaborolan-2-yl)aniline (2.329 g, 10.63 mmol) and 2M aqueous sodium carbonate (15 mL, 29.44 mmol) in DMF (15 mL), DME (15 mL), ethanol (15 mL) and water (37.5 mL) at RT under nitrogen. The reaction was purged with nitrogen for 15 minutes and the resulting mixture was stirred at 80° C. for 3 hours. The reaction mixture was diluted with ethyl acetate (300 mL) and washed sequentially twice with water (150 mL) and saturated brine (150 mL). The organic layer was dried (MgSO₄), filtered and evaporated to afford crude product as a dark brown gum. The crude product was purified by flash silica chromatography, eluting with 0 to 20% ethyl acetate in DCM, to give the desired material as a white solid (2.16 g).

NMR Spectrum: ¹H NMR (400.13 MHz, DMSO-d₆) δ 1.33 (3H, d), 1.87 (6H, s), 2.93 (3H, s), 3.28-3.35 (1H, m), 3.56-3.63 (1H, m), 3.72-3.76 (1H, m), 3.82 (1H, d), 3.90 (2H, s), 4.01-4.05 (1H, m), 4.11-4.15 (1H, m), 4.46-4.53 (1H, m), 6.55 (1H, s), 6.71 (2H, d), 8.21 (2H, d)

LCMS Spectrum: m/z (ESI+) (M+H)+=391; HPLC tR=2.05 min.

2-Chloro-4-[(3S)-3-methylmorpholin-4-yl]-6-(2-methylsulfonylpropan-2-yl)pyrimidine

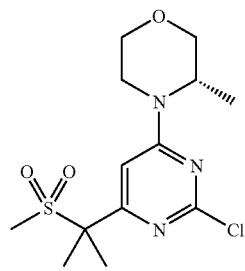

Sodium tert-butoxide (278 mg, 2.89 mmol) was added to 2-chloro-4-[(3S)-3-methylmorpholin-4-yl]-6-(methylsulfonylmethyl)pyrimidine (883 mg, 2.89 mmol) in DMF (25 mL) at 0° C. under nitrogen. Iodomethane (0.180 mL, 2.89 mmol) was added and the resulting solution was stirred at 0° C. for 15 minutes. Further sodium tert-butoxide (278 mg, 2.89 mmol) was added followed by iodomethane (0.180 mL, 2.89 mmol) and the resulting solution was stirred at 0° C. for 1 hour. The reaction was diluted with DCM (100 mL) and washed with water (100 mL) and brine (100 mL). The organic layer was dried (MgSO₄), filtered and the solvent evaporated to a gum which slowly crystallised. The crude product was purified by flash silica chromatography, eluting with 0 to 5% methanol in DCM, to give the desired material as a white solid (691 mg).

NMR Spectrum: ¹H NMR (400.13 MHz, DMSO-d₆) δ 1.26 (3H, d), 1.72 (6H, s), 2.87 (3H, s), 3.19-3.27 (1H, m), 3.44-3.51 (1H, m), 3.60-3.63 (1H, m), 3.72 (1H, d), 3.92-3.96 (2H, m), 4.23-4.32 (1H, m), 6.53 (1H, s)

LCMS Spectrum: m/z (ESI+) (M+H)+=334; HPLC tR=1.95 min.

The preparation of 2-chloro-4-[(3S)-3-methylmorpholin-4-yl]-6-(methylsulfonylmethyl)pyrimidine was described earlier.

EXAMPLE 3

1-[4-[4-[2-(Benzenesulfonyl)propan-2-yl]-6-[(3S)-3-methylmorpholin-4-yl]pyrimidin-2-yl]phenyl]-3-methylthiourea

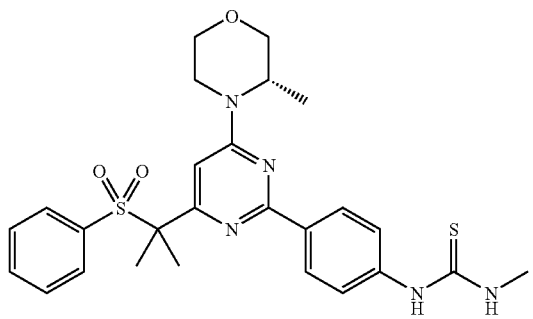

A solution of 4-[4-[2-(benzenesulfonyl)propan-2-yl]-6-[(3S)-3-methylmorpholin-4-yl]pyrimidin-2-yl]aniline (0.091 g, 0.2 mmol) in THF (1.0 mL) was added to a solution of di(imidazol-1-yl)methanethione (0.050 g, 0.28 mmol) in DCM (1.0 mL) and the resulting solution was stirred at 40° C. for 30 minutes. A solution of methylamine (2.0M in THF, 0.5 mL, 1.0 mmol) was added and the reaction was stirred at 40° C. for 30 minutes and the solvent was evaporated. The crude material was purified by preparative HPLC to give the desired material as a solid (63 mg).

NMR Spectrum: $^1$H NMR (300.13 MHz, DMSO-$d_6$) δ 1.20 (3H, d), 1.77 (3H, s), 1.78 (3H, s), 2.93 (3H, d), 3.11-3.20 (1H, m), 3.45-3.52 (1H, m), 3.61-3.66 (1H, m), 3.76 (1H, d), 3.94-3.98 (1H, m), 4.14 (1H, d), 4.50-4.59 (1H, m), 6.69 (1H, s), 7.40 (2H, d), 7.46-7.53 (4H, m), 7.61-7.68 (1H, m), 7.78-7.88 (3H, m), 9.73 (1H, s)

LCMS Spectrum: m/z (ESI+)(M+H)+526, HPLC tR=2.41 min

The compounds below were prepared in an analogous fashion using the appropriate amine.

EXAMPLE 3a $^1$H NMR (300.13 MHz, DMSO-$d_6$) δ 0.56-0.62 (2H, m), 0.72-0.78 (2H, m), 1.21 (3H, d), 1.77 (3H, s), 1.78 (3H, s), 2.81-2.99 (1H, m), 3.11-3.22 (1H, m), 3.45-3.52 (1H, m), 3.61-3.66 (1H, m), 3.76 (1H, d), 3.94-3.99 (1H, m), 4.13-4.17 (1H, m), 4.51 4.59 (1H, m), 6.70 (1H, s), 7.40-7.53 (6H, m), 7.62-7.68 (1H, m), 7.84 (2H, d), 8.14 (1H , s), 9.48 (1H, s)

EXAMPLE 3b $^1$H NMR (300.13 MHz, DMSO-$d_6$) δ 1.13 (3H, t), 1.20 (3H, d), 1.77 (3H, s), 1.78 (3H, s), 3.11, 3.22 (1H, m), 3.43-3.51 (3H, m), 3.61-3.66 (1H, m), 3.76 (1H, d), 3.94-3.99 (1H, m), 4.11-4.16 (1H, m), 4.51 4.58 (1H, m), 6.69 (1H, s), 7.41 (2H, d), 7.46-7.53 (4H, m), 7.62-7.68 (1H, m), 7.85 (3H, d), 9.62 (1H, s)

| Example | Structure | NAME | LCMS MH+ | Retention time (min) |
|---|---|---|---|---|
| 3a | 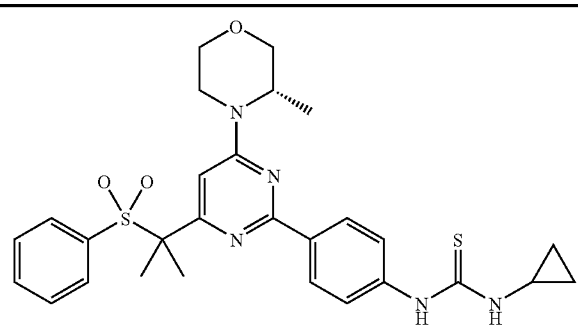 | 1-[4-[4-[2-(benzenesulfonyl)propan-2-yl]-6-[(3S)-3-methylmorpholin-4-yl]pyrimidin-2-yl]phenyl]-3-cyclopropylthiourea | 526 | 2.55 |
| 3b | 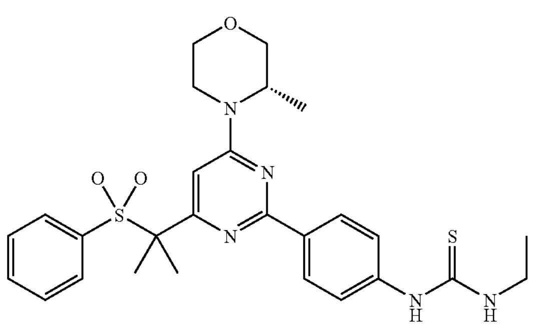 | 1-[4-[4-[2-(benzenesulfonyl)propan-2-yl]-6-[(3S)-3-methylmorpholin-4-yl]pyrimidin-2-yl]phenyl]-3-ethylthiourea | 540 | 2.57 |
| 3c | 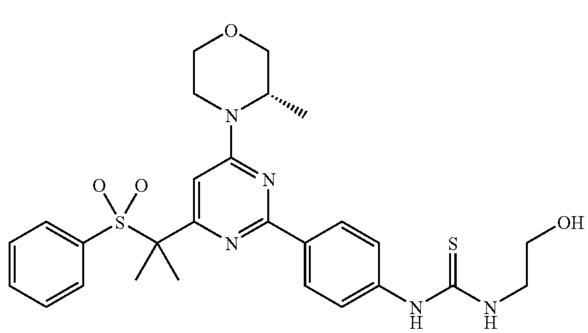 | 1-[4-[4-[2-(benzenesulfonyl)propan-2-yl]-6-[(3S)-3-methylmorpholin-4-yl]pyrimidin-2-yl]phenyl]-3-(2-hydroxyethyl)thiourea | 556 | 2.16 |

EXAMPLE 3c

¹H NMR (300.13 MHz, DMSO-d₆) δ 1.20 (3H, d), 1.77 (3H, s), 1.78 (3H, s), 3.11-3.21 (1H, m), 3.44-3.50 (1H, m), 3.52-3.58 (4H, m), 3.60-3.67 (1H, m), 3.76 (1H, d), 3.94-3.98 (1H, m), 4.08-4.16 (1H, m), 4.50-4.59 (1H, m), 4.84 (1H, s), 6.69 (1H, s), 7.46-7.52 (6H, m), 7.62-7.68 (1H, m), 7.83-7.87 (3H, m), 9.79 (1H, s)

The preparation of 4-[4-[2-(benzenesulfonyl)propan-2-yl]-6-[(3S)-3-methylmorpholin-4-yl]pyrimidin-2-yl]aniline is described below:

4-[4-[2-(benzenesulfonyl)propan-2-yl]-6-[(3S)-3-methylmorpholin-4-yl]pyrimidin-2-yl]aniline

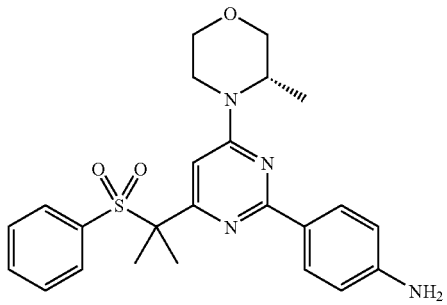

Sodium carbonate (2M aqueous solution) (3.21 mL, 6.43 mmol) was added to 4-(4,4,5,5-tetramethyl-1,3,2-dioxaborolan-2-yl)aniline (391 mg, 1.79 mmol) and 4-[2-(benzenesulfonyl)propan-2-yl]-2-chloro-6-[(3S)-3-methylmorpholin-4-yl]pyrimidine (707 mg, 1.79 mmol) in a mixture of DME (8.0 mL), ethanol (4.0 mL), DMF (4.0 mL) and water (4.0 mL) under nitrogen. The mixture was degassed and purged with nitrogen three times. Bis(triphenylphosphine)palladium(II) chloride (63 mg, 0.09 mmol) was added and the mixture was degassed and purged with nitrogen a further three times. The resulting suspension was stirred at 80° C. for 30 minutes. The reaction mixture was concentrated and diluted with ethyl acetate (50 mL), and washed sequentially with water (2×25 mL) and saturated brine (25 mL). The organic layer was dried over MgSO₄, filtered and evaporated to afford crude product. The crude product was purified by flash silica chromatography, elution gradient 0 to 2% methanol in DCM, to give the desired material as a beige solid (578 mg).

NMR Spectrum: ¹H NMR (300.13 MHz, CDCl₃) δ 1.33 (3H, d), 1.85 (3H, s), 1.85 (3H, s), 3.25-3.35 (1H, m), 3.58-3.67 (1H, m), 3.74-3.85 (4H, m), 4.02-4.07 (1H, m), 4.10-4.15 (1H, m), 4.47-4.50 (1H, m), 6.55-6.59 (2H, m), 6.63 (1H, s), 7.30-7.36 (2H, m), 7.45-7.51 (1H, m), 7.53-7.57 (2H, m), 7.74-7.78 (2H, m)

LCMS Spectrum: m/z (ESI+) (M+H)+=453; HPLC tR=2.22 min

4-[2-(benzenesulfonyl)propan-2-yl]-2-chloro-6-[(3S)-3-methylmorpholin-4-yl]pyrimidine

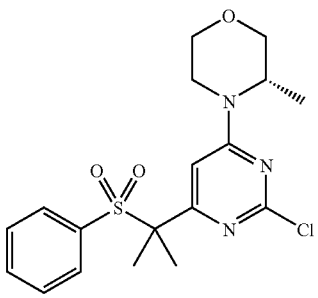

Iodomethane (0.156 mL, 2.50 mmol) was added to 4-(benzenesulfonylmethyl)-2-chloro-6-[(3S)-3-methylmorpholin-4-yl]pyrimidine (0.920 g, 2.5 mmol) and sodium tert-butoxide (0.240 g, 2.50 mmol) in DMF (14 mL) cooled to 0° C. The reaction mixture was stirred for 10 minutes then a second equivalent of sodium tert-butoxide (0.240 g, 2.50 mmol) and iodomethane (0.156 mL, 2.50 mmol) were added. The reaction was allowed to warm to RT and then stirred for 1 hour. The mixture was diluted with water (50 mL) and DCM (50 mL). The organic layer was separated and washed sequentially with water (2×50 mL) and brine (2×50 mL). The organic layer was then dried (MgSO₄), filtered and evaporated to give crude product. The crude product was purified by flash silica chromatography, elution gradient 0 to 2% methanol in DCM, to give the desired material as a white solid (0.742 g).

NMR Spectrum: 1H NMR (300.13 MHz, CDCl3) δ 1.34 (3H, d), 1.75 (3H, s), 1.75 (3H, s), 3.26-3.35 (1H, m), 3.53-3.62 (1H, m), 3.69-3.74 (1H, m), 3.79-3.83 (1H, m), 4.00-4.05 (2H, m), 4.34 (1H, d), 6.76 (1H, s), 7.45-7.50 (2H, m), 7.56-7.65 (3H, m)

LCMS Spectrum: m/z (ESI+) (M+H)+=396; HPLC tR=2.46 min

4-(Benzenesulfonylmethyl)-2-chloro-6-[(3S)-3-methylmorpholin-4-yl]pyrimidine

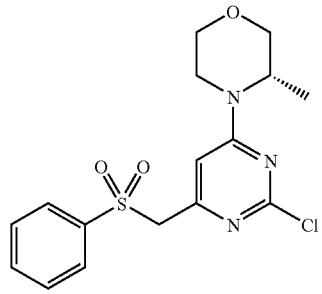

Benzenesulfinic acid, sodium salt (4.22 g, 25.74 mmol) was added to 2-chloro-4-(iodomethyl)-6-[(3S)-3-methylmorpholin-4-yl]pyrimidine (7.0 g, 19.80 mmol) in acetonitrile (200 mL) and the resulting mixture stirred under a nitrogen atmosphere at 80° C. for 20 hours. The reaction was cooled and the solvent was removed. DCM was added and the solution was washed with water. The DCM was dried (MgSO₄), filtered and the solvent was removed. The crude product was purified by flash silica chromatography, elution gradient 0 to 30% ethyl acetate in DCM, to give the desired material as a cream solid (6.21 g).

NMR Spectrum: ¹H NMR (400.132 MHz, DMSO-d₆) δ 1.15-1.16 (3H, d), 3.11-3.18 (1H, td), 3.38-3.45 (1H, td), 3.55-3.58 (1H, dd), 3.70-3.73 (1H, d), 3.85-3.94 (2H, m), 4.15 (1H, bs), 4.64 (2H, s), 6.67 (1H, s), 7.63-7.66 (2H, m), 7.74-7.80 (3H, m).

LCMS Spectrum: m/z (ES+) (M+H)+=368; HPLC tR=2.05 min.

The preparation of 2-chloro-4-(iodomethyl)-6-[(3S)-3-methylmorpholin-4-yl]pyrimidine was described earlier.

EXAMPLE 4

3-Cyclopropyl-1-[4-[4-[2-(3-hydroxypropylsulfonyl)propan-2-yl]-6-[(3S)-3-methylmorpholin-4-yl]pyrimidin-2-yl]phenyl]thiourea

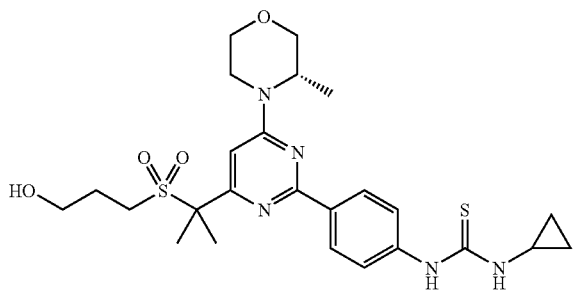

Di(imidazol-1-yl)methanethione (46 mg, 0.20 mmol) was added to 3-[2-[2-(4-aminophenyl)-6-[(3S)-3-methylmorpholin-4-yl]pyrimidin-4-yl]propan-2-ylsulfonyl]propan-1-ol (100 mg, 0.17 mmol) in DCM (2 mL) and THF (1 mL) and the reaction stirred at RT for 3 hours. Cyclopropylamine (1.20 mmol) was added followed by triethylamine (0.043 mL, 0.17 mmol) and the reaction stirred at 50° C. for 2 hours. The mixture was allowed to cool and purified by preparative HPLC to give the desired material as a solid (97 mg).

NMR Spectrum: $^1$H NMR (400.132 MHz, DMSO-$d_6$) δ 0.57-0.65 (2H, m), 0.72-0.82 (2H, m), 1.24 (3H, d), 1.72-1.85 (8H, m), 3.21-3.35 (4H, m), 3.41-3.54 (3H, m), 3.65 (1H, d), 3.77 (1H, d), 3.98 (1H, d), 4.24 (1H, d), 4.56-4.66 (2H, m), 6.79 (1H, s), 7.62 (2H, d), 8.16 (1H, s), 8.29 (2H, d), 9.51 (1H, s).

LCMS Spectrum: m/z (ES+) (M+H)+=534; HPLC tR=1.94 min.

The following compounds were prepared in an analogous fashion from 3-[2-[2-(4-aminophenyl)-6-[(3S)-3-methylmorpholin-4-yl]pyrimidin-4-yl]propan-2-ylsulfonyl]propan-1-ol and the appropriate amine.

| Example | Structure | NAME | LCMS MH+ | Retention time (min) |
|---|---|---|---|---|
| 4a | 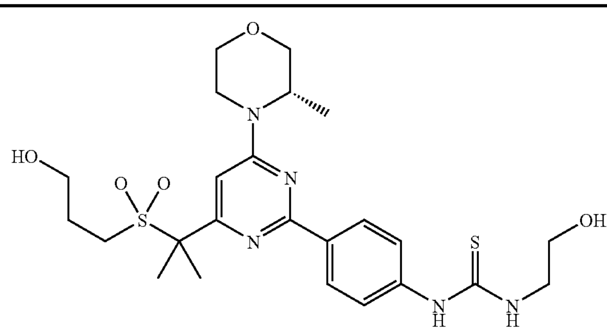 | 3-(2-hydroxyethyl)-1-[4-[4-[2-(3-hydroxypropylsulfonyl)propan-2-y1]-6-[(3S)-3-methylmorpholin-4-yl]pyrimidin-2-yl]phenyl]thiourea | 538 | 1.68 |
| 4b | 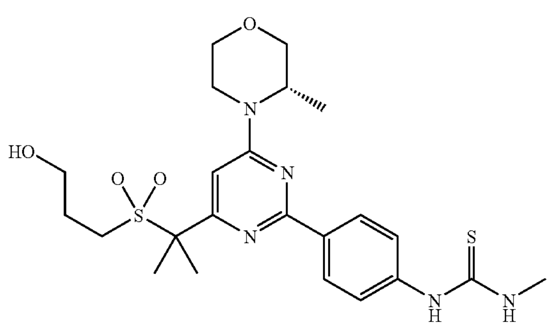 | 1-[4-[4-[2-(3-hydroxypropylsulfonyl)propan-2-y1]-6-[(3S)-3-methylmorpholin-4-yl]pyrimidin-2-yl]phenyl]-3-methylthiourea | 508 | 1.82 |
| 4c | 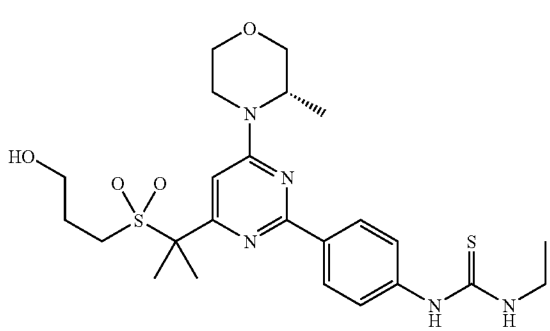 | 3-ethyl-1-[4-[4-[2-(3-hydroxypropylsulfonyl)propan-2-y1]-6-[(3S)-3-methylmorpholin-4-yl]pyrimidin-2-yl]phenyl]thiourea | 522 | 1.97 |

EXAMPLE 4a

¹H NMR (400.132 MHz, DMSO-d₆) δ 1.24 (3H, d), 1.70-1.81 (8H, m), 3.17-3.34 (6H, m), 3.41-3.46 (2H, m), 3.47-3.55 (1H, m), 3.65 (1H, d), 3.77 (1H, d), 3.98 (1H, d), 4.24 (1H, d), 4.56-4.63 (2H, m), 4.81 (1H, s), 6.79 (1H, s), 7.63 (2H, d), 7.87 (1H, s), 8.30 (2H, d), 9.81 (1H, s)

EXAMPLE 4b

¹H NMR (400.132 MHz, DMSO-d₆) δ 1.24 (3H, d), 1.71-1.82 (8H, m), 2.96 (3H, s), 3.16-3.34 (3H, m), 3.42-3.55 (3H, m), 3.65 (1H, d), 3.77 (1H, d), 3.98 (1H, d), 4.23 (1H, d), 4.56-4.64 (2H, m), 6.79 (1H, s), 7.55 (2H, d), 7.85 (1H, s), 8.30 (2H, d), 9.73 (1H, s)

EXAMPLE 4c

¹H NMR (400.132 MHz, DMSO-d₆) δ 1.14 (3H, t), 1.24 (3H, d), 1.74-1.82 (8H, m), 3.19-3.34 (5H, m), 3.39-3.57 (3H, m), 3.65 (1H, d), 3.77 (1H, d), 3.98 (1H, d), 4.22 (1H, d), 4.57-4.64 (2H, m), 6.79 (1H, s), 7.57 (2H, d), 7.89 (1H, s), 8.30 (2H, d)

The preparation of 3-[2-[2-(4-aminophenyl)-6-[(3S)-3-methylmorpholin-4-yl]pyrimidin-4-yl]propan-2-ylsulfonyl]propan-1-ol is described below.

3-[2-[2-(4-Aminophenyl)-6-[(3S)-3-methylmorpholin-4-yl]pyrimidin-4-yl]propan-2-ylsulfonyl]propan-1-ol

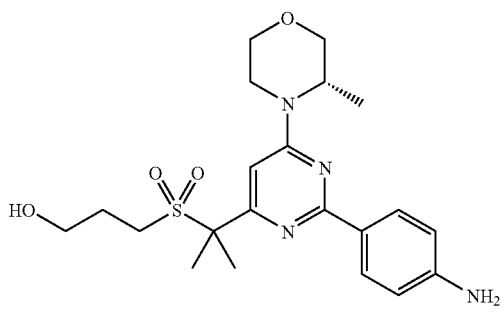

Bis(triphenylphosphine)palladium(II) chloride (0.176 g, 0.25 mmol) was added to 3-[2-[2-chloro-6-[(3S)-3-methylmorpholin-4-yl]pyrimidin-4-yl]propan-2-ylsulfonyl]propoxy-tri(propan-2-yl)silane (2 g, 3.74 mmol), 4-(4,4,5,5-tetramethyl-1,3,2-dioxaborolan-2-yl)aniline (1.107 g, 5.05 mmol) and 2M sodium carbonate solution (3 mL, 6.00 mmol) in a solvent mixture of DMF (5 mL), DME (8 mL), water (2 mL) and ethanol (1.5 mL) and the resulting mixture stirred at 90° C. for 5 hours, under an inert atmosphere. The reaction mixture was diluted with ethyl acetate (200 mL), and washed with water (2×100 mL). The organic layer was dried over Na₂SO₄, filtered and evaporated to afford a residue which was dissolved in DCM (100 mL), and tetrabutylammonium fluoride (18.72 mL, 18.72 mmol) added. The mixture was stirred at RT for 2 hours. The reaction mixture was diluted with DCM (100 mL), and washed sequentially with a saturated aqueous solution of ammonium chloride (50 mL) and water (2×100 mL). The organic layer was dried over Na₂SO₄, filtered and evaporated to afford crude product. The crude product was purified by flash silica chromatography, elution gradient 20 to 100% ethyl acetate in isohexane then 4% methanol in ethyl acetate, to give a material which was further purified by ion exchange chromatography using an SCX column, eluting with 7N ammonia in methanol, to give the desired material as a beige solid (1.0 g).

NMR Spectrum: ¹H NMR (400.132 MHz, DMSO-d₆) δ 1.21 (3H, d), 1.72-1.81 (8H, m), 3.14-3.22 (1H, m), 3.26-3.35 (3H, m), 3.41-3.52 (3H, m), 3.64 (1H, d), 3.76 (1H, d), 3.97 (1H, d), 4.19 (1H, d), 4.50-4.60 (2H, m), 5.54 (2H, d), 6.58-6.69 (3H, m), 8.06 (2H, d)

LCMS Spectrum: none.

3-[2-[2-Chloro-6-[(3S)-3-methylmorpholin-4-yl]pyrimidin-4-yl]propan-2-ylsulfonyl]propoxy-tri(propan-2-yl)silane

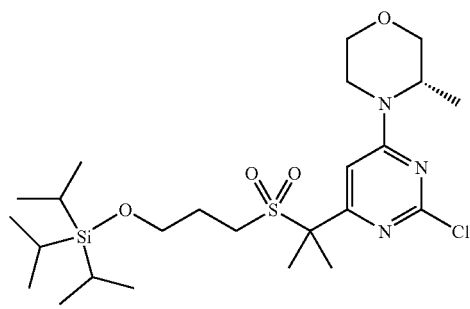

Sodium tert-butoxide (5.93 mmol) was added to a solution of 3-[[2-chloro-6-[(3S)-3-methylmorpholin-4-yl]pyrimidin-4-yl]methylsulfonyl]propoxy-tri(propan-2-yl)silane (3 g, 5.93 mmol) in DMF (10 mL) at −5° C., followed by the dropwise addition of iodomethane (0.33 mL) at −5° C. The addition of sodium tert-butoxide and iodomethane was repeated and the reaction stirred at −5° C. for 1 hour then RT for 16 hours. The reaction mixture was diluted with ethyl acetate (250 mL), and washed with water (2×150 mL). The organic layer was dried over MgSO₄, filtered and evaporated to afford crude product which was triturated with a mixture of diethyl ether and isohexane to give the desired material as a cream solid (2.0 g).

NMR Spectrum: ¹H NMR (400.132 MHz, DMSO-d₆) δ 0.96-1.04 (21H, m), 1.20 (3H, d), 1.79-1.89 (2H, m), 3.12-3.22 (3H, m), 3.39-3.48 (1H, m), 3.58 (1H, d), 3.69-3.78 (3H, m), 3.94 (1H, d), 4.08 (1H, s), 6.88 (1H, s)

LCMS Spectrum: m/z (ES+) (M+H)+=534; HPLC tR=3.98 min.

3-[[2-Chloro-6-[(3S)-3-methylmorpholin-4-yl]pyrimidin-4-yl]methylsulfonyl]propoxy-tri(propan-2-yl)silane

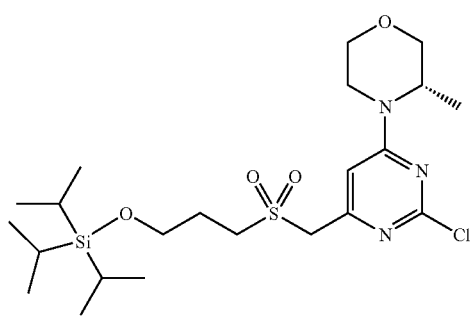

3-[[2-Chloro-6-[(3S)-3-methylmorpholin-4-yl]pyrimidin-4-yl]methylsulfonyl]propan-1-ol (5.04 g, 14.41 mmol) in DMF (25 mL) was added to chlorotrisopropylsilane (3.70 mL, 17.29 mmol) and imidazole (2.354 g, 34.58 mmol) in DMF (25 mL) at RT over a period of 5 minutes under a nitrogen atmosphere. The resulting solution was stirred at RT for 18 hours. The reaction mixture was evaporated to dryness and redissolved in DCM (200 mL) then washed sequentially with water (100 mL) and saturated brine (100 mL). The organic layer was dried (MgSO$_4$), filtered and evaporated to give the desired material as an oil (7.29 g).

NMR Spectrum: $^1$H NMR (400.132 MHz, CDCl$_3$) δ 0.99-1.07 (21H, m), 1.33 (3H, d), 2.06-2.13 (2H, m), 3.20-3.24 (2H, m), 3.26-3.34 (1H, m), 3.50-3.57 (1H, m), 3.66-3.70 (1H, m), 3.77-3.83 (3H, m), 3.99-4.03 (2H, m), 4.16 (2H, s), 4.25-4.37 (1H, m), 6.54 (1H, s)

LCMS Spectrum: m/z (ESI+)(M+H)+=506; HPLC tR=3.42 min.

3-[[2-Chloro-6-[(3S)-3-methylmorpholin-4-yl]pyrimidin-4-yl]methylsulfonyl]propan-1-ol

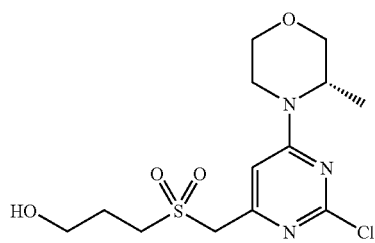

3-Chlorobenzoperoxoic acid (4.00 g, 23.16 mmol) was added to 3-[[2-chloro-6-[(3S)-3-methylmorpholin-4-yl]pyrimidin-4-yl]methylsulfanyl]propan-1-ol (3.68 g, 11.58 mmol) in DCM (100 mL) at RT over a period of 5 minutes. The resulting solution was stirred at RT for 3 hours. A further portion of 3-chlorobenzoperoxoic acid (2.00 g, 11.58 mmol) was added and the resulting solution was stirred at RT for an additional 1 hour. The reaction mixture was washed sequentially with 10% aqueous sodium metabisulphite solution (2×100 mL), a saturated aqueous solution of sodium hydrogen carbonate (100 mL), and saturated brine (100 mL). The organic layer was dried (MgSO$_4$), filtered and evaporated to give the desired material as a gum (4.05 g).

NMR Spectrum: $^1$H NMR (400.132 MHz, CDCl$_3$) δ 1.34 (3H, d), 2.12-2.18 (2H, m), 3.27 (2H, t), 3.31-3.35 (1H, m), 3.51-3.57 (1H, m), 3.67-3.70 (1H, m), 3.77-3.82 (3H, m), 3.99-4.03 (1H, m), 4.18 (2H, s), 4.26-4.37 (1H, m), 6.51 (1H, s)

LCMS Spectrum: m/z (ESI+)(M+H)+=350; HPLC tR=1.30 min.

3-[[2-Chloro-6-[(3S)-3-methylmorpholin-4-yl]pyrimidin-4-yl]methylsulfanyl]propan-1-ol

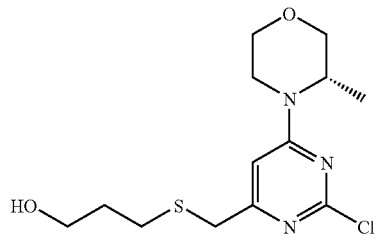

A solution of 2-chloro-4-(iodomethyl)-6-[(3S)-3-methylmorpholin-4-yl]pyrimidine (12.4 g, 35.07 mmol) in DCM (50 mL) was added to a stirred solution of 3-mercapto-1-propanol (3.64 mL, 42.08 mmol) and DIPEA (9.77 mL, 56.11 mmol) in DCM (100 mL) at RT, over a period of 40 minutes under a nitrogen atmosphere. The resulting solution was stirred at RT for 18 hours. The reaction mixture was washed sequentially with a saturated aqueous solution of sodium hydrogen carbonate (2×50 mL) and saturated brine (50 mL). The organic layer was dried (MgSO$_4$), filtered and evaporated to afford crude product as a dark brown oil. The crude product was purified by flash silica chromatography, eluting with 0 to 75% ethyl acetate in DCM, to give the desired material as a yellow gum (5.86 g).

NMR Spectrum: $^1$H NMR (400.132 MHz, CDCl$_3$) δ 1.32 (3H, d), 1.84-1.90 (2H, m), 1.94 (1H, s), 2.69 (2H, t), 3.24-3.32 (1H, m), 3.51-3.58 (1H, m), 3.61 (2H, s), 3.67-3.71 (1H, m), 3.73-3.80 (3H, m), 3.98-4.04 (2H, m), 4.28-4.34 (1H, m), 6.45 (1H, s)

LCMS Spectrum: m/z (ESI+)(M+H)+=318; HPLC tR=1.55 min.

The preparation of 2-chloro-4-(iodomethyl)-6-[(3S)-3-methylmorpholin-4-yl]pyrimidine was described earlier.

EXAMPLE 5

3-(2-Hydroxyethyl)-1-[4-[4-(2-hydroxypropan-2-yl)-6-[(3S)-3-methylmorpholin-4-yl]pyrimidin-2-yl]phenyl]thiourea

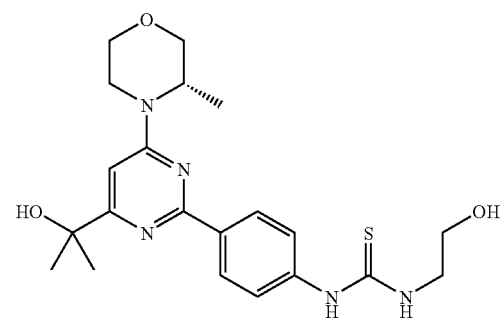

A solution of di(imidazol-1-yl)methanethione (84 mg, 0.46 mmol) in DCM (2 mL) was added to a stirred solution of 2-[2-(4-aminophenyl)-6-[(3S)-3-methylmorpholin-4-yl]pyrimidin-4-yl]propan-2-ol (100 mg, 0.3 mmol) in DCM (2 mL) and THF (1 mL) over a period of 2 minutes under nitrogen. The resulting solution was stirred at RT for 2 hours. Ethanolamine (91.5 mg, 0.46 mmol) and triethylamine (0.1 mL) were added to the reaction mixture. The resulting solution was stirred at RT for 4 hours. The reaction mixture was evaporated to dryness and redissolved in DMF. The crude product was purified by preparative HPLC to give the desired material as a white solid (5 mg).

NMR Spectrum: $^1$H NMR (399.902 MHz, DMSO) δ 1.23 (3H, d), 1.46 (6H, s), 3.20 (1H, m), 3.50 (1H, m), 3.57 (4H, m), 3.64 (1H, m), 3.77 (1H, m), 3.98 (1H, m), 4.16 (1H, m), 4.54 (1H, m), 4.84 (1H, m), 5.24 (1H, s), 6.84 (1H, s), 7.59 (2H, d), 7.85 (1H, s), 8.29 (2H, d), 9.81 (1H, s)

LCMS Spectrum: m/z (ESI+)(M+H)+=432; HPLC tR=1.76 min.

The compounds below were prepared in an analogous fashion from 2-[2-(4-aminophenyl)-6-[(3S)-3-methylmorpholin-4-yl]pyrimidin-4-yl]propan-2-ol using the appropriate amine.

EXAMPLE 5a $^1$H NMR (399.902 MHz, DMSO) δ 1.29 (3H, d), 1.52 (6H, s), 3.00 (3H, d), 3.28 (1H, m), 3.55 (1H, m), 3.70 (1H, m), 3.83 (1H, m), 4.03 (1H, m), 4.22 (1H, m), 4.59 (1H, m), 5.30 (1H, m), 6.90 (1H, s), 7.56 (2H, d), 7.87 (1H, s), 8.35 (2H, d), 9.83 (1H, s)

EXAMPLE 5b $^1$H NMR (399.902 MHz, DMSO) δ 0.60 (2H, m), 0.76 (2H, m), 1.24 (3H, d), 1.46 (6H, s), 2.93 (1H, m), 3.22 (1H, m), 3.50 (1H, m), 3.65 (1H, m), 3.77 (1H, m), 3.98 (1H, m), 4.16 (1H, m), 4.54 (1H, m), 5.24 (1H, s), 6.85 (1H, s), 7.57 (2H, d), 8.10 (1H, s), 8.29 (2H, d), 9.52 (1H, s)

EXAMPLE 5c $^1$H NMR (399.902 MHz, DMSO) δ 1.14 (3H, t), 1.24 (3H, d), 1.46 (6H, s), 3.21 (1H, m), 3.50 (3H, m), 3.65 (1H, m),

| Example | Structure | NAME | LCMS MH+ | Retention time (min) |
|---|---|---|---|---|
| 5a | 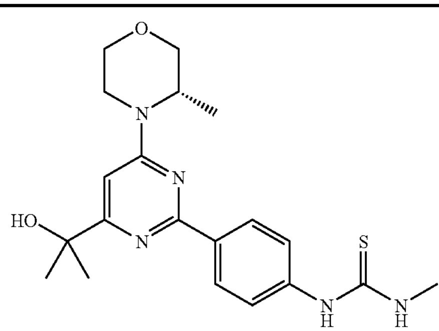 | 1-[4-[4-(2-hydroxypropan-2-yl)-6-[(3S)-3-methylmorpholin-4-yl]pyrimidin-2-yl]phenyl]-3-methylthiourea | 402 | 1.97 |
| 5b | 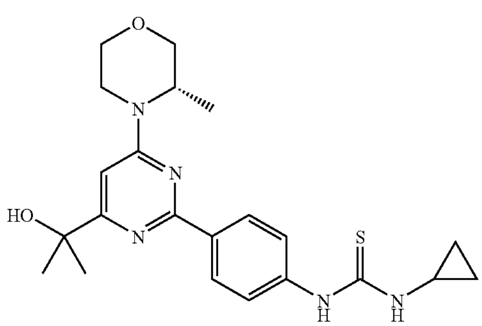 | 3-cyclopropyl-1-[4-[4-(2-hydroxypropan-2-y1)-6-](3S)-3-methylmorpholin-4-yl]pyrimidin-2-yl]phenyl]thiourea | 428 | 2.12 |
| 5c | 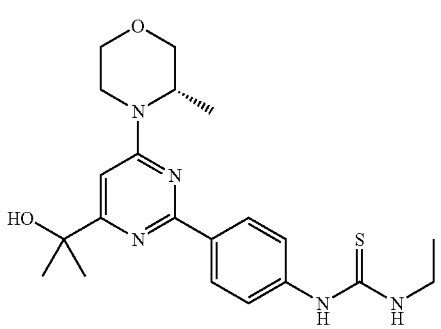 | 3-ethyl-1-[4-[4-(2-hydroxypropan-2-y1)-6-[(3S)-3-methylmorpholin-4-yl]pyrimidin-2-yl]phenyl]thiourea | 416 | 2.17 |

3.77 (1H, m), 3.98 (1H, m), 4.16 (1H, m), 4.54 (1H, m), 5.24 (1H, s), 6.84 (1H, s), 7.52 (2H, d), 7.88 (1H, s), 8.30 (2H, d), 9.65 (1H, s)

The preparation of 2-[2-(4-aminophenyl)-6-[(3S)-3-methylmorpholin-4-yl]pyrimidin-4-yl]propan-2-ol is described below:

2-[2-(4-Aminophenyl)-6-[(3S)-3-methylmorpholin-4-yl]pyrimidin-4-yl]propan-2-ol

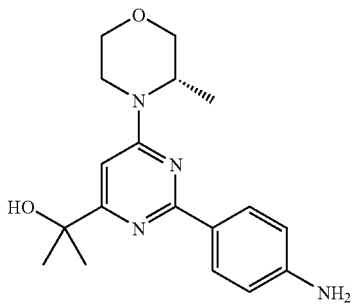

Dichlorobis(triphenylphosphine)palladium(II) (0.492 g, 0.70 mmol) was added to 2-[2-chloro-6-[(3S)-3-methylmorpholin-4-yl]pyrimidin-4-yl]propan-2-ol (3.81 g, 14.02 mmol), 4-(4,4,5,5-tetramethyl-1,3,2-dioxaborolan-2-yl)aniline (3.38 g, 15.42 mmol) and sodium carbonate (4.46 g, 42.06 mmol) in DME (80 mL) and water (20.00 mL) under nitrogen. The resulting solution was stirred at 80° C. for 6 hours. The reaction mixture was diluted with DCM (200 mL), and washed with water (400 mL) twice. The organic layer was dried over MgSO$_4$, filtered and evaporated to afford crude product. The crude product was purified by flash silica chromatography, elution gradient 20 to 60% ethyl acetate in isohexane, to give a material which was further purified by ion exchange chromatography using an SCX column, eluting with 2M ammonia in methanol, to give the desired material as a pink gum (2.78 g).

NMR Spectrum: $^1$H NMR (399.902 MHz, DMSO) δ 1.21 (3H, d), 1.43 (6H, s), 3.17 (1H, m), 3.47 (1H, m), 3.63 (1H, m), 3.76 (1H, m), 3.97 (1H, m), 4.13 (1H, m), 4.48 (1H, m), 5.18 (1H, s), 5.50 (2H, m), 6.59 (2H, d), 6.71 (1H, s), 8.07 (2H, d)

LCMS Spectrum: m/z (ESI+)(M+H)+=329; HPLC tR=1.95 min.

2-[2-Chloro-6-[(3S)-3-methylmorpholin-4-yl]pyrimidin-4-yl]propan-2-ol

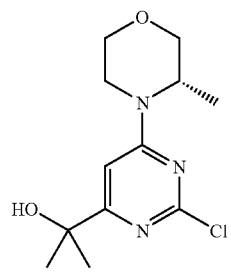

Methyl 2-chloro-6-[(3S)-3-methylmorpholin-4-yl]pyrimidine-4-carboxylate (300 mg) was dissolved in dry THF and cooled to −78° C. Methylmagnesium bromide (3.0M in diethyl ether, 0.74 mL) was added dropwise over 2 min then the reaction allowed to stir at −78° C. for 20 min before allowing to warm to RT. The reaction was stirred for a further 20 min and then quenched with water (2 mL). The reaction was reduced to dryness and partitioned between ethyl acetate (50 mL) and water (50 mL) and the organic layer dried over magnesium sulphate and vacuumed to dryness to the desired material as a white solid (291 mg).

NMR Spectrum: (400.13 MHz, DMSO-d$_6$) δ 1.16-1.23 (3H, m), 1.36 (6H, s), 3.15-3.23 (1H, m), 3.40-3.47 (1H, m), 3.56-3.60 (1H, m), 3.71 (1H, d), 3.91-3.94 (2H, m), 4.34 (1H, s), 5.28 (1H, s), 6.87 (1H, s).

Mass Spectrum; M+H$^+$ 272.

The preparation of methyl 2-chloro-6-[(3S)-3-methylmorpholin-4-yl]pyrimidine-4-carboxylate was described earlier.

The invention claimed is:
1. A compound of formula (I)

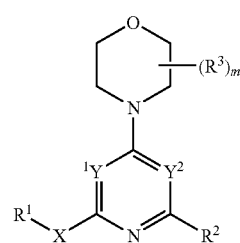

formula (I)

or a pharmaceutically acceptable salt thereof; wherein
m is 0, 1, 2, 3 or 4;
$^1$Y and Y$^2$ are independently N or CR$^8$ provided that one of $^1$Y and Y$^2$ is N and the other is CR$^8$;
X is a linker group selected from —CR$^4$=CR$^5$—, —CR$^4$=CR$^5$CR$^6$R$^7$—, —CR$^6$R$^7$CR$^5$=CR$^4$—, —C≡C—, —C≡CCR$^6$R$^7$—, —CR$^6$R$^7$C≡C—, —NR$^4$CR$^6$R$^7$—, —OCR$^6$R$^7$—, —SCR$^6$R$^7$—, —S(O)CR$^6$R$^7$—, —S(O)$_2$CR$^6$R$^7$—, —C(O)NR$^4$CR$^6$R$^7$—, —NR$^4$C(O)CR$^6$R$^7$—, —NR$^4$C(O)NR$^5$CR$^6$R$^7$—, —NR$^4$S(O)$_2$CR$^6$R$^7$—, —S(O)$_2$NR$^4$CR$^6$R$^7$—, —C(O)NR$^4$—, —NR$^4$C(O)—, —NR$^4$C(O)NR$^5$—, —S(O)$_2$NR$^4$— and —NR$^4$S(O)$_2$—;
R$^1$ is a group selected from hydrogen, C$_{1-6}$alkyl, C$_{2-6}$alkenyl, C$_{2-6}$alkynyl, carbocyclyl, carbocyclylC$_{1-6}$alkyl, heterocyclyl and heterocyclylC$_{1-6}$alkyl, which group is optionally substituted by one or more substituent group selected from halo, cyano, nitro, R$^9$, —OR$^9$, —SR$^9$, —SOR$^9$, —SO$_2$R$^9$, —COR$^9$, —CO$_2$R$^9$, —CONR$^9$R$^{10}$, —NR$^9$R$^{10}$, —NR$^9$COR$^{10}$, —NR$^9$CO$_2$R$^{10}$, —NR$^9$CONR$^{10}$R$^{15}$, —NR$^9$COCONR$^{10}$R$^{15}$ and —NR$^9$SO$_2$R$^{10}$;
R$^2$ is

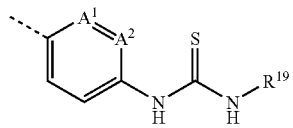

wherein A$^1$ and A$^2$ are selected from CH or N provided that at least one of A$^1$ or A$^2$ is CH;
each R$^3$, when present, is independently selected from halo, cyano, nitro, —R$^{13}$, —OR$^{13}$, —SR$^{13}$, —SOR$^{13}$, —SO$_2$R$^{13}$, —COR$^{13}$, —CO$_2$R$^{13}$, —CONR$^{13}$R$^{14}$, —NR$^{13}$R$^{14}$, —NR$^{13}$COR$^{14}$, —NR$^{13}$CO$_2$R$^{14}$ and —NR$^{13}$SO$_2$R$^{14}$;

R$^4$ and R$^5$ are independently hydrogen or C$_{1-6}$alkyl;

or R$^1$ and R$^4$ together with the atom or atoms to which they are attached form a 4- to 10-membered carbocyclic or heterocyclic ring wherein 1, 2 or 3 ring carbon atoms is optionally replaced with N, O or S and which ring is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^6$ and R$^7$ are independently selected from hydrogen, halo, cyano, nitro and C$_{1-6}$alkyl;

R$^8$ is selected from hydrogen, halo, cyano and C$_{1-6}$alkyl;

R$^9$ and R$^{10}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$ alkyl, hydroxyC$_{1-6}$alkoxy, C$_{1-6}$alkoxyC$_{1-6}$ alkyl, C$_{1-6}$alkoxyC$_{1-6}$alkoxy, amino, C$_{1-6}$alkylamino, bis(C$_{1-6}$ alkyl)amino, aminoC$_{1-6}$alkyl, (C$_{1-6}$alkyl)aminoC$_{1-6}$ alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^{13}$, R$^{14}$, R$^{15}$, and R$^{19}$ are independently hydrogen or a group selected from C$_{1-6}$alkyl, carbocyclyl, carbocyclylC$_{1-6}$alkyl, heterocyclyl and heterocyclylC$_{1-6}$alkyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$ alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

2. A compound of formula (I), or a pharmaceutically acceptable salt thereof, according to claim 1 wherein $^1$Y is CH and Y$^2$ is N.

3. A compound of formula (I), or a pharmaceutically acceptable salt thereof, according to claim 1 wherein either —X—R$^1$ is —C(CH$_3$)$_2$OH, or X is —S(O)$_2$CH$_2$—, —S(O)$_2$CH(CH$_3$)— or —S(O)$_2$C(CH$_3$)$_2$—; and R$^1$ is a group selected from methyl, ethyl, propyl, butyl, isobutyl, tert-butyl, cyclopropyl, cyclopentyl cyclohexyl, phenyl, benzyl, phenethyl, pyridinyl, pyrazolylethyl, furanylmethyl, thienylmethyl, thiazolylmethyl, thiadiazolylmethyl and pyrazinylethyl, which group is optionally substituted by 1 or 2 substituent group selected from amino, halo, cyano, methyl, methoxy, trifluoromethyl, trifluoromethoxy, —NHCOCH$_3$, —CONH$_2$ and —CONHCH$_3$.

4. A compound of formula (I), or a pharmaceutically acceptable salt thereof, according to claim 3 wherein either —X—R$^1$ is —C(CH$_3$)$_2$OH, or X is —S(O)$_2$CH$_2$—, —S(O)$_2$CH(CH$_3$)— or —S(O)$_2$C(CH$_3$)$_2$—; and R$^1$ is a group selected from methyl, —CH$_2$CH$_2$OH and phenyl.

5. A compound of formula (I), or a pharmaceutically acceptable salt thereof, according to claim 1 wherein A$^1$ and A$^2$ are CH.

6. A compound of formula (I), or a pharmaceutically acceptable salt thereof, according to claim 1 wherein R$^{19}$ is hydrogen or a group selected from methyl, ethyl, propyl, i-propyl, butyl, i-butyl, t-butyl, pentyl, cyclopropyl, cyclobutyl, cyclopentyl, cyclohexyl, phenyl, thienyl, imidazoylmethyl, isoxazolyl, pyrazolyl, pyridinyl and pyrimidinyl which group is optionally substituted by one or more substituent groups selected from halo, cyano, nitro, hydroxy, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl.

7. A compound of formula (I), or a pharmaceutically acceptable salt thereof, according to claim 6 wherein R$^{19}$ is a group selected from methyl, ethyl, cyclopropyl, —CH$_2$CH$_2$NMe$_2$, —CH$_2$CH$_2$OH, 4-fluorophenyl, 4-methoxyphenyl, and phenyl.

8. A compound of formula (I), or a pharmaceutically acceptable salt thereof, according to claim 1 selected from any one of:

3-ethyl-1-[4-[4-[(3S)-3-methylmorpholin-4-yl]-6-(methylsulfonylmethyl)pyrimidin-2-yl]phenyl]thiourea, 3-Cyclopropyl-1-[4-[4-[(3S)-3-methylmorpholin-4-yl]-6-(methylsulfonylmethyl)pyrimidin-2-yl]phenyl]thiourea, 3-(4-fluorophenyl)-1-[4-[4-[(3S)-3-methylmorpholin-4-yl]-6-(methylsulfonylmethyl)pyrimidin-2-yl]phenyl]thiourea, 1-[4-[4-[(3S)-3-methylmorpholin-4-yl]-6-(methylsulfonylmethyl)pyrimidin-2-yl]phenyl]-3-phenyl-thiourea, 3-(4-methoxyphenyl)-1-[4-[4-[(3S)-3-methylmorpholin-4-yl]-6-(methylsulfonylmethyl)pyrimidin-2-yl]phenyl]thiourea, 3-cyclopropyl-1-[4-[4-[(3S)-3-methylmorpholin-4-yl]-6-(2-methylsulfonylpropan-2-yl)pyrimidin-2-yl]phenyl]thiourea, 3-methyl-1-[4-[4-[(3S)-3-methylmorpholin-4-yl]-6-(2-methylsulfonylpropan-2-yl)pyrimidin-2-yl]phenyl]thiourea, 3-ethyl-1-[4-[4-[(3S)-3-methylmorpholin-4-yl]-6-(2-methylsulfonylpropan-2-yl)pyrimidin-2-yl]phenyl]thiourea, 3-(2-hydroxyethyl)-1-[4-[4-[(3S)-3-methylmorpholin-4-yl]-6-(2-methylsulfonylpropan-2-yl)pyrimidin-2-yl]phenyl]thiourea, 3-(2-dimethylaminoethyl)-1-[4-[4-[(3S)-3-methylmorpholin-4-yl]-6-(2-methylsulfonylpropan-2-yl)pyrimidin-2-yl]phenyl]thiourea, 1-[4-[4-[2-(Benzenesulfonyl)propan-2-yl]-6-[(3S)-3-methylmorpholin-4-yl]pyrimidin-2-yl]phenyl]-3-methylthiourea, 1-[4-[4-[2-(benzenesulfonyl)propan-2-yl]-6-[(3S)-3-methylmorpholin-4-yl]pyrimidin-2-yl]phenyl]-3-cyclopropylthiourea, 1-[4-[4-[2-(benzenesulfonyl)propan-2-yl]-6-[(3S)-3-methylmorpholin-4-yl]pyrimidin-2-yl]phenyl]-3-ethylthiourea, 1-[4-[4-[2-(benzenesulfonyl)propan-2-yl]-6-[(3S)-3-methylmorpholin-4-yl]pyrimidin-2-yl]phenyl]-3-(2-hydroxyethyl)thiourea, 3-(2-hydroxyethyl)-1-[4-[4-[2-(3-hydroxypropylsulfonyl)propan-2-yl]-6-[(3S)-3-methylmorpholin-4-yl]pyrimidin-2-yl]phenyl]thiourea, 1-[4-[4-[2-(3-hydroxypropylsulfonyl)propan-2-yl]-6-[(3S)-3-methylmorpholin-4-yl]pyrimidin-2-yl]phenyl]-3-methylthiourea, 3-cyclopropyl-1-[4-[4-[2-(3-hydroxypropylsulfonyl)propan-2-yl]-6-[(3S)-3-methylmorpholin-4-yl]pyrimidin-2-yl]phenyl]thiourea, 3-ethyl-1-[4-[4-[2-(3-hydroxypropylsulfonyl)propan-2-yl]-6-[(3S)-3-methylmorpholin-4-yl]pyrimidin-2-yl]phenyl]thiourea, 3-(2-hydroxyethyl)-1-[4-[4-(2-hydroxypropan-2-yl)-6-[(3S)-3-methylmorpholin-4-yl]pyrimidin-2-yl]phenyl]thiourea, 1-[4-[4-(2-hydroxypropan-2-yl)-6-[(3S)-3-methylmorpholin-4-yl]pyrimidin-2-yl]phenyl]-3-methylthiourea, 3-cyclopropyl-1-[4-[4-(2-hydroxypropan-2-yl)-6-[(3S)-3-methylmorpholin-4-yl]pyrimidin-2-yl]phenyl]thiourea, and 3-ethyl-1-[4-[4-(2-hydroxypropan-2-yl)-6-[(3S)-3-methylmorpholin-4-yl]pyrimidin-2-yl]phenyl]thiourea, or a pharmaceutically acceptable salt thereof.

9. A pharmaceutical composition comprising a compound of formula (I) as defined in claim 1, or a pharmaceutically acceptable salt thereof, in association with a pharmaceutically acceptable diluent or carrier.

10. A pharmaceutical composition comprising a compound of formula (I) as defined in claim 8, or a pharmaceutically acceptable salt thereof, in association with a pharmaceutically acceptable diluent or carrier.

11. The compound 3-(2-hydroxyethyl)-1-[4-[4-(2-hydroxypropan-2-yl)-6-[(3S)-3-methylmorpholin-4-yl]pyrimidin-2-yl]phenyl]thiourea, or a pharmaceutically acceptable salt thereof.

12. The compound 3-(2-hydroxyethyl)-1-[4-[4-(2-hydroxypropan-2-yl)-6-[(3S)-3-methylmorpholin-4-yl]pyrimidin-2-yl]phenyl]thiourea.

* * * * *